US012670672B2

(12) United States Patent
Rockel et al.

(10) Patent No.: US 12,670,672 B2
(45) Date of Patent: Jun. 30, 2026

(54) DEVICES, METHODS, AND GRAPHICAL USER INTERFACES FOR THREE-DIMENSIONAL USER EXPERIENCE SESSIONS IN AN EXTENDED REALITY ENVIRONMENT

(71) Applicant: Apple Inc., Cupertino, CA (US)

(72) Inventors: Philipp Rockel, San Francisco, CA (US); Gary I. Butcher, Los Gatos, CA (US); Dorian D. Dargan, Oakland, CA (US); Amy E. Dedonato, San Francisco, CA (US); Charles C. Hoyt, Pacifica, CA (US); Matan Stauber, San Francisco, CA (US); Hugo D. Verweij, Portola Valley, CA (US); Kristi E. Bauerly, Los Altos, CA (US)

(73) Assignee: Apple Inc., Cupertino, CA (US)

( * ) Notice: Subject to any disclaimer, the term of this patent is extended or adjusted under 35 U.S.C. 154(b) by 246 days.

(21) Appl. No.: 18/108,852

(22) Filed: Feb. 13, 2023

(65) Prior Publication Data

US 2023/0306695 A1     Sep. 28, 2023

Related U.S. Application Data

(60) Provisional application No. 63/322,502, filed on Mar. 22, 2022.

(51) Int. Cl.
*G06T 19/00* (2011.01)
*A61B 5/08* (2006.01)
(Continued)

(52) U.S. Cl.
CPC .......... *G06T 19/006* (2013.01); *A61B 5/0816* (2013.01); *G06F 3/013* (2013.01);
(Continued)

(58) Field of Classification Search
CPC ..... G06T 19/006; G06T 13/20; A61B 5/0816; G06F 3/011; G06F 3/012; G06F 3/017
See application file for complete search history.

(56) References Cited

U.S. PATENT DOCUMENTS

| | | |
|---|---|---|
| 7,199,700 B1 | 4/2007 | Mcpherson et al. |
| 8,562,489 B2 | 10/2013 | Burton et al. |
| (Continued) | | |

FOREIGN PATENT DOCUMENTS

| | | |
|---|---|---|
| AU | 2014337787 A1 | 5/2016 |
| CN | 101822894 A | 9/2010 |
| (Continued) | | |

OTHER PUBLICATIONS

Notice of Allowance received for U.S. Appl. No. 17/550,806, mailed on Jun. 17, 2024, 39 pages.
(Continued)

*Primary Examiner* — Chante E Harrison
(74) *Attorney, Agent, or Firm* — YHE Law LLP

(57) ABSTRACT

The present disclosure relates to techniques for providing computer-generated user experience sessions in an extended reality environment. In some embodiments, a computer system provides a computer-generated user experience session with particles that move based on breathing characteristics of a user. In some embodiments, a computer system provides a computer-generated user experience session with options selected based on characteristics of an XR environment. In some embodiments, a computer system provides a computer-generated user experience session with a soundscape having randomly selected curated sound components.

57 Claims, 22 Drawing Sheets

(51) Int. Cl.

| | |
|---|---|
| *G06F 3/01* | (2006.01) |
| *G06T 13/20* | (2011.01) |
| *G06V 10/60* | (2022.01) |
| *G06V 10/74* | (2022.01) |
| *H04S 7/00* | (2006.01) |

(52) U.S. Cl.

CPC ............. *G06T 13/20* (2013.01); *G06V 10/60* (2022.01); *G06V 10/761* (2022.01); *H04S 7/30* (2013.01)

(56) References Cited

U.S. PATENT DOCUMENTS

| | | | |
|---|---|---|---|
| 10,080,530 B2 | 9/2018 | Cheng et al. | |
| 11,931,625 B2 | 3/2024 | D'Auria et al. | |
| 2003/0171643 A1 | 9/2003 | Noguchi et al. | |
| 2004/0254501 A1 | 12/2004 | Mault | |
| 2005/0165609 A1 | 7/2005 | Zuberec et al. | |
| 2007/0129883 A1 | 6/2007 | Kuo et al. | |
| 2007/0208269 A1 | 9/2007 | Mumford et al. | |
| 2008/0072902 A1 | 3/2008 | Setzer et al. | |
| 2008/0319279 A1 | 12/2008 | Ramsay et al. | |
| 2009/0024047 A1 | 1/2009 | Shipley et al. | |
| 2009/0227425 A1 | 9/2009 | Shirasaki et al. | |
| 2009/0263773 A1 | 10/2009 | Kotlyar et al. | |
| 2009/0322686 A1 | 12/2009 | Jayasinghe | |
| 2010/0011307 A1 | 1/2010 | Desfossez et al. | |
| 2010/0035669 A1 | 2/2010 | Jang et al. | |
| 2010/0069774 A1 | 3/2010 | Bingham et al. | |
| 2010/0095961 A1 | 4/2010 | Tornesel et al. | |
| 2010/0273610 A1 | 10/2010 | Johnson | |
| 2010/0331145 A1 | 12/2010 | Lakovic et al. | |
| 2011/0138311 A1* | 6/2011 | Palmer ............... | G06F 3/04812 |
| | | | 715/771 |
| 2012/0015778 A1 | 1/2012 | Lee et al. | |
| 2013/0139107 A1 | 5/2013 | Jung | |
| 2013/0333703 A1 | 12/2013 | Wallace et al. | |
| 2014/0018049 A1 | 1/2014 | Cannon et al. | |
| 2014/0316191 A1 | 10/2014 | De Zambotti et al. | |
| 2014/0344375 A1 | 11/2014 | Hauser et al. | |
| 2015/0096564 A1 | 4/2015 | Cosnek | |
| 2015/0238722 A1 | 8/2015 | Al-Ali | |
| 2015/0283337 A1 | 10/2015 | Adams et al. | |
| 2015/0342518 A1 | 12/2015 | Persidsky et al. | |
| 2016/0007911 A1 | 1/2016 | Wu et al. | |
| 2016/0058337 A1 | 3/2016 | Blahnik et al. | |
| 2016/0114213 A1 | 4/2016 | Lee | |
| 2017/0243508 A1 | 8/2017 | Cheng et al. | |
| 2017/0332972 A1 | 11/2017 | Nagasaki et al. | |
| 2017/0354795 A1 | 12/2017 | Blahnik et al. | |
| 2018/0255335 A1 | 9/2018 | George et al. | |
| 2018/0329584 A1 | 11/2018 | Williams et al. | |
| 2018/0329672 A1 | 11/2018 | Sadak et al. | |
| 2019/0035293 A1 | 1/2019 | Mei | |
| 2019/0314641 A1 | 10/2019 | Malchano et al. | |
| 2019/0320939 A1 | 10/2019 | Orvis et al. | |
| 2020/0149921 A1 | 5/2020 | Hoffman et al. | |
| 2020/0265744 A1 | 8/2020 | Lim et al. | |
| 2021/0113116 A1 | 4/2021 | Chen et al. | |
| 2021/0286502 A1 | 9/2021 | Lemay et al. | |
| 2021/0338971 A1 | 11/2021 | Blahnik et al. | |
| 2022/0080261 A1 | 3/2022 | Li | |
| 2022/0114877 A1 | 4/2022 | Barnes et al. | |
| 2022/0160276 A1 | 5/2022 | Suzuki et al. | |
| 2022/0313080 A1 | 10/2022 | Hernandez et al. | |
| 2022/0374106 A1 | 11/2022 | Arney et al. | |
| 2023/0154126 A1* | 5/2023 | Santhar ............... | G06F 18/2148 |
| | | | 345/419 |
| 2023/0267059 A1 | 8/2023 | Tan et al. | |
| 2023/0347104 A1 | 11/2023 | Blahnik et al. | |
| 2024/0081689 A1* | 3/2024 | Kailay ................. | A61B 5/1123 |
| 2024/0282037 A1* | 8/2024 | Xu .......................... | G06T 13/80 |
| 2024/0404210 A1* | 12/2024 | Rockel .................... | G06F 3/011 |
| 2024/0424372 A1* | 12/2024 | Lee ........................ | B63B 34/30 |

FOREIGN PATENT DOCUMENTS

| | | | | |
|---|---|---|---|---|
| CN | 102488501 A | | 6/2012 | |
| CN | 116051690 A | * | 5/2023 | ............. G06T 13/20 |
| CN | 118946871 A | * | 11/2024 | |
| DE | 102021206259 A1 | * | 12/2021 | .......... G11B 27/102 |
| EP | 2311533 A1 | | 4/2011 | |
| EP | 2866103 A2 | | 4/2015 | |
| EP | 4176796 A1 | * | 5/2023 | .......... A61N 5/1068 |
| GB | 2610435 A | * | 3/2023 | ............. G06F 3/013 |
| JP | 2003-305094 A | | 10/2003 | |
| JP | 2003-339809 A | | 12/2003 | |
| JP | 2007-190275 A | | 8/2007 | |
| JP | 2007-190276 A | | 8/2007 | |
| JP | 2008-279126 A | | 11/2008 | |
| JP | 2009-119068 A | | 6/2009 | |
| JP | 2010-104456 A | | 5/2010 | |
| JP | 2010-533541 A | | 10/2010 | |
| JP | 2012-19852 A | | 2/2012 | |
| JP | 2012-35055 A | | 2/2012 | |
| JP | 2012-524638 A | | 10/2012 | |
| JP | 2012-524639 A | | 10/2012 | |
| JP | 2012-228540 A | | 11/2012 | |
| JP | 2013-128659 A | | 7/2013 | |
| JP | 2013-131215 A | | 7/2013 | |
| JP | 2016-506838 A | | 3/2016 | |
| JP | 2018-504159 A | | 2/2018 | |
| JP | 6991621 B1 | * | 1/2022 | |
| KR | 10-2010-0024503 A | | 3/2010 | |
| KR | 20100118210 A | * | 11/2010 | ............. G06F 3/011 |
| KR | 10-2013-0142412 A | | 12/2013 | |
| KR | 10-2014-0138361 A | | 12/2014 | |
| WO | 2004/082751 A1 | | 9/2004 | |
| WO | 2005/018737 A1 | | 3/2005 | |
| WO | 2008/110956 A1 | | 9/2008 | |
| WO | 2009/002577 A1 | | 12/2008 | |
| WO | 2012/117376 A1 | | 9/2012 | |
| WO | 2014/107795 A1 | | 7/2014 | |
| WO | 2015/039979 A1 | | 3/2015 | |
| WO | 2016/022204 A1 | | 2/2016 | |
| WO | 2016/036472 A1 | | 3/2016 | |
| WO | 2018/209152 A1 | | 11/2018 | |
| WO | 2021/247312 A1 | | 12/2021 | |
| WO | 2022/212070 A1 | | 10/2022 | |
| WO | WO-2023183340 A1 | * | 9/2023 | ............. G06F 3/011 |
| WO | WO-2024220888 A1 | * | 10/2024 | .......... G06F 3/0482 |

OTHER PUBLICATIONS

Supplemental Notice of Allowance received for U.S. Appl. No. 17/550,806, mailed on Jun. 28, 2024, 2 pages.

International Search Report and Written Opinion received for PCT Patent Application No. PCT/US2024/030403, mailed on Sep. 9, 2024, 13 pages.

Office Action received for European Patent Application No. 22731014.1, mailed on Dec. 12, 2024, 8 pages.

Advisory Action received for U.S. Appl. No. 15/372,133, mailed on Aug. 28, 2019, 7 pages.

Advisory Action received for U.S. Appl. No. 15/372,133, mailed on Jun. 2, 2020, 5 pages.

Allthingsgizmo, "How to Multitask on the AppleWatch", Available Online at: https://www.youtube.com/watch?v=Mxt2tfABwLg, Jul. 12, 2015, 2 pages.

Applicant-Initiated Interview Summary received for U.S. Appl. No. 15/372,133, mailed on Dec. 23, 2019, 6 pages.

Applicant-Initiated Interview Summary received for U.S. Appl. No. 15/372,133, mailed on May 4, 2020, 5 pages.

Applicant-Initiated Interview Summary received for U.S. Appl. No. 15/372,133, mailed on Nov. 12, 2020, 5 pages.

Benson Amanda, "Health App of the Month: Move, The Daily Activity Reminder", Think Health, Retrieved from the internet: https://thinkhealth.priorityhealth.com/health-app-of-the-month-move-the-daily-activity-reminder/, Mar. 12, 2015, pp. 1-4.

Breathe Deeply Now! for Windows Phone Version, Online Available at: https://www.appx4fun.com/apps/5402/, Feb. 15, 2015, 11 pages.

(56) References Cited

OTHER PUBLICATIONS

Daniel About Tech, "Workout App Full Review! (Apple Watch)", Available Online at: https://www.youtube.com/watch?v=aHXCNfSccoY, Feb. 19, 2019, 2 pages.

Decision to Grant received for Danish Patent Application No. PA201770384, mailed on Jun. 28, 2019, 2 pages.

Extended European Search Report received for European Patent Application No. 17810736.3, mailed Nov. 7, 2019, 10 pages.

Final Office Action received for U.S. Appl. No. 15/372,133, mailed on Apr. 6, 2020, 16 pages.

Final Office Action received for U.S. Appl. No. 15/372,133, mailed on Apr. 18, 2019, 14 pages.

Gil Lory, "How to Use the Activity and Workout Apps on Apple Watch", Online Available at: https://www.macrumors.com/how-to/apple-watch-activity-workout-apps/, May 4, 2015, 5 pages.

Intention to Grant received for Danish Patent Application No. PA201770384, mailed on Mar. 13, 2019, 2 pages.

Intention to Grant received for Danish Patent Application No. PA201770384, mailed on Nov. 14, 2018, 2 pages.

International Preliminary Report on Patentability received for PCT Patent Application No. PCT/US2017/035309, mailed on Dec. 20, 2018, 28 pages.

International Search Report and Written Opinion received for PCT Patent Application No. PCT/US2017/035309, mailed on Sep. 27, 2017, 31 pages.

International Search Report and Written Opinion received for PCT Patent Application No. PCT/US2022/030309, mailed on Sep. 15, 2022, 14 pages.

Invitation to Pay Additional Fee received for PCT Patent Application No. PCT/US2017/035309, mailed on Jul. 14, 2017, 2 pages.

iphonetricks.org, "Apple Watch Activity App Setup & Usage Tips", Online Available at: https://www.iphonetricks.org/apple-watch-activity-app-setup-usage-tips/, May 4, 2015, 4 pages.

Non-Final Office Action received for U.S. Appl. No. 15/372,133, mailed on Jul. 24, 2018, 13 pages.

Non-Final Office Action received for U.S. Appl. No. 15/372,133, mailed on Oct. 3, 2019, 14 pages.

Non-Final Office Action received for U.S. Appl. No. 15/372,133, mailed on Sep. 14, 2020, 17 pages.

Non-Final Office Action received for U.S. Appl. No. 17/345,092, mailed on Jan. 25, 2023, 36 pages.

Non-Final Office Action received for U.S. Appl. No. 17/550,806, mailed on Nov. 28, 2022, 21 pages.

Notice of Acceptance received for Australian Patent Application No. 2017277848, mailed on Apr. 20, 2020, 3 pages.

Notice of Acceptance received for Australian Patent Application No. 2020203453, mailed on Feb. 10, 2021, 3 pages.

Notice of Acceptance received for Australian Patent Application No. 2021203301, mailed on Feb. 23, 2022, 3 pages.

Notice of Allowance received for Chinese Patent Application No. 201710400594.9, mailed on Jul. 30, 2020, 2 pages (1 page of English Translation and 1 page of Official Copy).

Notice of Allowance received for Japanese Patent Application No. 2018-563158, mailed on Nov. 8, 2019, 4 pages (1 page of English Translation and 3 pages of Official Copy).

Notice of Allowance received for Japanese Patent Application No. 2019-222213, mailed on Aug. 30, 2021, 4 pages (1 page of English Translation and 3 pages of Official Copy).

Notice of Allowance received for Korean Patent Application No. 10-2018-7034689, mailed on Mar. 27, 2020, 6 pages (2 pages of English Translation and 4 pages of Official Copy).

Notice of Allowance received for Korean Patent Application No. 10-2020-7016741, mailed on Feb. 24, 2021, 5 pages (2 pages of English Translation and 3 pages of Official Copy).

Notice of Allowance received for Korean Patent Application No. 10-2021-7015702, mailed on Dec. 27, 2021, 3 pages (Official Copy Only) See Communication Under 37 CFR § 1.98(a) (3).

Notice of Allowance received for U.S. Appl. No. 15/372,133, mailed on Feb. 11, 2021, 8 pages.

Notice of Allowance received for U.S. Appl. No. 15/372,133, mailed on Feb. 26, 2021, 3 pages.

Office Action received for Australian Patent Application No. 2017277848, mailed on Aug. 28, 2019, 4 pages.

Office Action received for Australian Patent Application No. 2017277848, mailed on Jan. 16, 2020, 4 pages.

Office Action received for Australian Patent Application No. 2017277848, mailed on Jun. 13, 2019, 4 pages.

Office Action received for Australian Patent Application No. 2017277848, mailed on Mar. 4, 2020, 3 pages.

Office Action received for Australian Patent Application No. 2017277848, mailed on Nov. 1, 2019, 4 pages.

Office Action received for Australian Patent Application No. 2020203453, mailed on Aug. 12, 2020, 4 pages.

Office Action received for Australian Patent Application No. 2020203453, mailed on Dec. 18, 2020, 4 pages.

Office Action received for Australian Patent Application No. 2020203453, mailed on Oct. 29, 2020, 4 pages.

Office Action received for Australian Patent Application No. 2021203301, mailed on Jan. 18, 2022, 3 pages.

Office Action received for Australian Patent Application No. 2021203301, mailed on Nov. 3, 2021, 3 pages.

Office Action received for Chinese Patent Application No. 201710400594.9, mailed on Apr. 23, 2018., 3 pages (1 page of English Translation and 2 pages of Official copy).

Office Action received for Chinese Patent Application No. 201710400594.9, mailed on Jul. 17, 2017., 2 pages (1 page of English Translation and 1 page of Official Copy).

Office Action received for Chinese Patent Application No. 201710400594.9, mailed on Mar. 20, 2020, 6 pages (3 pages of English Translation and 3 pages of Official Copy).

Office Action received for Chinese Patent Application No. 201710400594.9, mailed on May 14, 2019, 14 pages (5 pages of English Translation and 9 pages of Official Copy).

Office Action received for Chinese Patent Application No. 201710400594.9, mailed on Nov. 15, 2019, 12 pages (5 pages of English Translation and 7 pages of Official Copy).

Office Action received for Danish Patent Application No. PA201770384, mailed on Oct. 27, 2017, 7 pages.

Office Action received for European Patent Application No. 17810736.3, mailed on Nov. 11, 2020, 6 pages.

Office Action received for Japanese Patent Application No. 2019-222213, mailed on Jan. 4, 2021, 9 pages (5 pages of English Translation and 4 pages of Official Copy).

Office Action received for Japanese Patent Application No. 2021-159616, mailed on Dec. 5, 2022, 11 pages (6 pages of English Translation and 5 pages of Official Copy).

Office Action received for Korean Patent Application No. 10-2018-7034689, mailed on Nov. 28, 2019, 11 pages (5 pages of English Translation and 6 pages of Official Copy).

Office Action received for Korean Patent Application No. 10-2020-7016741, mailed on Jul. 22, 2020, 10 pages (4 pages of English Translation and 6 pages of Official Copy).

Office Action received for Korean Patent Application No. 10-2021-7015702, mailed on Jun. 19, 2021, 12 pages (6 pages of English Translation and 6 pages of Official Copy).

Office Action received for Korean Patent Application No. 10-2022-7010343, mailed on May 19, 2022, 12 pages (6 pages of English Translation and 6 pages of Official Copy).

Office Action received for Korean Patent Application No. 10-2022-7010343, mailed on Nov. 17, 2022, 6 pages (3 pages of English Translation and 3 pages of Official Copy).

Paced Breathing, "How to use Paced Breathing", Retrieved from https://pacedbreathing.blogspot.com/2014/03/how-to-use-paced-breathing .html on Sep. 9, 2020, Apr. 3, 2015, 7 pages.

Stachowiak Sandy, "Relax, breathe deep and regain focus with Hear and Now", Available online at: https://appadvice.com/appnn/2016/01/relax-breathe-deep-and-regain-focus-with-hear-and-now, Jan. 6, 2016, 3 pages.

Supplemental Notice of Allowance received for U.S. Appl. No. 15/372,133, mailed on Mar. 26, 2021, 3 pages.

Tiles and Toasts, "Toast Notification and Action Center Overview for Windows 10", Online Available at: https://blogs.msdn.microsoft.

(56) References Cited

OTHER PUBLICATIONS com/tiles_and_toasts/2015/07/08/toast-notification-and-action-center-overview-for-windows-10/, Jul. 8, 2015, 9 pages.

Time Out app, "Release Notes". Online Available at: www.dejal.com/timeout/release, 2016, 8 pages.

Time Out app, Screens shots and user guide. Online Available at: https://web.archive.org/web/20160314023701/http://www.dejal.com/timeout/images/, Mar. 14, 2016, 10 pages.

Wesley, "Apple Watch Series 1", online available at:—http://toolbox.info/blog/archives/1737-unknown.html, May 28, 2015, 5 pages (Official copy only) See Communication Under 37 CFR § 1.98(a) (3).

Windowsunited, "Breathe Deeply Now! Please Take a Deep Breath and Relax", Online Available at: https://windowsunited.de/breathe-deeply-now-die-app-gegen-angszustaende/, Oct. 4, 2014, 8 pages.

Notice of Allowance received for Japanese Patent Application No. 2021-159616, mailed on Apr. 12, 2024, 4 pages (1 page of English Translation and 3 pages of Official Copy).

Office Action received for Chinese Patent Application No. 202011098154.0, mailed on Dec. 26, 2023, 22 pages (11 pages of English Translation and 11 pages of Official Copy).

Notice of Allowance received for Chinese Patent Application No. 202011098154.0, mailed on May 22, 2024, 5 pages (1 page of English Translation and 4 pages of Official Copy).

Advisory Action received for U.S. Appl. No. 17/550,806, mailed on Oct. 26, 2023, 6 pages.

Applicant-Initiated Interview Summary received for U.S. Appl. No. 17/345,092, mailed on Feb. 28, 2023, 5 pages.

Applicant-Initiated Interview Summary received for U.S. Appl. No. 17/550,806, mailed on Apr. 21, 2023, 2 pages.

Applicant-Initiated Interview Summary received for U.S. Appl. No. 17/550,806, mailed on Sep. 15, 2023, 2 pages.

Decision to Grant received for European Patent Application No. 17810736.3, mailed on Jan. 5, 2024, 2 pages.

Extended European Search Report received for European Patent Application No. 23216678.5, mailed on Mar. 7, 2024, 10 pages.

Final Office Action received for U.S. Appl. No. 17/550,806, mailed on Aug. 1, 2023, 21 pages.

Intention to Grant received for European Patent Application No. 17810736.3, mailed on Aug. 8, 2023, 8 pages.

International Preliminary Report on Patentability received for PCT Patent Application No. PCT/US2022/030309, mailed on Nov. 30, 2023, 10 pages.

Search Report and Written Opinion received for PCT Patent Application No. PCT/US2023/015826, mailed on Jul. 31, 2023, 18 pages.

Invitation to Pay Additional Fees and Partial International Search Report received for PCT Patent Application No. PCT/US2023/015826, mailed on Jun. 7, 2023, 10 pages.

Notice of Allowance received for Korean Patent Application No. 10-2022-7010343, mailed on Feb. 27, 2023, 6 pages (2 pages of English Translation and 4 pages of Official Copy).

Notice of Allowance received for Korean Patent Application No. 10-2023-7018493, mailed on Jul. 18, 2023, 7 pages (2 pages of English Translation and 5 pages of Official Copy).

Notice of Allowance received for U.S. Appl. No. 17/345,092, mailed on Apr. 10, 2023, 9 pages.

Office Action received for Chinese Patent Application No. 202011096049.3, mailed on Jan. 9, 2024, 8 pages (4 pages of English Translation and 4 pages of Official Copy).

Office Action received for Chinese Patent Application No. 202011096049.3, mailed on Nov. 3, 2023, 27 pages (12 pages of English Translation and 15 pages of Official Copy).

Office Action received for Japanese Patent Application No. 2021-159616, mailed on Dec. 8, 2023, 4 pages (2 pages of English Translation and 2 pages of Official Copy).

Office Action received for Japanese Patent Application No. 2021-159616, mailed on Jun. 9, 2023, 4 pages (2 pages of English Translation and 2 pages of Official Copy).

Hang et al., "Oh App, Where Art Thou? On App Launching Habits of Smartphone Users", Proceedings of the 15th international conference on Human-computer interaction with mobile devices and services, MobileHCI '13, Online available at: https://dl.acm.org/doi/10.1145/2493190.2493219, Aug. 27-30, 2013, 4 pages.

Wikipedia, "Nike+iPod", Online available at:http://en.wikipedia.org/w/index.php?title=Nike%2BiPod&oldid=420671395, Mar. 25, 2011, pp. 1-4.

Zou et al., "Prophet: What App You Wish to Use Next", UbiComp '13, Online available at: DOI: 10.1145/2494091.2494146, Sep. 8-12, 2013, pp. 167-170.

International Preliminary Report on Patentability received for PCT Patent Application No. PCT/US2023/015826, mailed on Oct. 3, 2024, 12 pages.

Notice of Allowance received for Chinese Patent Application No. 202011096049.3, mailed on Mar. 20, 2024, 2 pages (1 page of English Translation and 1 page of Official Copy).

Intention to Grant received for European Patent Application No. 22731014.1, mailed on Jun. 2, 2025, 9 pages.

Notice of Allowance received for U.S. Appl. No. 18/375,323, mailed on Jul. 30, 2025, 7 pages.

Office Action received for European Patent Application No. 23216678.5, mailed on Aug. 1, 2025, 5 pages.

Decision to Grant received for European Patent Application No. 22731014.1, mailed on Sep. 25, 2025, 2 pages.

Non-Final Office Action received for U.S. Appl. No. 18/375,323, mailed on May 21, 2025, 44 pages.

Notice of Allowance received for Japanese Patent Application No. 2024-012084, mailed on Feb. 7, 2025, 4 pages (1 page of English Translation and 3 pages of Official Copy).

Intention to Grant received for European Patent Application No. 23716076.7, mailed on Dec. 1, 2025, 9 pages.

Intention to Grant received for European Patent Application No. 23716076.7, mailed on Apr. 28, 2026, 9 pages.

* cited by examiner

702

712

705

714

710

732-2

731

732-1

739

CUSTOMIZE

DONE

738

702-2

732

DURATION

5
MIN

10
MIN

15
MIN 732-3

730

CADENCE

734

5
BPM

7
BPM

10
BPM 734-3

GUIDE

736

702-1

734-1

736-1

734-2

735

736-2

733

701

703

707

FOCUS ON YOUR
BREATHING... INHALE...

EXHALE 740-2

IMAGINE YOURSELF IN A RELAXING PLACE...

FOCUS ON YOUR BREATHING 702
700a
704
705
712
702-2
754 TODAY
5 MINUTES
756 THIS WEEK
3 DAYS
752
750
712 CONTINUE
DONE
758
760
710
702-1
701
MAINTAIN FOCUS AND FEEL
YOURSELF BACK IN THE
SPACE AROUND YOU
740-5
711
703
707

702

700a 773-2  773-1  765

770

772

702-2

MEDITATION  10 MINS

TAKE SOME TIME
TO FOCUS ON THE
PRESENT THROUGH
BREATHING AND
REFLECTION

773

767

START 702-1

778  776

701

703

774

707

702

765

702-2

770

772

709-5
709-6
709-4
701
702-1
709-7
780-1

FOCUS ON YOUR BREATH...
NOW, INHALE...

774

703

709-8

709-3

709-9

707

702

792

787

790

702-2

FOCUS ON YOUR BREATH...
AND INHALE...

785-1

709-5

709-6

709-4

701

709-7

794

703

709-3

709-8

709-9

707

Figure 8:
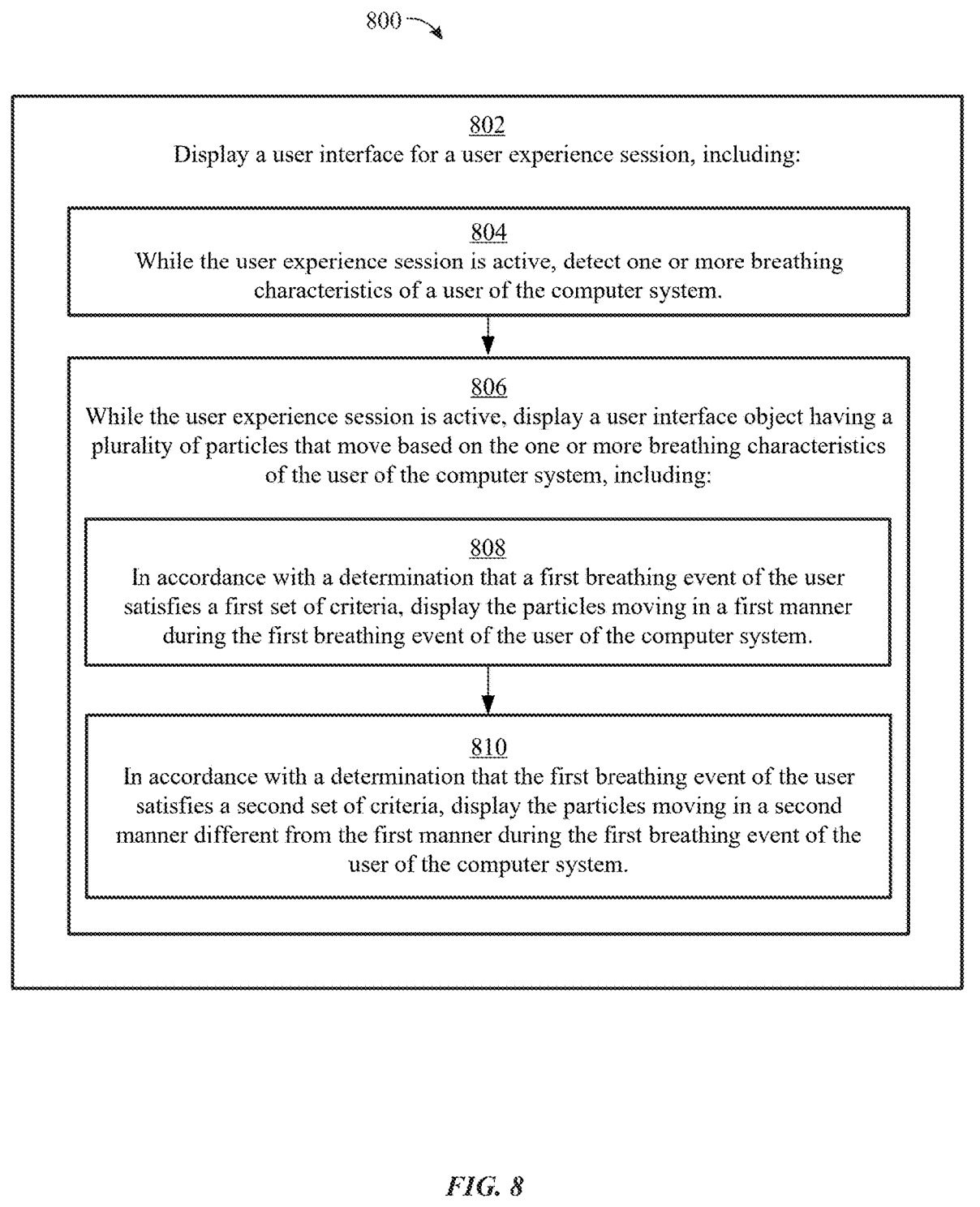

800 ➘

<u>802</u>
Display a user interface for a user experience session, including:

<u>804</u>
While the user experience session is active, detect one or more breathing characteristics of a user of the computer system.

<u>806</u>
While the user experience session is active, display a user interface object having a plurality of particles that move based on the one or more breathing characteristics of the user of the computer system, including:

<u>808</u>
In accordance with a determination that a first breathing event of the user satisfies a first set of criteria, display the particles moving in a first manner during the first breathing event of the user of the computer system.

<u>810</u>
In accordance with a determination that the first breathing event of the user satisfies a second set of criteria, display the particles moving in a second manner different from the first manner during the first breathing event of the user of the computer system.

Figure 9:
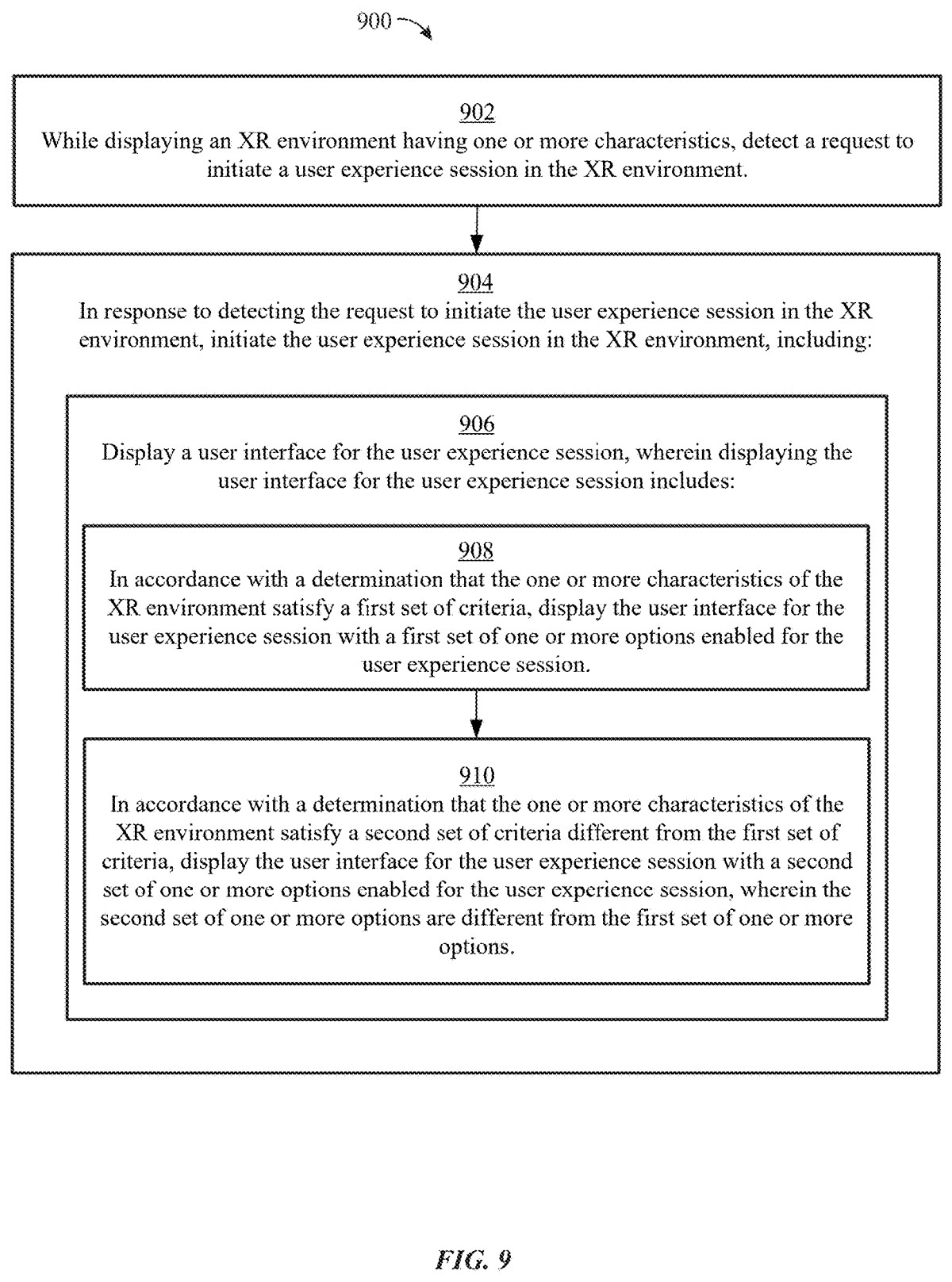

902
While displaying an XR environment having one or more characteristics, detect a request to initiate a user experience session in the XR environment.

904
In response to detecting the request to initiate the user experience session in the XR environment, initiate the user experience session in the XR environment, including:

906
Display a user interface for the user experience session, wherein displaying the user interface for the user experience session includes:

908
In accordance with a determination that the one or more characteristics of the XR environment satisfy a first set of criteria, display the user interface for the user experience session with a first set of one or more options enabled for the user experience session.

910
In accordance with a determination that the one or more characteristics of the XR environment satisfy a second set of criteria different from the first set of criteria, display the user interface for the user experience session with a second set of one or more options enabled for the user experience session, wherein the second set of one or more options are different from the first set of one or more options.

Figure 10A:
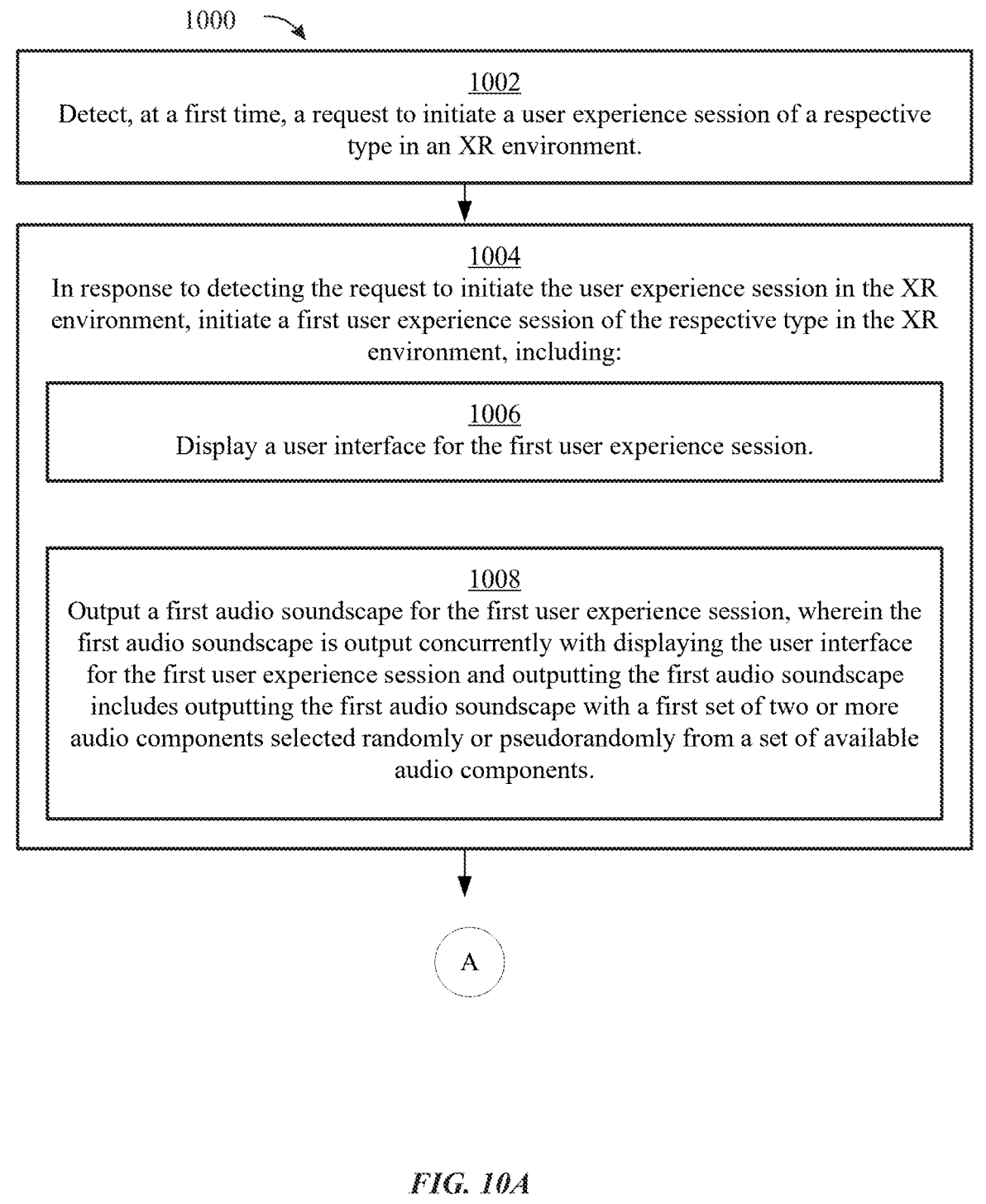

1002
Detect, at a first time, a request to initiate a user experience session of a respective type in an XR environment.

1004
In response to detecting the request to initiate the user experience session in the XR environment, initiate a first user experience session of the respective type in the XR environment, including:

1006
Display a user interface for the first user experience session.

1008
Output a first audio soundscape for the first user experience session, wherein the first audio soundscape is output concurrently with displaying the user interface for the first user experience session and outputting the first audio soundscape includes outputting the first audio soundscape with a first set of two or more audio components selected randomly or pseudorandomly from a set of available audio components.

1010
Detect, at a second time different from the first time, a request to initiate a user experience session of the respective type in an XR environment.

1012
In response to detecting the request to initiate the user experience session in the XR environment, initiate a second user experience session of the respective type in the XR environment, including:

1014
Display a user interface for the second user experience session.

1016
Output a second audio soundscape for the second user experience session, wherein the second audio soundscape is output concurrently with displaying the user interface for the second user experience session and outputting the second audio soundscape includes outputting the second audio soundscape with a second set of two or more audio components selected randomly or pseudorandomly from the set of available audio components.

*FIG. 10B*

DEVICES, METHODS, AND GRAPHICAL USER INTERFACES FOR THREE-DIMENSIONAL USER EXPERIENCE SESSIONS IN AN EXTENDED REALITY ENVIRONMENT

CROSS-REFERENCE TO RELATED APPLICATIONS

This application claims priority to U.S. Provisional Application No. 63/322,502, entitled "DEVICES, METHODS, AND GRAPHICAL USER INTERFACES FOR THREE-DIMENSIONAL USER EXPERIENCE SESSIONS IN AN EXTENDED REALITY ENVIRONMENT," filed Mar. 22, 2022, the entire contents of which is hereby incorporated by reference in its entirety.

TECHNICAL FIELD

The present disclosure relates generally to computer systems that are in communication with a display generation component, one or more sensors, and, optionally, one or more audio generation components that provide computer-generated experiences, including, but not limited to, electronic devices that provide virtual reality and mixed reality experiences via a display.

BACKGROUND

The development of computer systems for augmented reality has increased significantly in recent years. Example augmented reality environments include at least some virtual elements that replace or augment the physical world. Input devices, such as cameras, controllers, joysticks, touch-sensitive surfaces, and touch-screen displays for computer systems and other electronic computing devices are used to interact with virtual/augmented reality environments. Example virtual elements include virtual objects, such as digital images, video, text, icons, and control elements such as buttons and other graphics.

SUMMARY

Some methods and interfaces for providing computer-generated user experience sessions in an extended reality environment are cumbersome, inefficient, and limited. For example, systems that provide insufficient feedback for performing actions associated with virtual objects, systems that require a series of inputs to achieve a desired outcome in an augmented reality environment, and systems in which manipulation of virtual objects are complex, tedious, and error-prone, create a significant cognitive burden on a user, and detract from the experience with the virtual/augmented reality environment. In addition, these methods take longer than necessary, thereby wasting energy of the computer system. This latter consideration is particularly important in battery-operated devices.

Accordingly, there is a need for computer systems with improved methods and interfaces for providing computer-generated user experience sessions in an extended reality environment that make interaction with the computer systems more efficient and intuitive for a user. Such methods and interfaces optionally complement or replace conventional methods for providing extended reality experiences to users. Such methods and interfaces reduce the number, extent, and/or nature of the inputs from a user by helping the user to understand the connection between provided inputs and device responses to the inputs, thereby creating a more efficient human-machine interface.

The above deficiencies and other problems associated with user interfaces for computer systems are reduced or eliminated by the disclosed systems. In some embodiments, the computer system is a desktop computer with an associated display. In some embodiments, the computer system is portable device (e.g., a notebook computer, tablet computer, or handheld device). In some embodiments, the computer system is a personal electronic device (e.g., a wearable electronic device, such as a watch, or a head-mounted device). In some embodiments, the computer system has a touchpad. In some embodiments, the computer system has one or more cameras. In some embodiments, the computer system has a touch-sensitive display (also known as a "touch screen" or "touch-screen display"). In some embodiments, the computer system has one or more eye-tracking components. In some embodiments, the computer system has one or more hand-tracking components. In some embodiments, the computer system has one or more output devices in addition to the display generation component, the output devices including one or more tactile output generators and/or one or more audio output devices. In some embodiments, the computer system has a graphical user interface (GUI), one or more processors, memory and one or more modules, programs or sets of instructions stored in the memory for performing multiple functions. In some embodiments, the user interacts with the GUI through a stylus and/or finger contacts and gestures on the touch-sensitive surface, movement of the user's eyes and hand in space relative to the GUI (and/or computer system) or the user's body as captured by cameras and other movement sensors, and/or voice inputs as captured by one or more audio input devices. In some embodiments, the functions performed through the interactions optionally include image editing, drawing, presenting, word processing, spreadsheet making, game playing, telephoning, video conferencing, e-mailing, instant messaging, workout support, digital photographing, digital videoing, web browsing, digital music playing, note taking, and/or digital video playing. Executable instructions for performing these functions are, optionally, included in a transitory and/or non-transitory computer readable storage medium or other computer program product configured for execution by one or more processors.

There is a need for electronic devices with improved methods and interfaces for providing computer-generated user experience sessions in an extended reality environment. Such methods and interfaces may complement or replace conventional methods for interacting with a three-dimensional environment. Such methods and interfaces reduce the number, extent, and/or the nature of the inputs from a user and produce a more efficient human-machine interface. For battery-operated computing devices, such methods and interfaces conserve power and increase the time between battery charges. Such methods and interfaces also provide more realistic user experiences while saving storage space for visual and audio components of the user experience sessions.

In accordance with some embodiments, a method is described. The method is performed at a computer system that is in communication with a display generation component and one or more sensors. The method comprises: displaying, via the display generation component, a user interface for a user experience session, including: while the user experience session is active: detecting, via the one or more sensors, one or more breathing characteristics of a user of the computer system; and displaying a user interface object having a plurality of particles that move based on the one or more breathing characteristics of the user of the computer system, including: in accordance with a determination that a first breathing event of the user of the computer system satisfies a first set of criteria, displaying the particles of the user interface object moving in a first manner during the first breathing event of the user of the computer system; and in accordance with a determination that the first breathing event of the user of the computer system satisfies a second set of criteria, displaying the particles of the user interface object moving in a second manner different from the first manner during the first breathing event of the user of the computer system.

In accordance with some embodiments, a non-transitory computer-readable storage medium is described. The non-transitory computer-readable storage medium stores one or more programs configured to be executed by one or more processors of a computer system that is in communication with a display generation component and one or more sensors, the one or more programs including instructions for: displaying, via the display generation component, a user interface for a user experience session, including: while the user experience session is active: detecting, via the one or more sensors, one or more breathing characteristics of a user of the computer system; and displaying a user interface object having a plurality of particles that move based on the one or more breathing characteristics of the user of the computer system, including: in accordance with a determination that a first breathing event of the user of the computer system satisfies a first set of criteria, displaying the particles of the user interface object moving in a first manner during the first breathing event of the user of the computer system; and in accordance with a determination that the first breathing event of the user of the computer system satisfies a second set of criteria, displaying the particles of the user interface object moving in a second manner different from the first manner during the first breathing event of the user of the computer system.

In accordance with some embodiments, a transitory computer-readable storage medium is described. The non-transitory computer-readable storage medium stores one or more programs configured to be executed by one or more processors of a computer system that is in communication with a display generation component and one or more sensors, the one or more programs including instructions for: displaying, via the display generation component, a user interface for a user experience session, including: while the user experience session is active: detecting, via the one or more sensors, one or more breathing characteristics of a user of the computer system; and displaying a user interface object having a plurality of particles that move based on the one or more breathing characteristics of the user of the computer system, including: in accordance with a determination that a first breathing event of the user of the computer system satisfies a first set of criteria, displaying the particles of the user interface object moving in a first manner during the first breathing event of the user of the computer system; and in accordance with a determination that the first breathing event of the user of the computer system satisfies a second set of criteria, displaying the particles of the user interface object moving in a second manner different from the first manner during the first breathing event of the user of the computer system.

In accordance with some embodiments, a computer system is described. The computer system is configured to communicate with a display generation component and one or more sensors. The computer system comprises: one or more processors; and memory storing one or more programs configured to be executed by the one or more processors, the one or more programs including instructions for: displaying, via the display generation component, a user interface for a user experience session, including: while the user experience session is active: detecting, via the one or more sensors, one or more breathing characteristics of a user of the computer system; and displaying a user interface object having a plurality of particles that move based on the one or more breathing characteristics of the user of the computer system, including: in accordance with a determination that a first breathing event of the user of the computer system satisfies a first set of criteria, displaying the particles of the user interface object moving in a first manner during the first breathing event of the user of the computer system; and in accordance with a determination that the first breathing event of the user of the computer system satisfies a second set of criteria, displaying the particles of the user interface object moving in a second manner different from the first manner during the first breathing event of the user of the computer system.

In accordance with some embodiments, a computer system is described. The computer system is configured to communicate with a display generation component and one or more sensors. The computer system comprises: means for displaying, via the display generation component, a user interface for a user experience session, including: while the user experience session is active: detecting, via the one or more sensors, one or more breathing characteristics of a user of the computer system; and displaying a user interface object having a plurality of particles that move based on the one or more breathing characteristics of the user of the computer system, including: in accordance with a determination that a first breathing event of the user of the computer system satisfies a first set of criteria, displaying the particles of the user interface object moving in a first manner during the first breathing event of the user of the computer system; and in accordance with a determination that the first breathing event of the user of the computer system satisfies a second set of criteria, displaying the particles of the user interface object moving in a second manner different from the first manner during the first breathing event of the user of the computer system.

In accordance with some embodiments, a computer program product is described. The computer program product comprises one or more programs configured to be executed by one or more processors of a computer system that is in communication with a display generation component and one or more sensors, the one or more programs including instructions for: displaying, via the display generation component, a user interface for a user experience session, including: while the user experience session is active: detecting, via the one or more sensors, one or more breathing characteristics of a user of the computer system; and displaying a user interface object having a plurality of particles that move based on the one or more breathing characteristics of the user of the computer system, including: in accordance with a determination that a first breathing event of the user of the computer system satisfies a first set of criteria, displaying the particles of the user interface object moving in a first manner during the first breathing event of the user of the computer system; and in accordance with a determination that the first breathing event of the user of the computer system satisfies a second set of criteria, displaying the particles of the user interface object moving in a second manner different from the first manner during the first breathing event of the user of the computer system.

In accordance with some embodiments, a method is described. The method is performed at a computer system that is in communication with a display generation component and one or more sensors. The method comprises: while displaying an XR environment having one or more characteristics, detecting, via the one or more sensors, a request to initiate a user experience session in the XR environment; and in response to detecting the request to initiate the user experience session in the XR environment, initiating the user experience session in the XR environment, including: displaying, via the display generation component, a user interface for the user experience session, wherein displaying the user interface for the user experience session includes: in accordance with a determination that the one or more characteristics of the XR environment satisfy a first set of criteria, displaying the user interface for the user experience session with a first set of one or more options enabled for the user experience session; and in accordance with a determination that the one or more characteristics of the XR environment satisfy a second set of criteria different from the first set of criteria, displaying the user interface for the user experience session with a second set of one or more options enabled for the user experience session, wherein the second set of one or more options are different from the first set of one or more options.

In accordance with some embodiments, a non-transitory computer-readable storage medium is described. The non-transitory computer-readable storage medium stores one or more programs configured to be executed by one or more processors of a computer system that is in communication with a display generation component and one or more sensors, the one or more programs including instructions for: while displaying an XR environment having one or more characteristics, detecting, via the one or more sensors, a request to initiate a user experience session in the XR environment; and in response to detecting the request to initiate the user experience session in the XR environment, initiating the user experience session in the XR environment, including: displaying, via the display generation component, a user interface for the user experience session, wherein displaying the user interface for the user experience session includes: in accordance with a determination that the one or more characteristics of the XR environment satisfy a first set of criteria, displaying the user interface for the user experience session with a first set of one or more options enabled for the user experience session; and in accordance with a determination that the one or more characteristics of the XR environment satisfy a second set of criteria different from the first set of criteria, displaying the user interface for the user experience session with a second set of one or more options enabled for the user experience session, wherein the second set of one or more options are different from the first set of one or more options.

In accordance with some embodiments, a transitory computer-readable storage medium is described. The non-transitory computer-readable storage medium stores one or more programs configured to be executed by one or more processors of a computer system that is in communication with a display generation component and one or more sensors, the one or more programs including instructions for: while displaying an XR environment having one or more characteristics, detecting, via the one or more sensors, a request to initiate a user experience session in the XR environment; and in response to detecting the request to initiate the user experience session in the XR environment, initiating the user experience session in the XR environment, including: displaying, via the display generation component, a user interface for the user experience session, wherein displaying the user interface for the user experience session includes: in accordance with a determination that the one or more characteristics of the XR environment satisfy a first set of criteria, displaying the user interface for the user experience session with a first set of one or more options enabled for the user experience session; and in accordance with a determination that the one or more characteristics of the XR environment satisfy a second set of criteria different from the first set of criteria, displaying the user interface for the user experience session with a second set of one or more options enabled for the user experience session, wherein the second set of one or more options are different from the first set of one or more options.

In accordance with some embodiments, a computer system is described. The computer system is configured to communicate with a display generation component and one or more sensors. The computer system comprises: one or more processors; and memory storing one or more programs configured to be executed by the one or more processors, the one or more programs including instructions for: while displaying an XR environment having one or more characteristics, detecting, via the one or more sensors, a request to initiate a user experience session in the XR environment; and in response to detecting the request to initiate the user experience session in the XR environment, initiating the user experience session in the XR environment, including: displaying, via the display generation component, a user interface for the user experience session, wherein displaying the user interface for the user experience session includes: in accordance with a determination that the one or more characteristics of the XR environment satisfy a first set of criteria, displaying the user interface for the user experience session with a first set of one or more options enabled for the user experience session; and in accordance with a determination that the one or more characteristics of the XR environment satisfy a second set of criteria different from the first set of criteria, displaying the user interface for the user experience session with a second set of one or more options enabled for the user experience session, wherein the second set of one or more options are different from the first set of one or more options.

In accordance with some embodiments, a computer system is described. The computer system is configured to communicate with a display generation component and one or more sensors. The computer system comprises: means for, while displaying an XR environment having one or more characteristics, detecting, via the one or more sensors, a request to initiate a user experience session in the XR environment; and means for, in response to detecting the request to initiate the user experience session in the XR environment, initiating the user experience session in the XR environment, including: means for displaying, via the display generation component, a user interface for the user experience session, wherein displaying the user interface for the user experience session includes: in accordance with a determination that the one or more characteristics of the XR environment satisfy a first set of criteria, displaying the user interface for the user experience session with a first set of one or more options enabled for the user experience session; and in accordance with a determination that the one or more characteristics of the XR environment satisfy a second set of criteria different from the first set of criteria, displaying the user interface for the user experience session with a second set of one or more options enabled for the user experience session, wherein the second set of one or more options are different from the first set of one or more options.

In accordance with some embodiments, a computer program product is described. The computer program product comprises one or more programs configured to be executed by one or more processors of a computer system that is in communication with a display generation component and one or more sensors, the one or more programs including instructions for: while displaying an XR environment having one or more characteristics, detecting, via the one or more sensors, a request to initiate a user experience session in the XR environment; and in response to detecting the request to initiate the user experience session in the XR environment, initiating the user experience session in the XR environment, including: displaying, via the display generation component, a user interface for the user experience session, wherein displaying the user interface for the user experience session includes: in accordance with a determination that the one or more characteristics of the XR environment satisfy a first set of criteria, displaying the user interface for the user experience session with a first set of one or more options enabled for the user experience session; and in accordance with a determination that the one or more characteristics of the XR environment satisfy a second set of criteria different from the first set of criteria, displaying the user interface for the user experience session with a second set of one or more options enabled for the user experience session, wherein the second set of one or more options are different from the first set of one or more options.

In accordance with some embodiments, a method is described. The method is performed at a computer system that is in communication with a display generation component, an audio generation component, and one or more sensors. The method comprises: detecting, at a first time, via the one or more sensors, a request to initiate a user experience session of a respective type in an XR environment; in response to detecting the request to initiate the user experience session in the XR environment, initiating a first user experience session of the respective type in the XR environment, including: displaying, via the display generation component, a user interface for the first user experience session; and outputting, via the audio generation component, a first audio soundscape for the first user experience session, wherein the first audio soundscape is output concurrently with displaying the user interface for the first user experience session and outputting the first audio soundscape includes outputting the first audio soundscape with a first set of two or more audio components selected randomly or pseudorandomly from a set of available audio components; detecting, at a second time that is different from the first time, via the one or more sensors, a request to initiate a user experience session of the respective type in an XR environment; and in response to detecting the request to initiate the user experience session in the XR environment, initiating a second user experience session of the respective type in the XR environment, including: displaying, via the display generation component, a user interface for the second user experience session; and outputting, via the audio generation component, a second audio soundscape for the second user experience session, wherein the second audio soundscape is output concurrently with displaying the user interface for the second user experience session and outputting the second audio soundscape includes outputting the second audio soundscape with a second set of two or more audio components selected randomly or pseudorandomly from the set of available audio components.

In accordance with some embodiments, a non-transitory computer-readable storage medium is described. The non-transitory computer-readable storage medium stores one or more programs configured to be executed by one or more processors of a computer system that is in communication with a display generation component, an audio generation component, and one or more sensors, the one or more programs including instructions for: detecting, at a first time, via the one or more sensors, a request to initiate a user experience session of a respective type in an XR environment; in response to detecting the request to initiate the user experience session in the XR environment, initiating a first user experience session of the respective type in the XR environment, including: displaying, via the display generation component, a user interface for the first user experience session; and outputting, via the audio generation component, a first audio soundscape for the first user experience session, wherein the first audio soundscape is output concurrently with displaying the user interface for the first user experience session and outputting the first audio soundscape includes outputting the first audio soundscape with a first set of two or more audio components selected randomly or pseudorandomly from a set of available audio components; detecting, at a second time that is different from the first time, via the one or more sensors, a request to initiate a user experience session of the respective type in an XR environment; and in response to detecting the request to initiate the user experience session in the XR environment, initiating a second user experience session of the respective type in the XR environment, including: displaying, via the display generation component, a user interface for the second user experience session; and outputting, via the audio generation component, a second audio soundscape for the second user experience session, wherein the second audio soundscape is output concurrently with displaying the user interface for the second user experience session and outputting the second audio soundscape includes outputting the second audio soundscape with a second set of two or more audio components selected randomly or pseudorandomly from the set of available audio components.

In accordance with some embodiments, a transitory computer-readable storage medium is described. The non-transitory computer-readable storage medium stores one or more programs configured to be executed by one or more processors of a computer system that is in communication with a display generation component, an audio generation component, and one or more sensors, the one or more programs including instructions for: detecting, at a first time, via the one or more sensors, a request to initiate a user experience session of a respective type in an XR environment; in response to detecting the request to initiate the user experience session in the XR environment, initiating a first user experience session of the respective type in the XR environment, including: displaying, via the display generation component, a user interface for the first user experience session; and outputting, via the audio generation component, a first audio soundscape for the first user experience session, wherein the first audio soundscape is output concurrently with displaying the user interface for the first user experience session and outputting the first audio soundscape includes outputting the first audio soundscape with a first set of two or more audio components selected randomly or pseudorandomly from a set of available audio components; detecting, at a second time that is different from the first time, via the one or more sensors, a request to initiate a user experience session of the respective type in an XR environment; and in response to detecting the request to initiate the user experience session in the XR environment, initiating a second user experience session of the respective type in the XR environment, including: displaying, via the display generation component, a user interface for the second user experience session; and outputting, via the audio generation component, a second audio soundscape for the second user experience session, wherein the second audio soundscape is output concurrently with displaying the user interface for the second user experience session and outputting the second audio soundscape includes outputting the second audio soundscape with a second set of two or more audio components selected randomly or pseudorandomly from the set of available audio components.

In accordance with some embodiments, a computer system is described. The computer system is configured to communicate with a display generation component, an audio generation component, and one or more sensors. The computer system comprises: one or more processors; and memory storing one or more programs configured to be executed by the one or more processors, the one or more programs including instructions for: detecting, at a first time, via the one or more sensors, a request to initiate a user experience session of a respective type in an XR environment; in response to detecting the request to initiate the user experience session in the XR environment, initiating a first user experience session of the respective type in the XR environment, including: displaying, via the display generation component, a user interface for the first user experience session; and outputting, via the audio generation component, a first audio soundscape for the first user experience session, wherein the first audio soundscape is output concurrently with displaying the user interface for the first user experience session and outputting the first audio soundscape includes outputting the first audio soundscape with a first set of two or more audio components selected randomly or pseudorandomly from a set of available audio components; detecting, at a second time that is different from the first time, via the one or more sensors, a request to initiate a user experience session of the respective type in an XR environment; and in response to detecting the request to initiate the user experience session in the XR environment, initiating a second user experience session of the respective type in the XR environment, including: displaying, via the display generation component, a user interface for the second user experience session; and outputting, via the audio generation component, a second audio soundscape for the second user experience session, wherein the second audio soundscape is output concurrently with displaying the user interface for the second user experience session and outputting the second audio soundscape includes outputting the second audio soundscape with a second set of two or more audio components selected randomly or pseudorandomly from the set of available audio components.

In accordance with some embodiments, a computer system is described. The computer system is configured to communicate with a display generation component, an audio generation component, and one or more sensors. The computer system comprises: means for detecting, at a first time, via the one or more sensors, a request to initiate a user experience session of a respective type in an XR environment; means for, in response to detecting the request to initiate the user experience session in the XR environment, initiating a first user experience session of the respective type in the XR environment, including: means for displaying, via the display generation component, a user interface for the first user experience session; and means for outputting, via the audio generation component, a first audio soundscape for the first user experience session, wherein the first audio soundscape is output concurrently with displaying the user interface for the first user experience session and outputting the first audio soundscape includes outputting the first audio soundscape with a first set of two or more audio components selected randomly or pseudorandomly from a set of available audio components; means for detecting, at a second time that is different from the first time, via the one or more sensors, a request to initiate a user experience session of the respective type in an XR environment; and means for, in response to detecting the request to initiate the user experience session in the XR environment, initiating a second user experience session of the respective type in the XR environment, including: means for displaying, via the display generation component, a user interface for the second user experience session; and means for outputting, via the audio generation component, a second audio soundscape for the second user experience session, wherein the second audio soundscape is output concurrently with displaying the user interface for the second user experience session and outputting the second audio soundscape includes outputting the second audio soundscape with a second set of two or more audio components selected randomly or pseudorandomly from the set of available audio components.

In accordance with some embodiments, a computer program product is described. The computer program product comprises one or more programs configured to be executed by one or more processors of a computer system that is in communication with a display generation component, an audio generation component, and one or more sensors, the one or more programs including instructions for: detecting, at a first time, via the one or more sensors, a request to initiate a user experience session of a respective type in an XR environment; in response to detecting the request to initiate the user experience session in the XR environment, initiating a first user experience session of the respective type in the XR environment, including: displaying, via the display generation component, a user interface for the first user experience session; and outputting, via the audio generation component, a first audio soundscape for the first user experience session, wherein the first audio soundscape is output concurrently with displaying the user interface for the first user experience session and outputting the first audio soundscape includes outputting the first audio soundscape with a first set of two or more audio components selected randomly or pseudorandomly from a set of available audio components; detecting, at a second time that is different from the first time, via the one or more sensors, a request to initiate a user experience session of the respective type in an XR environment; and in response to detecting the request to initiate the user experience session in the XR environment, initiating a second user experience session of the respective type in the XR environment, including: displaying, via the display generation component, a user interface for the second user experience session; and outputting, via the audio generation component, a second audio soundscape for the second user experience session, wherein the second audio soundscape is output concurrently with displaying the user interface for the second user experience session and outputting the second audio soundscape includes outputting the second audio soundscape with a second set of two or more audio components selected randomly or pseudorandomly from the set of available audio components.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures.

FIG. 8 is a flow diagram of methods of providing a computer-generated user experience session with particles that move based on breathing characteristics of a user, in accordance with various embodiments.

FIG. 9 is a flow diagram of methods of providing a computer-generated user experience session with options selected based on characteristics of an XR environment, in accordance with various embodiments.

FIGS. 10A-10B are a flow diagram of methods of providing a computer-generated user experience session with a soundscape having randomly selected curated sound components, in accordance with various embodiments.

DESCRIPTION OF EMBODIMENTS

Figure 1:
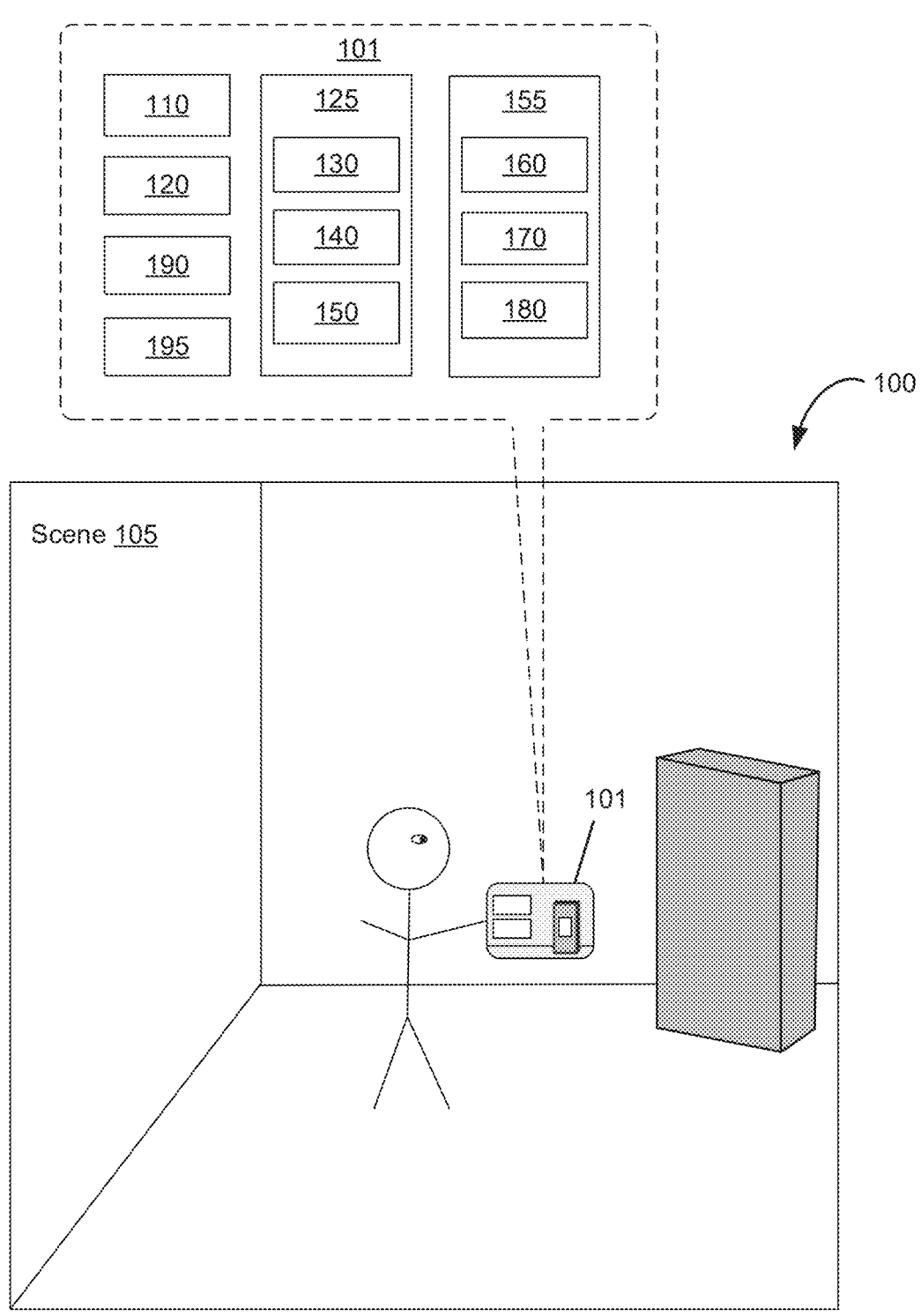
FIG. 1 is a block diagram illustrating an operating environment of a computer system for providing XR experiences in accordance with some embodiments.

The present disclosure relates to user interfaces for providing an extended reality (XR) experience to a user, in accordance with some embodiments.

The systems, methods, and GUIs described herein improve user interface interactions with virtual/augmented reality environments in multiple ways.

In some embodiments, a computer system provides a computer-generated user experience session with particles that move based on breathing characteristics of a user. The computer system displays a user interface for a user experience session. When the user experience session is active, the computer system detects one or more breathing characteristics of the user of the computer system and displays a user interface object having a plurality of particles that move based on the one or more breathing characteristics of the user. When a first breathing event of the user satisfies a first set of criteria, the computer system displays the particles of the user interface object moving in a first manner during the first breathing event of the user. When the first breathing event of the user satisfies a second set of criteria, the computer system displays the particles of the user interface object moving in a second manner different from the first manner during the first breathing event of the user.

In some embodiments, a computer system provides a computer-generated user experience session with options selected based on characteristics of an XR environment. While the computer system displays an XR environment having one or more characteristics, it detects a request to initiate a user experience session in the XR environment. In response to detecting the request to initiate the user experience session in the XR environment, the computer system initiates the user experience session in the XR environment, including displaying a user interface for the user experience session. When the one or more characteristics of the XR environment satisfy a first set of criteria, the computer system displays the user interface for the user experience session with a first set of one or more options enabled for the user experience session. When the one or more characteristics of the XR environment satisfy a second set of criteria different from the first set of criteria, the computer system displays the user interface for the user experience session with a second set of one or more options enabled for the user experience session, wherein the second set of one or more options are different from the first set of one or more options.

In some embodiments, a computer system provides a computer-generated user experience session with a soundscape having randomly selected curated sound components. The computer system detects, at a first time, a request to initiate a user experience session of a respective type in an XR environment. In response to detecting the request to initiate the user experience session in the XR environment, the computer system initiates a first user experience session of the respective type in the XR environment. Initiating the first user experience session includes displaying a user interface for the first user experience session, and outputting a first audio soundscape for the first user experience session. The first audio soundscape is output concurrently with displaying the user interface for the first user experience session. Outputting the first audio soundscape includes outputting the first audio soundscape with a first set of two or more audio components selected randomly or pseudo-randomly from a set of available audio components. The computer system detects, at a second time that is different from the first time, a request to initiate a user experience session of the respective type in an XR environment. In response to detecting the request to initiate the user experience session in the XR environment, the computer system initiates a second user experience session of the respective type in the XR environment. Initiating the second user experience session includes displaying a user interface for the second user experience session, and outputting a second audio soundscape for the second user experience session. The second audio soundscape is output concurrently with displaying the user interface for the second user experience session. Outputting the second audio soundscape includes outputting the second audio soundscape with a second set of two or more audio components selected randomly or pseudorandomly from the set of available audio components.

FIGS. 1-6 provide a description of example computer systems for providing XR experiences to users. FIGS. 7A-7L illustrate example techniques for providing computer-generated user experience sessions in an extended reality environment, in accordance with some embodiments. FIG. 8 is a flow diagram of methods of providing a computer-generated user experience session with particles that move based on breathing characteristics of a user, in accordance with various embodiments. FIG. 9 is a flow diagram of methods of providing a computer-generated user experience session with options selected based on characteristics of an XR environment, in accordance with various embodiments. FIGS. 10A-10B are a flow diagram of methods of providing a computer-generated user experience session with a soundscape having randomly selected curated sound components, in accordance with various embodiments. The user interfaces in FIGS. 7A-7L are used to illustrate the processes in FIGS. 8, 9, 10A, and 10B.

The processes described below enhance the operability of the devices and make the user-device interfaces more efficient (e.g., by helping the user to provide proper inputs and reducing user mistakes when operating/interacting with the device) through various techniques, including by providing improved visual feedback to the user, reducing the number of inputs needed to perform an operation, providing additional control options without cluttering the user interface with additional displayed controls, performing an operation when a set of conditions has been met without requiring further user input, improving privacy and/or security, providing a more varied, detailed, and/or realistic user experience while saving storage space, and/or additional techniques. These techniques also reduce power usage and improve battery life of the device by enabling the user to use the device more quickly and efficiently. Saving on battery power, and thus weight, improves the ergonomics of the device. These techniques also enable real-time communication, allow for the use of fewer and/or less precise sensors resulting in a more compact, lighter, and cheaper device, and enable the device to be used in a variety of lighting conditions. These techniques reduce energy usage, thereby reducing heat emitted by the device, which is particularly important for a wearable device where a device well within operational parameters for device components can become uncomfortable for a user to wear if it is producing too much heat.

The processes described below enhance the operability of the devices and make the user-device interfaces more efficient by providing a more varied, detailed, and/or realistic user experience while saving storage space. For example, the techniques allow a device (e.g., a computer system, tablet, and/or HMD) to provide the user experience while saving space by reducing the amount of visual and/or audio components that are required to be stored to generate user experience sessions. For example, in some embodiments, the device stores a superset of audio characteristics from which the device can select (randomly or pseudorandomly) various combinations of the audio characteristics to create respective soundscapes for user experience sessions. This technique saves space because the device is able to generate many different soundscapes from the subset of audio characteristics without having to store fully assembled soundscapes for the user experience sessions. Similarly, the device stores a superset of visual characteristics from which the device can select (randomly or pseudorandomly) various combinations of the visual characteristics to create visual components and visual effects for user experience sessions. This technique saves space because the device is able to generate many different visuals from the subset of visual characteristics without having to store fully rendered visual components for the user experience sessions. Additional examples illustrating these techniques are described below with reference to the figures.

In addition, in methods described herein where one or more steps are contingent upon one or more conditions having been met, it should be understood that the described method can be repeated in multiple repetitions so that over the course of the repetitions all of the conditions upon which steps in the method are contingent have been met in different repetitions of the method. For example, if a method requires performing a first step if a condition is satisfied, and a second step if the condition is not satisfied, then a person of ordinary skill would appreciate that the claimed steps are repeated until the condition has been both satisfied and not satisfied, in no particular order. Thus, a method described with one or more steps that are contingent upon one or more conditions having been met could be rewritten as a method that is repeated until each of the conditions described in the method has been met. This, however, is not required of system or computer readable medium claims where the system or computer readable medium contains instructions for performing the contingent operations based on the satisfaction of the corresponding one or more conditions and thus is capable of determining whether the contingency has or has not been satisfied without explicitly repeating steps of a method until all of the conditions upon which steps in the method are contingent have been met. A person having ordinary skill in the art would also understand that, similar to a method with contingent steps, a system or computer readable storage medium can repeat the steps of a method as many times as are needed to ensure that all of the contingent steps have been performed.

In some embodiments, as shown in FIG. 1, the XR experience is provided to the user via an operating environment 100 that includes a computer system 101. The computer system 101 includes a controller 110 (e.g., processors of a portable electronic device or a remote server), a display generation component 120 (e.g., a head-mounted device (HMD), a display, a projector, a touch-screen, etc.), one or more input devices 125 (e.g., an eye tracking device 130, a hand tracking device 140, other input devices 150), one or more output devices 155 (e.g., speakers 160, tactile output generators 170, and other output devices 180), one or more sensors 190 (e.g., image sensors, light sensors, depth sensors, tactile sensors, orientation sensors, proximity sensors, temperature sensors, location sensors, motion sensors, velocity sensors, speed sensors, etc.), and optionally one or more peripheral devices 195 (e.g., home appliances, wearable devices, etc.). In some embodiments, one or more of the input devices 125, output devices 155, sensors 190, and peripheral devices 195 are integrated with the display generation component 120 (e.g., in a head-mounted device or a handheld device).

When describing a XR experience, various terms are used to differentially refer to several related but distinct environments that the user may sense and/or with which a user may interact (e.g., with inputs detected by a computer system 101 generating the XR experience that cause the computer system generating the XR experience to generate audio, visual, and/or tactile feedback corresponding to various inputs provided to the computer system 101). The following is a subset of these terms:

Physical environment: A physical environment refers to a physical world that people can sense and/or interact with without aid of electronic systems. Physical environments, such as a physical park, include physical articles, such as physical trees, physical buildings, and physical people. People can directly sense and/or interact with the physical environment, such as through sight, touch, hearing, taste, and smell.

Extended reality: In contrast, an extended reality (XR) environment refers to a wholly or partially simulated environment that people sense and/or interact with via an electronic system. In XR, a subset of a person's physical motions, or representations thereof, are tracked, and, in response, one or more characteristics of one or more virtual objects simulated in the XR environment are adjusted in a manner that comports with at least one law of physics. For example, a XR system may detect a person's head turning and, in response, adjust graphical content and an acoustic field presented to the person in a manner similar to how such views and sounds would change in a physical environment. In some situations (e.g., for accessibility reasons), adjustments to characteristic(s) of virtual object(s) in a XR environment may be made in response to representations of physical motions (e.g., vocal commands). A person may sense and/or interact with a XR object using any one of their senses, including sight, sound, touch, taste, and smell. For example, a person may sense and/or interact with audio objects that create a 3D or spatial audio environment that provides the perception of point audio sources in 3D space. In another example, audio objects may enable audio transparency, which selectively incorporates ambient sounds from the physical environment with or without computer-generated audio. In some XR environments, a person may sense and/or interact only with audio objects.

Examples of XR include virtual reality and mixed reality.

Virtual reality: A virtual reality (VR) environment refers to a simulated environment that is designed to be based entirely on computer-generated sensory inputs for one or more senses. A VR environment comprises a plurality of virtual objects with which a person may sense and/or interact. For example, computer-generated imagery of trees, buildings, and avatars representing people are examples of virtual objects. A person may sense and/or interact with virtual objects in the VR environment through a simulation of the person's presence within the computer-generated environment, and/or through a simulation of a subset of the person's physical movements within the computer-generated environment.

Mixed reality: In contrast to a VR environment, which is designed to be based entirely on computer-generated sensory inputs, a mixed reality (MR) environment refers to a simulated environment that is designed to incorporate sensory inputs from the physical environment, or a representation thereof, in addition to including computer-generated sensory inputs (e.g., virtual objects). On a virtuality continuum, a mixed reality environment is anywhere between, but not including, a wholly physical environment at one end and virtual reality environment at the other end. In some MR environments, computer-generated sensory inputs may respond to changes in sensory inputs from the physical environment. Also, some electronic systems for presenting an MR environment may track location and/or orientation with respect to the physical environment to enable virtual objects to interact with real objects (that is, physical articles from the physical environment or representations thereof). For example, a system may account for movements so that a virtual tree appears stationary with respect to the physical ground.

Examples of mixed realities include augmented reality and augmented virtuality. Augmented reality: An augmented reality (AR) environment refers to a simulated environment in which one or more virtual objects are superimposed over a physical environment, or a representation thereof. For example, an electronic system for presenting an AR environment may have a transparent or translucent display through which a person may directly view the physical environment. The system may be configured to present virtual objects on the transparent or translucent display, so that a person, using the system, perceives the virtual objects superimposed over the physical environment. Alternatively, a system may have an opaque display and one or more imaging sensors that capture images or video of the physical environment, which are representations of the physical environment. The system composites the images or video with virtual objects, and presents the composition on the opaque display. A person, using the system, indirectly views the physical environment by way of the images or video of the physical environment, and perceives the virtual objects superimposed over the physical environment. As used herein, a video of the physical environment shown on an opaque display is called "pass-through video," meaning a system uses one or more image sensor(s) to capture images of the physical environment, and uses those images in presenting the AR environment on the opaque display. Further alternatively, a system may have a projection system that projects virtual objects into the physical environment, for example, as a hologram or on a physical surface, so that a person, using the system, perceives the virtual objects superimposed over the physical environment. An augmented reality environment also refers to a simulated environment in which a representation of a physical environment is transformed by computer-generated sensory information. For example, in providing pass-through video, a system may transform one or more sensor images to impose a select perspective (e.g., viewpoint) different than the perspective captured by the imaging sensors. As another example, a representation of a physical environment may be transformed by graphically modifying (e.g., enlarging) portions thereof, such that the modified portion may be representative but not photorealistic versions of the originally captured images. As a further example, a representation of a physical environment may be transformed by graphically eliminating or obfuscating portions thereof.

Augmented virtuality: An augmented virtuality (AV) environment refers to a simulated environment in which a virtual or computer-generated environment incorporates one or more sensory inputs from the physical environment. The sensory inputs may be representations of one or more characteristics of the physical environment. For example, an AV park may have virtual trees and virtual buildings, but people with faces photorealistically reproduced from images taken of physical people. As another example, a virtual object may adopt a shape or color of a physical article imaged by one or more imaging sensors. As a further example, a virtual object may adopt shadows consistent with the position of the sun in the physical environment.

Viewpoint-locked virtual object: A virtual object is viewpoint-locked when a computer system displays the virtual object at the same location and/or position in the viewpoint of the user, even as the viewpoint of the user shifts (e.g., changes). In embodiments where the computer system is a head-mounted device, the viewpoint of the user is locked to the forward facing direction of the user's head (e.g., the viewpoint of the user is at least a portion of the field-of-view of the user when the user is looking straight ahead); thus, the viewpoint of the user remains fixed even as the user's gaze is shifted, without moving the user's head. In embodiments where the computer system has a display generation component (e.g., a display screen) that can be repositioned with respect to the user's head, the viewpoint of the user is the augmented reality view that is being presented to the user on a display generation component of the computer system. For example, a viewpoint-locked virtual object that is displayed in the upper left corner of the viewpoint of the user, when the viewpoint of the user is in a first orientation (e.g., with the user's head facing north) continues to be displayed in the upper left corner of the viewpoint of the user, even as the viewpoint of the user changes to a second orientation (e.g., with the user's head facing west). In other words, the location and/or position at which the viewpoint-locked virtual object is displayed in the viewpoint of the user is independent of the user's position and/or orientation in the physical environment. In embodiments in which the computer system is a head-mounted device, the viewpoint of the user is locked to the orientation of the user's head, such that the virtual object is also referred to as a "head-locked virtual object."

Environment-locked virtual object: A virtual object is environment-locked (alternatively, "world-locked") when a computer system displays the virtual object at a location and/or position in the viewpoint of the user that is based on (e.g., selected in reference to and/or anchored to) a location and/or object in the three-dimensional environment (e.g., a physical environment or a virtual environment). As the viewpoint of the user shifts, the location and/or object in the environment relative to the viewpoint of the user changes, which results in the environment-locked virtual object being displayed at a different location and/or position in the viewpoint of the user. For example, an environment-locked virtual object that is locked onto a tree that is immediately in front of a user is displayed at the center of the viewpoint of the user. When the viewpoint of the user shifts to the right (e.g., the user's head is turned to the right) so that the tree is now left-of-center in the viewpoint of the user (e.g., the tree's position in the viewpoint of the user shifts), the environment-locked virtual object that is locked onto the tree is displayed left-of-center in the viewpoint of the user. In other words, the location and/or position at which the environment-locked virtual object is displayed in the viewpoint of the user is dependent on the position and/or orientation of the location and/or object in the environment onto which the virtual object is locked. In some embodiments, the computer system uses a stationary frame of reference (e.g., a coordinate system that is anchored to a fixed location and/or object in the physical environment) in order to determine the position at which to display an environment-locked virtual object in the viewpoint of the user. An environment-locked virtual object can be locked to a stationary part of the environment (e.g., a floor, wall, table, or other stationary object) or can be locked to a moveable part of the environment (e.g., a vehicle, animal, person, or even a representation of portion of the users body that moves independently of a viewpoint of the user, such as a user's hand, wrist, arm, or foot) so that the virtual object is moved as the viewpoint or the portion of the environment moves to maintain a fixed relationship between the virtual object and the portion of the environment.

In some embodiments a virtual object that is environment-locked or viewpoint-locked exhibits lazy follow behavior which reduces or delays motion of the environment-locked or viewpoint-locked virtual object relative to movement of a point of reference which the virtual object is following. In some embodiments, when exhibiting lazy follow behavior the computer system intentionally delays movement of the virtual object when detecting movement of a point of reference (e.g., a portion of the environment, the viewpoint, or a point that is fixed relative to the viewpoint, such as a point that is between 5-300 cm from the viewpoint) which the virtual object is following. For example, when the point of reference (e.g., the portion of the environment or the viewpoint) moves with a first speed, the virtual object is moved by the device to remain locked to the point of reference but moves with a second speed that is slower than the first speed (e.g., until the point of reference stops moving or slows down, at which point the virtual object starts to catch up to the point of reference). In some embodiments, when a virtual object exhibits lazy follow behavior the device ignores small amounts of movement of the point of reference (e.g., ignoring movement of the point of reference that is below a threshold amount of movement such as movement by 0-5 degrees or movement by 0-50 cm). For example, when the point of reference (e.g., the portion of the environment or the viewpoint to which the virtual object is locked) moves by a first amount, a distance between the point of reference and the virtual object increases (e.g., because the virtual object is being displayed so as to maintain a fixed or substantially fixed position relative to a viewpoint or portion of the environment that is different from the point of reference to which the virtual object is locked) and when the point of reference (e.g., the portion of the environment or the viewpoint to which the virtual object is locked) moves by a second amount that is greater than the first amount, a distance between the point of reference and the virtual object initially increases (e.g., because the virtual object is being displayed so as to maintain a fixed or substantially fixed position relative to a viewpoint or portion of the environment that is different from the point of reference to which the virtual object is locked) and then decreases as the amount of movement of the point of reference increases above a threshold (e.g., a "lazy follow" threshold) because the virtual object is moved by the computer system to maintain a fixed or substantially fixed position relative to the point of reference. In some embodiments the virtual object maintaining a substantially fixed position relative to the point of reference includes the virtual object being displayed within a threshold distance (e.g., 1, 2, 3, 5, 15, 20, 50 cm) of the point of reference in one or more dimensions (e.g., up/down, left/right, and/or forward/backward relative to the position of the point of reference).

In some embodiments, spatial media includes spatial visual media and/or spatial audio. In some embodiments, a spatial capture is a capture of spatial media. In some embodiments, spatial visual media (also referred to as stereoscopic media) (e.g., a spatial image and/or a spatial video) is media that includes two different images or sets of images, representing two perspectives of the same or overlapping fields-of-view, for concurrent display. A first image representing a first perspective is presented to a first eye of the viewer and a second image representing a second perspective, different from the first perspective, is concurrently presented to a second eye of the viewer. The first image and the second image have the same or overlapping fields-of-view. In some embodiments, a computer system displays the first image via a first display that is positioned for viewing by the first eye of the viewer and concurrently displays the second image via a second display, different from the first display, that is position for viewing by the second eye of the viewer. In some embodiments, the first image and the second image, when viewed together, create a depth effect and provide the viewer with depth perception for the contents of the images. In some embodiments, a first video representing a first perspective is presented to a first eye of the viewer and a second video representing a second perspective, different from the first perspective, is concurrently presented to a second eye of the viewer. The first video and the second video have the same or overlapping fields-of-view. In some embodiments, the first video and the second video, when viewed together, create a depth effect and provide the viewer with depth perception for the contents of the videos. In some embodiments, spatial audio experiences in headphones are produced by manipulating sounds in the headphone's two audio channels (e.g., left and right) so that they resemble directional sounds arriving in the ear-canal. For example, the headphones can reproduce a spatial audio signal that simulates a soundscape around the listener (also referred to as the user). An effective spatial sound reproduction can render sounds such that the listener perceives the sound as coming from a location within the soundscape external to the listener's head, just as the listener would experience the sound if encountered in the real world.

The geometry of the listener's ear, and in particular the outer ear (pinna), has a significant effect on the sound that arrives from a sound source to a listener's eardrum. The spatial audio sound experience is possible by taking into account the effect of the listener's pinna, the listener's head, and/or the listener's torso to the sound that enters to the listener's ear-canal. The geometry of the user's ear is optionally determined by using a three-dimensional scanning device that produces a three-dimensional model of at least a portion of the visible parts of the user's ear. This geometry is optionally used to produce a filter for producing the spatial audio experience. In some embodiments, spatial audio is audio that has been filtered such that a listener of the audio perceives the audio as coming from one or more directions and/or locations in three-dimensional space (e.g., from above, below, and/or in front of the listener).

An example of such a filter is a Head-Related Transfer Function (HRTF) filter. These filters are used to provide an effect that is similar to how a human ear, head, and torso filter sounds. When the geometry of the ears of a listener is known, a personalized filter (e.g., a personalized HRTF filter) can be produced so that the sound experienced by that listener through headphones (e.g., in-ear headphones, on-ear headphones, and/or over-ear headphones) is more realistic. In some embodiments, two filters are produced-one filter per ear-so that each ear of the listener has a corresponding personalized filter (e.g., personalized HRTF filter), as the ears of the listener may be of different geometry.

In some embodiments, a HRTF filter includes some (or all) acoustic information required to describe how sound reflects or diffracts around a listener's head before entering the listener's auditory system. In some embodiments, a personalized HRTF filter can be selected from a database of previously determined HRTFs for users having similar anatomical characteristics. In some embodiments, a personalized HRTF filter can be generated by numerical modeling based on the geometry of the listener's ear. One or more processors of the computer system optionally apply the personalized HRTF filter for the listener to an audio input signal to generate a spatial input signal for playback by headphones that are connected (e.g., wirelessly or by wire) to the computer system.

Hardware: There are many different types of electronic systems that enable a person to sense and/or interact with various XR environments. Examples include head-mounted systems, projection-based systems, heads-up displays (HUDs), vehicle windshields having integrated display capability, windows having integrated display capability, displays formed as lenses designed to be placed on a person's eyes (e.g., similar to contact lenses), headphones/earphones, speaker arrays, input systems (e.g., wearable or handheld controllers with or without haptic feedback), smartphones, tablets, and desktop/laptop computers. A head-mounted system may include speakers and/or other audio output devices integrated into the head-mounted system for providing audio output. A head-mounted system may have one or more speaker(s) and an integrated opaque display. Alternatively, a head-mounted system may be configured to accept an external opaque display (e.g., a smartphone). The head-mounted system may incorporate one or more imaging sensors to capture images or video of the physical environment, and/or one or more microphones to capture audio of the physical environment. Rather than an opaque display, a head-mounted system may have a transparent or translucent display. The transparent or translucent display may have a medium through which light representative of images is directed to a person's eyes. The display may utilize digital light projection, OLEDs, LEDs, uLEDs, liquid crystal on silicon, laser scanning light source, or any combination of these technologies. The medium may be an optical waveguide, a hologram medium, an optical combiner, an optical reflector, or any combination thereof. In one embodiment, the transparent or translucent display may be configured to become opaque selectively. Projection-based systems may employ retinal projection technology that projects graphical images onto a person's retina. Projection systems also may be configured to project virtual objects into the physical environment, for example, as a hologram or on a physical surface. In some embodiments, the controller 110 is configured to manage and coordinate a XR experience for the user. In some embodiments, the controller 110 includes a suitable combination of software, firmware, and/or hardware. The controller 110 is described in greater detail below with respect to FIG. 2. In some embodiments, the controller 110 is a computing device that is local or remote relative to the scene 105 (e.g., a physical environment). For example, the controller 110 is a local server located within the scene 105. In another example, the controller 110 is a remote server located outside of the scene 105 (e.g., a cloud server, central server, etc.). In some embodiments, the controller 110 is communicatively coupled with the display generation component 120 (e.g., an HMD, a display, a projector, a touchscreen, etc.) via one or more wired or wireless communication channels 144 (e.g., BLUETOOTH, IEEE 802.11x, IEEE 802.16x, IEEE 802.3x, etc.). In another example, the controller 110 is included within the enclosure (e.g., a physical housing) of the display generation component 120 (e.g., an HMD, or a portable electronic device that includes a display and one or more processors, etc.), one or more of the input devices 125, one or more of the output devices 155, one or more of the sensors 190, and/or one or more of the peripheral devices 195, or share the same physical enclosure or support structure with one or more of the above.

In some embodiments, the display generation component 120 is configured to provide the XR experience (e.g., at least a visual component of the XR experience) to the user. In some embodiments, the display generation component 120 includes a suitable combination of software, firmware, and/or hardware. The display generation component 120 is described in greater detail below with respect to FIG. 3. In some embodiments, the functionalities of the controller 110 are provided by and/or combined with the display generation component 120.

According to some embodiments, the display generation component 120 provides a XR experience to the user while the user is virtually and/or physically present within the scene 105.

In some embodiments, the display generation component is worn on a part of the user's body (e.g., on his/her head, on his/her hand, etc.). As such, the display generation component 120 includes one or more XR displays provided to display the XR content. For example, in various embodiments, the display generation component 120 encloses the field-of-view of the user. In some embodiments, the display generation component 120 is a handheld device (such as a smartphone or tablet) configured to present XR content, and the user holds the device with a display directed towards the field-of-view of the user and a camera directed towards the scene 105. In some embodiments, the handheld device is optionally placed within an enclosure that is worn on the head of the user. In some embodiments, the handheld device is optionally placed on a support (e.g., a tripod) in front of the user. In some embodiments, the display generation component 120 is a XR chamber, enclosure, or room configured to present XR content in which the user does not wear or hold the display generation component 120. Many user interfaces described with reference to one type of hardware for displaying XR content (e.g., a handheld device or a device on a tripod) could be implemented on another type of hardware for displaying XR content (e.g., an HMD or other wearable computing device). For example, a user interface showing interactions with XR content triggered based on interactions that happen in a space in front of a handheld or tripod mounted device could similarly be implemented with an HMD where the interactions happen in a space in front of the HMD and the responses of the XR content are displayed via the HMD. Similarly, a user interface showing interactions with XR content triggered based on movement of a handheld or tripod mounted device relative to the physical environment (e.g., the scene 105 or a part of the user's body (e.g., the user's eye(s), head, or hand)) could similarly be implemented with an HMD where the movement is caused by movement of the HMD relative to the physical environment (e.g., the scene 105 or a part of the user's body (e.g., the user's eye(s), head, or hand)).

While pertinent features of the operating environment 100 are shown in FIG. 1, those of ordinary skill in the art will appreciate from the present disclosure that various other features have not been illustrated for the sake of brevity and so as not to obscure more pertinent aspects of the example embodiments disclosed herein.

Figure 2:
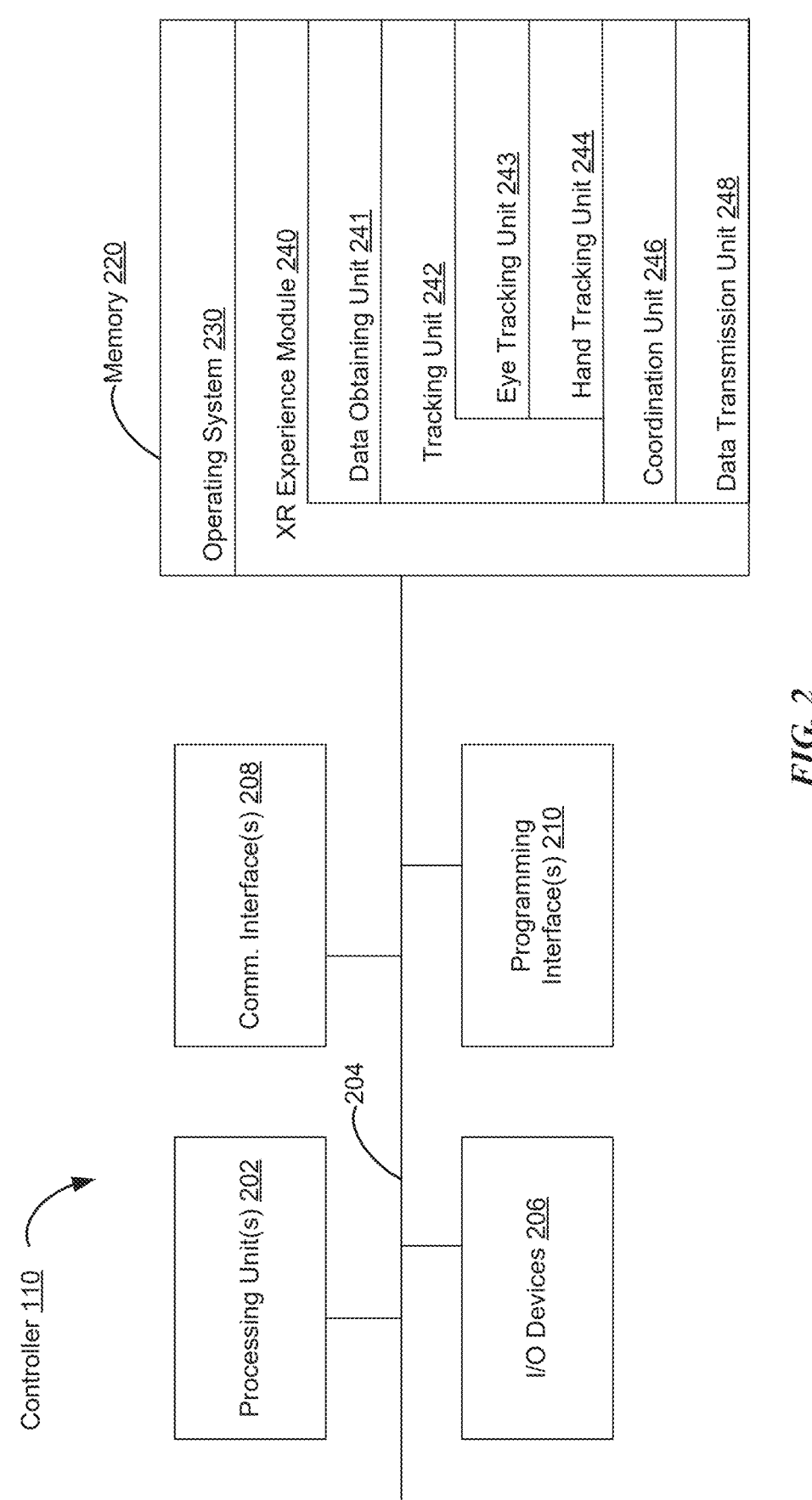
FIG. 2 is a block diagram illustrating a controller of a computer system that is configured to manage and coordinate a XR experience for the user in accordance with some embodiments.

FIG. 2 is a block diagram of an example of the controller 110 in some embodiments. While certain specific features are illustrated, those skilled in the art will appreciate from the present disclosure that various other features have not been illustrated for the sake of brevity, and so as not to obscure more pertinent aspects of the embodiments disclosed herein. To that end, as a non-limiting example, in some embodiments the controller 110 includes one or more processing units 202 (e.g., microprocessors, application-specific integrated-circuits (ASICs), field-programmable gate arrays (FPGAs), graphics processing units (GPUs), central processing units (CPUs), processing cores, and/or the like), one or more input/output (I/O) devices 206, one or more communication interfaces 208 (e.g., universal serial bus (USB), FIREWIRE, THUNDERBOLT, IEEE 802.3x, IEEE 802.11x, IEEE 802.16x, global system for mobile communications (GSM), code division multiple access (CDMA), time division multiple access (TDMA), global positioning system (GPS), infrared (IR), BLUETOOTH, ZIGBEE, and/or the like type interface), one or more programming (e.g., I/O) interfaces 210, a memory 220, and one or more communication buses 204 for interconnecting these and various other components.

In some embodiments, the one or more communication buses 204 include circuitry that interconnects and controls communications between system components. In some embodiments, the one or more I/O devices 206 include at least one of a keyboard, a mouse, a touchpad, a joystick, one or more microphones, one or more speakers, one or more image sensors, one or more displays, and/or the like.

The memory 220 includes high-speed random-access memory, such as dynamic random-access memory (DRAM), static random-access memory (SRAM), double-data-rate random-access memory (DDR RAM), or other random-access solid-state memory devices. In some embodiments, the memory 220 includes non-volatile memory, such as one or more magnetic disk storage devices, optical disk storage devices, flash memory devices, or other non-volatile solid-state storage devices. The memory 220 optionally includes one or more storage devices remotely located from the one or more processing units 202. The memory 220 comprises a non-transitory computer readable storage medium. In some embodiments, the memory 220 or the non-transitory computer readable storage medium of the memory 220 stores the following programs, modules and data structures, or a subset thereof including an optional operating system 230 and a XR experience module 240.

The operating system 230 includes instructions for handling various basic system services and for performing hardware dependent tasks. In some embodiments, the XR experience module 240 is configured to manage and coordinate one or more XR experiences for one or more users (e.g., a single XR experience for one or more users, or multiple XR experiences for respective groups of one or more users). To that end, in various embodiments, the XR experience module 240 includes a data obtaining unit 241, a tracking unit 242, a coordination unit 246, and a data transmitting unit 248.

In some embodiments, the data obtaining unit 241 is configured to obtain data (e.g., presentation data, interaction data, sensor data, location data, etc.) from at least the display generation component 120 of FIG. 1, and optionally one or more of the input devices 125, output devices 155, sensors 190, and/or peripheral devices 195. To that end, in various embodiments, the data obtaining unit 241 includes instructions and/or logic therefor, and heuristics and metadata therefor.

In some embodiments, the tracking unit 242 is configured to map the scene 105 and to track the position/location of at least the display generation component 120 with respect to the scene 105 of FIG. 1, and optionally, to one or more of the input devices 125, output devices 155, sensors 190, and/or peripheral devices 195. To that end, in various embodiments, the tracking unit 242 includes instructions and/or logic therefor, and heuristics and metadata therefor. In some embodiments, the tracking unit 242 includes hand tracking unit 244 and/or eye tracking unit 243. In some embodiments, the hand tracking unit 244 is configured to track the position/location of one or more portions of the user's hands, and/or motions of one or more portions of the user's hands with respect to the scene 105 of FIG. 1, relative to the display generation component 120, and/or relative to a coordinate system defined relative to the user's hand. The hand tracking unit 244 is described in greater detail below with respect to FIG. 4. In some embodiments, the eye tracking unit 243 is configured to track the position and movement of the user's gaze (or more broadly, the user's eyes, face, or head) with respect to the scene 105 (e.g., with respect to the physical environment and/or to the user (e.g., the user's hand)) or with respect to the XR content displayed via the display generation component 120. The eye tracking unit 243 is described in greater detail below with respect to FIG. 5.

In some embodiments, the coordination unit 246 is configured to manage and coordinate the XR experience presented to the user by the display generation component 120, and optionally, by one or more of the output devices 155 and/or peripheral devices 195. To that end, in various embodiments, the coordination unit 246 includes instructions and/or logic therefor, and heuristics and metadata therefor.

In some embodiments, the data transmitting unit 248 is configured to transmit data (e.g., presentation data, location data, etc.) to at least the display generation component 120, and optionally, to one or more of the input devices 125, output devices 155, sensors 190, and/or peripheral devices 195. To that end, in various embodiments, the data transmitting unit 248 includes instructions and/or logic therefor, and heuristics and metadata therefor.

Although the data obtaining unit 241, the tracking unit 242 (e.g., including the eye tracking unit 243 and the hand tracking unit 244), the coordination unit 246, and the data transmitting unit 248 are shown as residing on a single device (e.g., the controller 110), it should be understood that in other embodiments, any combination of the data obtaining unit 241, the tracking unit 242 (e.g., including the eye tracking unit 243 and the hand tracking unit 244), the coordination unit 246, and the data transmitting unit 248 may be located in separate computing devices.

Moreover, FIG. 2 is intended more as functional description of the various features that may be present in a particular implementation as opposed to a structural schematic of the embodiments described herein. As recognized by those of ordinary skill in the art, items shown separately could be combined and some items could be separated. For example, some functional modules shown separately in FIG. 2 could be implemented in a single module and the various functions of single functional blocks could be implemented by one or more functional blocks in various embodiments. The actual number of modules and the division of particular functions and how features are allocated among them will vary from one implementation to another and, in some embodiments, depends in part on the particular combination of hardware, software, and/or firmware chosen for a particular implementation.

Figure 3:
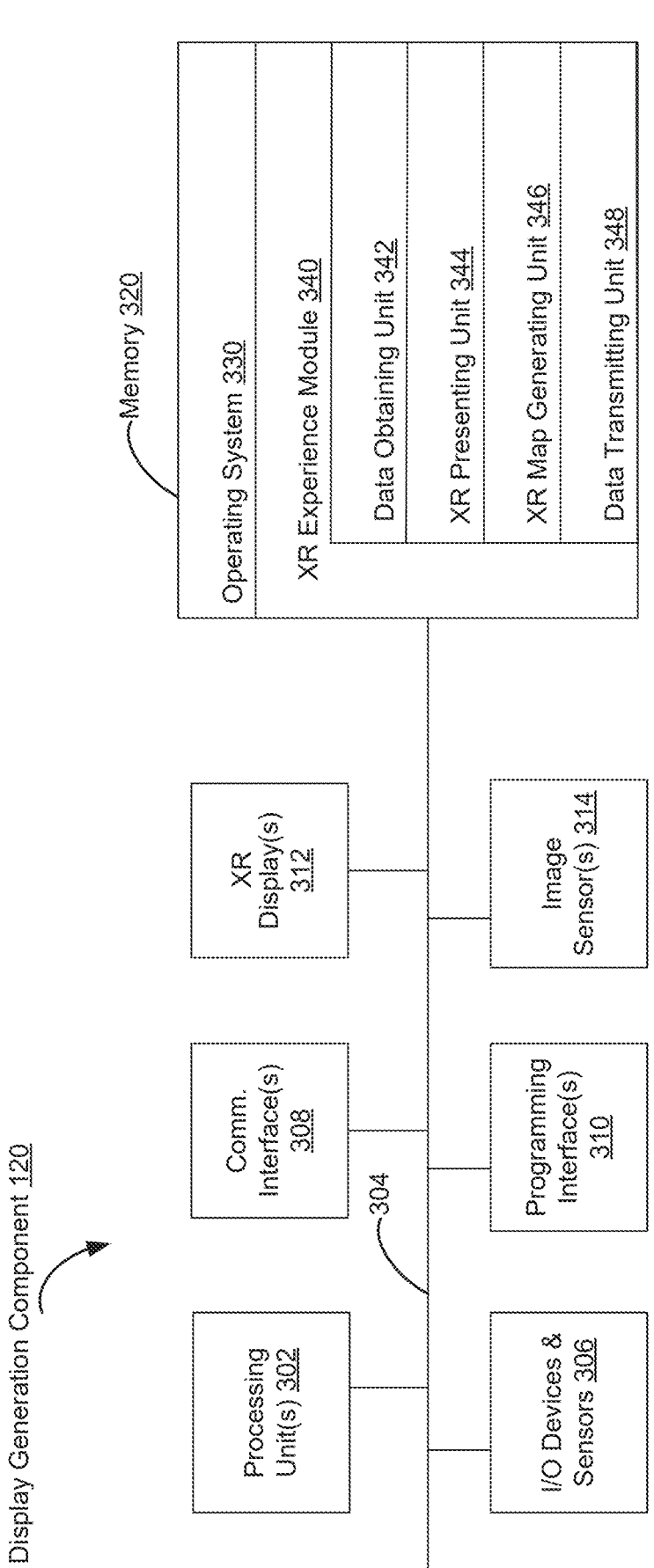
FIG. 3 is a block diagram illustrating a display generation component of a computer system that is configured to provide a visual component of the XR experience to the user in accordance with some embodiments.

FIG. 3 is a block diagram of an example of the display generation component 120 in some embodiments. While certain specific features are illustrated, those skilled in the art will appreciate from the present disclosure that various other features have not been illustrated for the sake of brevity, and so as not to obscure more pertinent aspects of the embodiments disclosed herein. To that end, as a non-limiting example, in some embodiments the display generation component 120 (e.g., HMD) includes one or more processing units 302 (e.g., microprocessors, ASICs, FPGAs, GPUs, CPUs, processing cores, and/or the like), one or more input/output (I/O) devices and sensors 306, one or more communication interfaces 308 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, and/or the like type interface), one or more programming (e.g., I/O) interfaces 310, one or more XR displays 312, one or more optional interior- and/or exterior-facing image sensors 314, a memory 320, and one or more communication buses 304 for interconnecting these and various other components.

In some embodiments, the one or more communication buses 304 include circuitry that interconnects and controls communications between system components. In some embodiments, the one or more I/O devices and sensors 306 include at least one of an inertial measurement unit (IMU), an accelerometer, a gyroscope, a thermometer, one or more physiological sensors (e.g., blood pressure monitor, heart rate monitor, blood oxygen sensor, blood glucose sensor, etc.), one or more microphones, one or more speakers, a haptics engine, one or more depth sensors (e.g., a structured light, a time-of-flight, or the like), and/or the like.

In some embodiments, the one or more XR displays 312 are configured to provide the XR experience to the user. In some embodiments, the one or more XR displays 312 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), micro-electro-mechanical system (MEMS), and/or the like display types. In some embodiments, the one or more XR displays 312 correspond to diffractive, reflective, polarized, holographic, etc. waveguide displays. For example, the display generation component 120 (e.g., HMD) includes a single XR display. In another example, the display generation component 120 includes a XR display for each eye of the user. In some embodiments, the one or more XR displays 312 are capable of presenting MR and VR content. In some embodiments, the one or more XR displays 312 are capable of presenting MR or VR content.

In some embodiments, the one or more image sensors 314 are configured to obtain image data that corresponds to at least a portion of the face of the user that includes the eyes of the user (and may be referred to as an eye-tracking camera). In some embodiments, the one or more image sensors 314 are configured to obtain image data that corresponds to at least a portion of the user's hand(s) and optionally arm(s) of the user (and may be referred to as a hand-tracking camera). In some embodiments, the one or more image sensors 314 are configured to be forward-facing so as to obtain image data that corresponds to the scene as would be viewed by the user if the display generation component 120 (e.g., HMD) was not present (and may be referred to as a scene camera). The one or more optional image sensors 314 can include one or more RGB cameras (e.g., with a complimentary metal-oxide-semiconductor (CMOS) image sensor or a charge-coupled device (CCD) image sensor), one or more infrared (IR) cameras, one or more event-based cameras, and/or the like.

The memory 320 includes high-speed random-access memory, such as DRAM, SRAM, DDR RAM, or other random-access solid-state memory devices. In some embodiments, the memory 320 includes non-volatile memory, such as one or more magnetic disk storage devices, optical disk storage devices, flash memory devices, or other non-volatile solid-state storage devices. The memory 320 optionally includes one or more storage devices remotely located from the one or more processing units 302. The memory 320 comprises a non-transitory computer readable storage medium. In some embodiments, the memory 320 or the non-transitory computer readable storage medium of the memory 320 stores the following programs, modules and data structures, or a subset thereof including an optional operating system 330 and a XR presentation module 340.

The operating system 330 includes instructions for handling various basic system services and for performing hardware dependent tasks. In some embodiments, the XR presentation module 340 is configured to present XR content to the user via the one or more XR displays 312. To that end, in various embodiments, the XR presentation module 340 includes a data obtaining unit 342, a XR presenting unit 344, a XR map generating unit 346, and a data transmitting unit 348.

In some embodiments, the data obtaining unit 342 is configured to obtain data (e.g., presentation data, interaction data, sensor data, location data, etc.) from at least the controller 110 of FIG. 1. To that end, in various embodiments, the data obtaining unit 342 includes instructions and/or logic therefor, and heuristics and metadata therefor.

In some embodiments, the XR presenting unit 344 is configured to present XR content via the one or more XR displays 312. To that end, in various embodiments, the XR presenting unit 344 includes instructions and/or logic therefor, and heuristics and metadata therefor.

In some embodiments, the XR map generating unit 346 is configured to generate a XR map (e.g., a 3D map of the mixed reality scene or a map of the physical environment into which computer-generated objects can be placed to generate the extended reality) based on media content data. To that end, in various embodiments, the XR map generating unit 346 includes instructions and/or logic therefor, and heuristics and metadata therefor.

In some embodiments, the data transmitting unit 348 is configured to transmit data (e.g., presentation data, location data, etc.) to at least the controller 110, and optionally one or more of the input devices 125, output devices 155, sensors 190, and/or peripheral devices 195. To that end, in various embodiments, the data transmitting unit 348 includes instructions and/or logic therefor, and heuristics and metadata therefor.

Although the data obtaining unit 342, the XR presenting unit 344, the XR map generating unit 346, and the data transmitting unit 348 are shown as residing on a single device (e.g., the display generation component 120 of FIG. 1), it should be understood that in other embodiments, any combination of the data obtaining unit 342, the XR presenting unit 344, the XR map generating unit 346, and the data transmitting unit 348 may be located in separate computing devices.

Moreover, FIG. 3 is intended more as a functional description of the various features that could be present in a particular implementation as opposed to a structural schematic of the embodiments described herein. As recognized by those of ordinary skill in the art, items shown separately could be combined and some items could be separated. For example, some functional modules shown separately in FIG. 3 could be implemented in a single module and the various functions of single functional blocks could be implemented by one or more functional blocks in various embodiments. The actual number of modules and the division of particular functions and how features are allocated among them will vary from one implementation to another and, in some embodiments, depends in part on the particular combination of hardware, software, and/or firmware chosen for a particular implementation.

Figure 4:
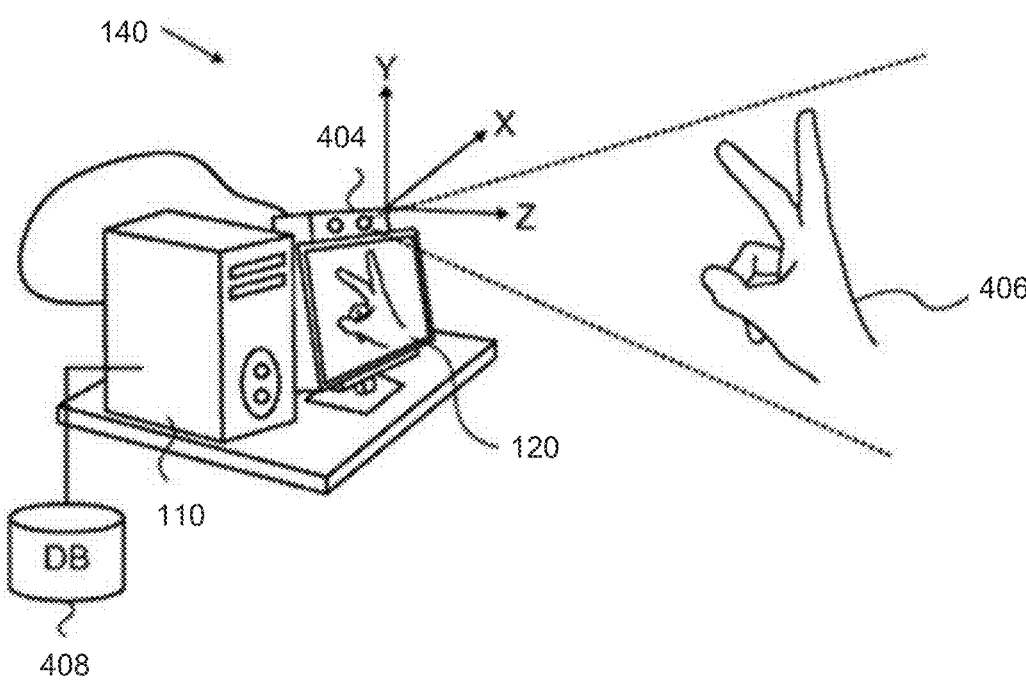
FIG. 4 is a block diagram illustrating a hand tracking unit of a computer system that is configured to capture gesture inputs of the user in accordance with some embodiments.
Figure 4:
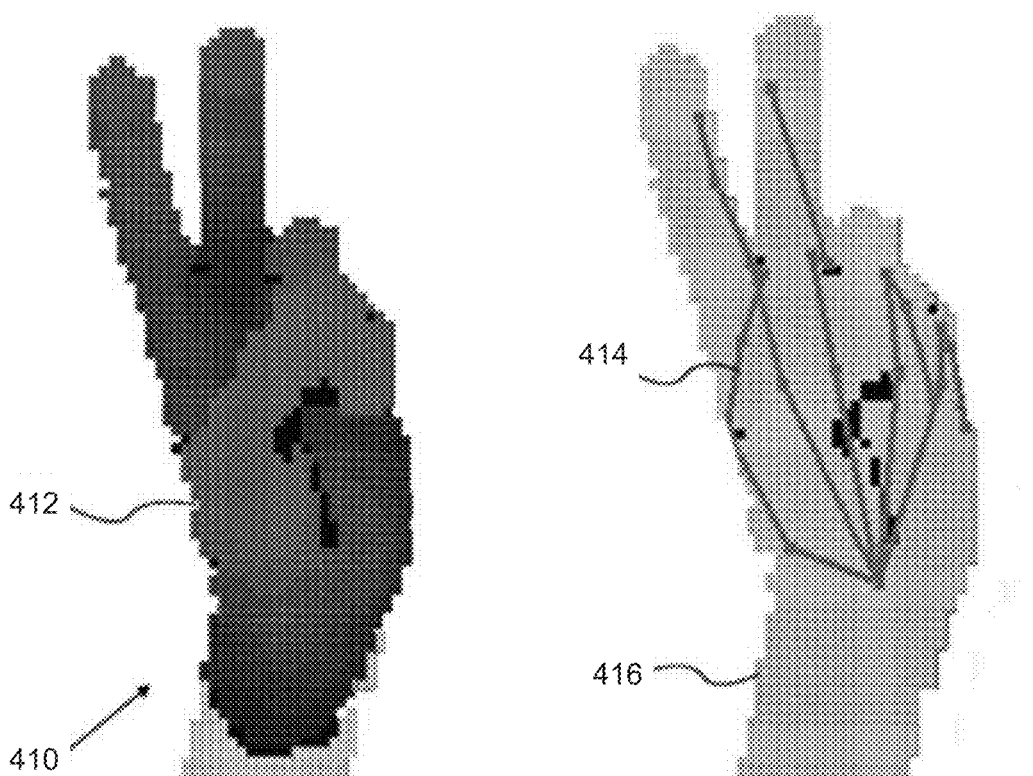

FIG. 4 is a schematic, pictorial illustration of an example embodiment of the hand tracking device 140. In some embodiments, hand tracking device 140 (FIG. 1) is controlled by hand tracking unit 244 (FIG. 2) to track the position/location of one or more portions of the user's hands, and/or motions of one or more portions of the user's hands with respect to the scene 105 of FIG. 1 (e.g., with respect to a portion of the physical environment surrounding the user, with respect to the display generation component 120, or with respect to a portion of the user (e.g., the user's face, eyes, or head), and/or relative to a coordinate system defined relative to the user's hand). In some embodiments, the hand tracking device 140 is part of the display generation component 120 (e.g., embedded in or attached to a head-mounted device). In some embodiments, the hand tracking device 140 is separate from the display generation component 120 (e.g., located in separate housings or attached to separate physical support structures).

In some embodiments, the hand tracking device 140 includes image sensors 404 (e.g., one or more IR cameras, 3D cameras, depth cameras, and/or color cameras, etc.) that capture three-dimensional scene information that includes at least a hand 406 of a human user. The image sensors 404 capture the hand images with sufficient resolution to enable the fingers and their respective positions to be distinguished. The image sensors 404 typically capture images of other parts of the user's body, as well, or possibly all of the body, and may have either zoom capabilities or a dedicated sensor with enhanced magnification to capture images of the hand with the desired resolution. In some embodiments, the image sensors 404 also capture 2D color video images of the hand 406 and other elements of the scene. In some embodiments, the image sensors 404 are used in conjunction with other image sensors to capture the physical environment of the scene 105, or serve as the image sensors that capture the physical environments of the scene 105. In some embodiments, the image sensors 404 are positioned relative to the user or the user's environment in a way that a field of view of the image sensors or a portion thereof is used to define an interaction space in which hand movement captured by the image sensors are treated as inputs to the controller 110.

In some embodiments, the image sensors 404 output a sequence of frames containing 3D map data (and possibly color image data, as well) to the controller 110, which extracts high-level information from the map data. This high-level information is typically provided via an Application Program Interface (API) to an application running on the controller, which drives the display generation component 120 accordingly. For example, the user may interact with software running on the controller 110 by moving his hand 406 and changing his hand posture.

In some embodiments, the image sensors 404 project a pattern of spots onto a scene containing the hand 406 and capture an image of the projected pattern. In some embodiments, the controller 110 computes the 3D coordinates of points in the scene (including points on the surface of the user's hand) by triangulation, based on transverse shifts of the spots in the pattern. This approach is advantageous in that it does not require the user to hold or wear any sort of beacon, sensor, or other marker. It gives the depth coordinates of points in the scene relative to a predetermined reference plane, at a certain distance from the image sensors 404. In the present disclosure, the image sensors 404 are assumed to define an orthogonal set of x, y, z axes, so that depth coordinates of points in the scene correspond to z components measured by the image sensors. Alternatively, the image sensors 404 (e.g., a hand tracking device) may use other methods of 3D mapping, such as stereoscopic imaging or time-of-flight measurements, based on single or multiple cameras or other types of sensors.

In some embodiments, the hand tracking device 140 captures and processes a temporal sequence of depth maps containing the user's hand, while the user moves his hand (e.g., whole hand or one or more fingers). Software running on a processor in the image sensors 404 and/or the controller 110 processes the 3D map data to extract patch descriptors of the hand in these depth maps. The software matches these descriptors to patch descriptors stored in a database 408, based on a prior learning process, in order to estimate the pose of the hand in each frame. The pose typically includes 3D locations of the user's hand joints and finger tips.

The software may also analyze the trajectory of the hands and/or fingers over multiple frames in the sequence in order to identify gestures. The pose estimation functions described herein may be interleaved with motion tracking functions, so that patch-based pose estimation is performed only once in every two (or more) frames, while tracking is used to find changes in the pose that occur over the remaining frames. The pose, motion, and gesture information are provided via the above-mentioned API to an application program running on the controller 110. This program may, for example, move and modify images presented on the display generation component 120, or perform other functions, in response to the pose and/or gesture information.

In some embodiments, a gesture includes an air gesture. An air gesture is a gesture that is detected without the user touching (or independently of) an input element that is part of a device (e.g., computer system 101, one or more input device 125, and/or hand tracking device 140) and is based on detected motion of a portion (e.g., the head, one or more arms, one or more hands, one or more fingers, and/or one or more legs) of the user's body through the air including motion of the user's body relative to an absolute reference (e.g., an angle of the user's arm relative to the ground or a distance of the user's hand relative to the ground), relative to another portion of the user's body (e.g., movement of a hand of the user relative to a shoulder of the user, movement of one hand of the user relative to another hand of the user, and/or movement of a finger of the user relative to another finger or portion of a hand of the user), and/or absolute motion of a portion of the user's body (e.g., a tap gesture that includes movement of a hand in a predetermined pose by a predetermined amount and/or speed, or a shake gesture that includes a predetermined speed or amount of rotation of a portion of the user's body).

In some embodiments, input gestures used in the various examples and embodiments described herein include air gestures performed by movement of the user's finger(s) relative to other finger(s) (or part(s) of the user's hand) for interacting with an XR environment (e.g., a virtual or mixed-reality environment), in some embodiments. In some embodiments, an air gesture is a gesture that is detected without the user touching an input element that is part of the device (or independently of an input element that is a part of the device) and is based on detected motion of a portion of the user's body through the air including motion of the user's body relative to an absolute reference (e.g., an angle of the user's arm relative to the ground or a distance of the user's hand relative to the ground), relative to another portion of the user's body (e.g., movement of a hand of the user relative to a shoulder of the user, movement of one hand of the user relative to another hand of the user, and/or movement of a finger of the user relative to another finger or portion of a hand of the user), and/or absolute motion of a portion of the user's body (e.g., a tap gesture that includes movement of a hand in a predetermined pose by a predetermined amount and/or speed, or a shake gesture that includes a predetermined speed or amount of rotation of a portion of the user's body).

In some embodiments in which the input gesture is an air gesture (e.g., in the absence of physical contact with an input device that provides the computer system with information about which user interface element is the target of the user input, such as contact with a user interface element displayed on a touchscreen, or contact with a mouse or trackpad to move a cursor to the user interface element), the gesture takes into account the user's attention (e.g., gaze) to determine the target of the user input (e.g., for direct inputs, as described below). Thus, in implementations involving air gestures, the input gesture is, for example, detected attention (e.g., gaze) toward the user interface element in combination (e.g., concurrent) with movement of a user's finger(s) and/or hands to perform a pinch and/or tap input, as described in more detail below.

In some embodiments, input gestures that are directed to a user interface object are performed directly or indirectly with reference to a user interface object. For example, a user input is performed directly on the user interface object in performing the input gesture with the user's hand at a position that corresponds to the position of the user interface object in the three-dimensional environment (e.g., as determined based on a current viewpoint of the user). In some embodiments, the input gesture is performed indirectly on the user interface object in accordance with the user performing the input gesture while a position of the user's hand is not at the position that corresponds to the position of the user interface object in the three-dimensional environment while detecting the user's attention (e.g., gaze) on the user interface object. For example, for direct input gesture, the user is enabled to direct the user's input to the user interface object by initiating the gesture at, or near, a position corresponding to the displayed position of the user interface object (e.g., within 0.5 cm, 1 cm, 5 cm, or a distance between 0-5 cm, as measured from an outer edge of the option or a center portion of the option). For an indirect input gesture, the user is enabled to direct the user's input to the user interface object by paying attention to the user interface object (e.g., by gazing at the user interface object) and, while paying attention to the option, the user initiates the input gesture (e.g., at any position that is detectable by the computer system) (e.g., at a position that does not correspond to the displayed position of the user interface object).

In some embodiments, input gestures (e.g., air gestures) used in the various examples and embodiments described herein include pinch inputs and tap inputs, for interacting with a virtual or mixed-reality environment, in some embodiments. For example, the pinch inputs and tap inputs described below are performed as air gestures.

In some embodiments, a pinch input is part of an air gesture that includes one or more of: a pinch gesture, a long pinch gesture, a pinch and drag gesture, or a double pinch gesture. For example, a pinch gesture that is an air gesture includes movement of two or more fingers of a hand to make contact with one another, that is, optionally, followed by an immediate (e.g., within 0-1 seconds) break in contact from each other. A long pinch gesture that is an air gesture includes movement of two or more fingers of a hand to make contact with one another for at least a threshold amount of time (e.g., at least 1 second), before detecting a break in contact with one another. For example, a long pinch gesture includes the user holding a pinch gesture (e.g., with the two or more fingers making contact), and the long pinch gesture continues until a break in contact between the two or more fingers is detected. In some embodiments, a double pinch gesture that is an air gesture comprises two (e.g., or more) pinch inputs (e.g., performed by the same hand) detected in immediate (e.g., within a predefined time period) succession of each other. For example, the user performs a first pinch input (e.g., a pinch input or a long pinch input), releases the first pinch input (e.g., breaks contact between the two or more fingers), and performs a second pinch input within a predefined time period (e.g., within 1 second or within 2 seconds) after releasing the first pinch input.

In some embodiments, a pinch and drag gesture that is an air gesture includes a pinch gesture (e.g., a pinch gesture or a long pinch gesture) performed in conjunction with (e.g., followed by) a drag input that changes a position of the user's hand from a first position (e.g., a start position of the drag) to a second position (e.g., an end position of the drag). In some embodiments, the user maintains the pinch gesture while performing the drag input, and releases the pinch gesture (e.g., opens their two or more fingers) to end the drag gesture (e.g., at the second position). In some embodiments, the pinch input and the drag input are performed by the same hand (e.g., the user pinches two or more fingers to make contact with one another and moves the same hand to the second position in the air with the drag gesture). In some embodiments, the pinch input is performed by a first hand of the user and the drag input is performed by the second hand of the user (e.g., the user's second hand moves from the first position to the second position in the air while the user continues the pinch input with the user's first hand). In some embodiments, an input gesture that is an air gesture includes inputs (e.g., pinch and/or tap inputs) performed using both of the user's two hands. For example, the input gesture includes two (e.g., or more) pinch inputs performed in conjunction with (e.g., concurrently with, or within a pre-defined time period of) each other. For example, a first pinch gesture performed using a first hand of the user (e.g., a pinch input, a long pinch input, or a pinch and drag input), and, in conjunction with performing the pinch input using the first hand, performing a second pinch input using the other hand (e.g., the second hand of the user's two hands). In some embodiments, movement between the user's two hands (e.g., to increase and/or decrease a distance or relative orientation between the user's two hands).

In some embodiments, a tap input (e.g., directed to a user interface element) performed as an air gesture includes movement of a user's finger(s) toward the user interface element, movement of the user's hand toward the user interface element optionally with the user's finger(s) extended toward the user interface element, a downward motion of a user's finger (e.g., mimicking a mouse click motion or a tap on a touchscreen), or other predefined movement of the user's hand. In some embodiments a tap input that is performed as an air gesture is detected based on movement characteristics of the finger or hand performing the tap gesture movement of a finger or hand away from the viewpoint of the user and/or toward an object that is the target of the tap input followed by an end of the movement. In some embodiments the end of the movement is detected based on a change in movement characteristics of the finger or hand performing the tap gesture (e.g., an end of movement away from the viewpoint of the user and/or toward the object that is the target of the tap input, a reversal of direction of movement of the finger or hand, and/or a reversal of a direction of acceleration of movement of the finger or hand).

In some embodiments, attention of a user is determined to be directed to a portion of the three-dimensional environment based on detection of gaze directed to the portion of the three-dimensional environment (optionally, without requiring other conditions). In some embodiments, attention of a user is determined to be directed to a portion of the three-dimensional environment based on detection of gaze directed to the portion of the three-dimensional environment with one or more additional conditions such as requiring that gaze is directed to the portion of the three-dimensional environment for at least a threshold duration (e.g., a dwell duration) and/or requiring that the gaze is directed to the portion of the three-dimensional environment while the viewpoint of the user is within a distance threshold from the portion of the three-dimensional environment in order for the device to determine that attention of the user is directed to the portion of the three-dimensional environment, where if one of the additional conditions is not met, the device determines that attention is not directed to the portion of the three-dimensional environment toward which gaze is directed (e.g., until the one or more additional conditions are met).

In some embodiments, the detection of a ready state configuration of a user or a portion of a user is detected by the computer system. Detection of a ready state configuration of a hand is used by a computer system as an indication that the user is likely preparing to interact with the computer system using one or more air gesture inputs performed by the hand (e.g., a pinch, tap, pinch and drag, double pinch, long pinch, or other air gesture described herein). For example, the ready state of the hand is determined based on whether the hand has a predetermined hand shape (e.g., a pre-pinch shape with a thumb and one or more fingers extended and spaced apart ready to make a pinch or grab gesture or a pre-tap with one or more fingers extended and palm facing away from the user), based on whether the hand is in a predetermined position relative to a viewpoint of the user (e.g., below the user's head and above the user's waist and extended out from the body by at least 15, 20, 25, 30, or 50 cm), and/or based on whether the hand has moved in a particular manner (e.g., moved toward a region in front of the user above the user's waist and below the user's head or moved away from the user's body or leg). In some embodiments, the ready state is used to determine whether interactive elements of the user interface respond to attention (e.g., gaze) inputs.

In scenarios where inputs are described with reference to air gestures, it should be understood that similar gestures could be detected using a hardware input device that is attached to or held by one or more hands of a user, where the position of the hardware input device in space can be tracked using optical tracking, one or more accelerometers, one or more gyroscopes, one or more magnetometers, and/or one or more inertial measurement units and the position and/or movement of the hardware input device is used in place of the position and/or movement of the one or more hands in the corresponding air gesture(s). In scenarios where inputs are described with reference to air gestures, it should be understood that similar gestures could be detected using a hardware input device that is attached to or held by one or more hands of a user, user inputs can be detected with controls contained in the hardware input device such as one or more touch-sensitive input elements, one or more pressure-sensitive input elements, one or more buttons, one or more knobs, one or more dials, one or more joysticks, one or more hand or finger coverings that can detect a position or change in position of portions of a hand and/or fingers relative to each other, relative to the user's body, and/or relative to a physical environment of the user, and/or other hardware input device controls, wherein the user inputs with the controls contained in the hardware input device are used in place of hand and/or finger gestures such as air taps or air pinches in the corresponding air gesture(s). For example, a selection input that is described as being performed with an air tap or air pinch input could be alternatively detected with a button press, a tap on a touch-sensitive surface, a press on a pressure-sensitive surface, or other hardware input. As another example, a movement input that is described as being performed with an air pinch and drag could be alternatively detected based on an interaction with the hardware input control such as a button press and hold, a touch on a touch-sensitive surface, a press on a pressure-sensitive surface, or other hardware input that is followed by movement of the hardware input device (e.g., along with the hand with which the hardware input device is associated) through space. Similarly, a two-handed input that includes movement of the hands relative to each other could be performed with one air gesture and one hardware input device in the hand that is not performing the air gesture, two hardware input devices held in different hands, or two air gestures performed by different hands using various combinations of air gestures and/or the inputs detected by one or more hardware input devices that are described above.

In some embodiments, the software may be downloaded to the controller 110 in electronic form, over a network, for example, or it may alternatively be provided on tangible, non-transitory media, such as optical, magnetic, or electronic memory media. In some embodiments, the database 408 is likewise stored in a memory associated with the controller 110. Alternatively or additionally, some or all of the described functions of the computer may be implemented in dedicated hardware, such as a custom or semi-custom integrated circuit or a programmable digital signal processor (DSP). Although the controller 110 is shown in FIG. 4, by way of example, as a separate unit from the image sensors 404, some or all of the processing functions of the controller may be performed by a suitable microprocessor and software or by dedicated circuitry within the housing of the image sensors 404 (e.g., a hand tracking device) or otherwise associated with the image sensors 404. In some embodiments, at least some of these processing functions may be carried out by a suitable processor that is integrated with the display generation component 120 (e.g., in a television set, a handheld device, or head-mounted device, for example) or with any other suitable computerized device, such as a game console or media player. The sensing functions of image sensors 404 may likewise be integrated into the computer or other computerized apparatus that is to be controlled by the sensor output.

FIG. 4 further includes a schematic representation of a depth map 410 captured by the image sensors 404, in some embodiments. The depth map, as explained above, comprises a matrix of pixels having respective depth values. The pixels 412 corresponding to the hand 406 have been segmented out from the background and the wrist in this map. The brightness of each pixel within the depth map 410 corresponds inversely to its depth value, i.e., the measured z distance from the image sensors 404, with the shade of gray growing darker with increasing depth. The controller 110 processes these depth values in order to identify and segment a component of the image (i.e., a group of neighboring pixels) having characteristics of a human hand. These characteristics, may include, for example, overall size, shape and motion from frame to frame of the sequence of depth maps.

FIG. 4 also schematically illustrates a hand skeleton 414 that controller 110 ultimately extracts from the depth map 410 of the hand 406, in some embodiments. In FIG. 4, the hand skeleton 414 is superimposed on a hand background 416 that has been segmented from the original depth map. In some embodiments, key feature points of the hand (e.g., points corresponding to knuckles, finger tips, center of the palm, end of the hand connecting to wrist, etc.) and optionally on the wrist or arm connected to the hand are identified and located on the hand skeleton 414. In some embodiments, location and movements of these key feature points over multiple image frames are used by the controller 110 to determine the hand gestures performed by the hand or the current state of the hand, in some embodiments.

Figure 5:
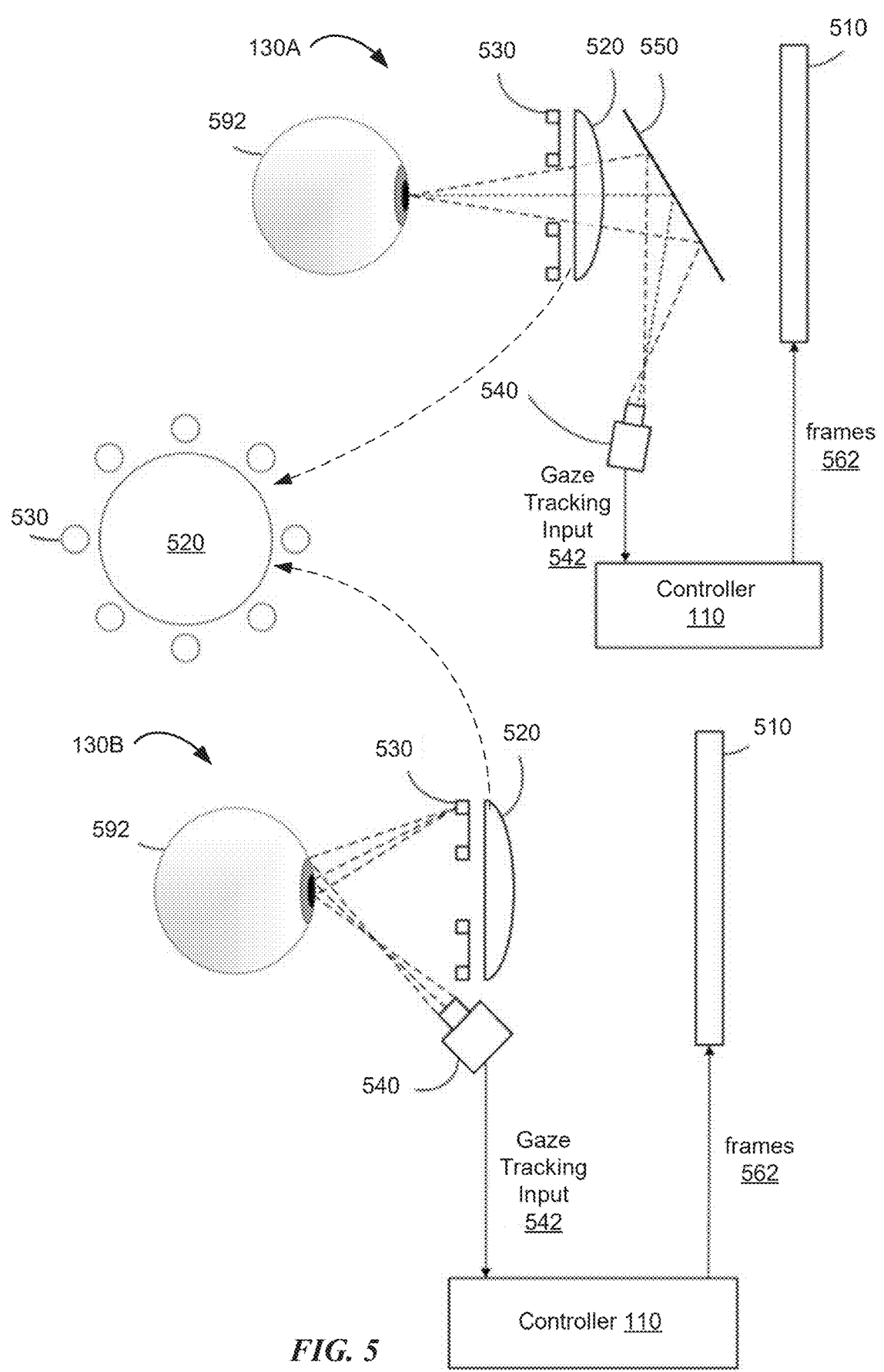
FIG. 5 is a block diagram illustrating an eye tracking unit of a computer system that is configured to capture gaze inputs of the user in accordance with some embodiments.

FIG. 5 illustrates an example embodiment of the eye tracking device 130 (FIG. 1). In some embodiments, the eye tracking device 130 is controlled by the eye tracking unit 243 (FIG. 2) to track the position and movement of the user's gaze with respect to the scene 105 or with respect to the XR content displayed via the display generation component 120. In some embodiments, the eye tracking device 130 is integrated with the display generation component 120. For example, in some embodiments, when the display generation component 120 is a head-mounted device such as headset, helmet, goggles, or glasses, or a handheld device placed in a wearable frame, the head-mounted device includes both a component that generates the XR content for viewing by the user and a component for tracking the gaze of the user relative to the XR content. In some embodiments, the eye tracking device 130 is separate from the display generation component 120. For example, when display generation component is a handheld device or a XR chamber, the eye tracking device 130 is optionally a separate device from the handheld device or XR chamber. In some embodiments, the eye tracking device 130 is a head-mounted device or part of a head-mounted device. In some embodiments, the head-mounted eye-tracking device 130 is optionally used in conjunction with a display generation component that is also head-mounted, or a display generation component that is not head-mounted. In some embodiments, the eye tracking device 130 is not a head-mounted device, and is optionally used in conjunction with a head-mounted display generation component. In some embodiments, the eye tracking device 130 is not a head-mounted device, and is optionally part of a non-head-mounted display generation component.

In some embodiments, the display generation component 120 uses a display mechanism (e.g., left and right near-eye display panels) for displaying frames including left and right images in front of a user's eyes to thus provide 3D virtual views to the user. For example, a head-mounted display generation component may include left and right optical lenses (referred to herein as eye lenses) located between the display and the user's eyes. In some embodiments, the display generation component may include or be coupled to one or more external video cameras that capture video of the user's environment for display. In some embodiments, a head-mounted display generation component may have a transparent or semi-transparent display through which a user may view the physical environment directly and display virtual objects on the transparent or semi-transparent display. In some embodiments, display generation component projects virtual objects into the physical environment. The virtual objects may be projected, for example, on a physical surface or as a holograph, so that an individual, using the system, observes the virtual objects superimposed over the physical environment. In such cases, separate display panels and image frames for the left and right eyes may not be necessary.

As shown in FIG. 5, in some embodiments, eye tracking device 130 (e.g., a gaze tracking device) includes at least one eye tracking camera (e.g., infrared (IR) or near-IR (NIR) cameras), and illumination sources (e.g., IR or NIR light sources such as an array or ring of LEDs) that emit light (e.g., IR or NIR light) towards the user's eyes. The eye tracking cameras may be pointed towards the user's eyes to receive reflected IR or NIR light from the light sources directly from the eyes, or alternatively may be pointed towards "hot" mirrors located between the user's eyes and the display panels that reflect IR or NIR light from the eyes to the eye tracking cameras while allowing visible light to pass. The eye tracking device 130 optionally captures images of the user's eyes (e.g., as a video stream captured at 60-120 frames per second (fps)), analyze the images to generate gaze tracking information, and communicate the gaze tracking information to the controller 110. In some embodiments, two eyes of the user are separately tracked by respective eye tracking cameras and illumination sources. In some embodiments, only one eye of the user is tracked by a respective eye tracking camera and illumination sources.

In some embodiments, the eye tracking device 130 is calibrated using a device-specific calibration process to determine parameters of the eye tracking device for the specific operating environment 100, for example the 3D geometric relationship and parameters of the LEDs, cameras, hot mirrors (if present), eye lenses, and display screen. The device-specific calibration process may be performed at the factory or another facility prior to delivery of the AR/VR equipment to the end user. The device-specific calibration process may be an automated calibration process or a manual calibration process. A user-specific calibration process may include an estimation of a specific user's eye parameters, for example the pupil location, fovea location, optical axis, visual axis, eye spacing, etc. Once the device-specific and user-specific parameters are determined for the eye tracking device 130, images captured by the eye tracking cameras can be processed using a glint-assisted method to determine the current visual axis and point of gaze of the user with respect to the display, in some embodiments.

As shown in FIG. 5, the eye tracking device 130 (e.g., 130A or 130B) includes eye lens(es) 520, and a gaze tracking system that includes at least one eye tracking camera 540 (e.g., infrared (IR) or near-IR (NIR) cameras) positioned on a side of the user's face for which eye tracking is performed, and an illumination source 530 (e.g., IR or NIR light sources such as an array or ring of NIR light-emitting diodes (LEDs)) that emit light (e.g., IR or NIR light) towards the user's eye(s) 592. The eye tracking cameras 540 may be pointed towards mirrors 550 located between the user's eye(s) 592 and a display 510 (e.g., a left or right display panel of a head-mounted display, or a display of a handheld device, a projector, etc.) that reflect IR or NIR light from the eye(s) 592 while allowing visible light to pass (e.g., as shown in the top portion of FIG. 5), or alternatively may be pointed towards the user's eye(s) 592 to receive reflected IR or NIR light from the eye(s) 592 (e.g., as shown in the bottom portion of FIG. 5).

In some embodiments, the controller 110 renders AR or VR frames 562 (e.g., left and right frames for left and right display panels) and provides the frames 562 to the display 510. The controller 110 uses gaze tracking input 542 from the eye tracking cameras 540 for various purposes, for example in processing the frames 562 for display. The controller 110 optionally estimates the user's point of gaze on the display 510 based on the gaze tracking input 542 obtained from the eye tracking cameras 540 using the glint-assisted methods or other suitable methods. The point of gaze estimated from the gaze tracking input 542 is optionally used to determine the direction in which the user is currently looking.

The following describes several possible use cases for the user's current gaze direction, and is not intended to be limiting. As an example use case, the controller 110 may render virtual content differently based on the determined direction of the user's gaze. For example, the controller 110 may generate virtual content at a higher resolution in a foveal region determined from the user's current gaze direction than in peripheral regions. As another example, the controller may position or move virtual content in the view based at least in part on the user's current gaze direction. As another example, the controller may display particular virtual content in the view based at least in part on the user's current gaze direction. As another example use case in AR applications, the controller 110 may direct external cameras for capturing the physical environments of the XR experience to focus in the determined direction. The autofocus mechanism of the external cameras may then focus on an object or surface in the environment that the user is currently looking at on the display 510. As another example use case, the eye lenses 520 may be focusable lenses, and the gaze tracking information is used by the controller to adjust the focus of the eye lenses 520 so that the virtual object that the user is currently looking at has the proper vergence to match the convergence of the user's eyes 592. The controller 110 may leverage the gaze tracking information to direct the eye lenses 520 to adjust focus so that close objects that the user is looking at appear at the right distance.

In some embodiments, the eye tracking device is part of a head-mounted device that includes a display (e.g., display 510), two eye lenses (e.g., eye lens(es) 520), eye tracking cameras (e.g., eye tracking camera(s) 540), and light sources (e.g., light sources 530 (e.g., IR or NIR LEDs)), mounted in a wearable housing. The light sources emit light (e.g., IR or NIR light) towards the user's eye(s) 592. In some embodiments, the light sources may be arranged in rings or circles around each of the lenses as shown in FIG. 5. In some embodiments, eight light sources 530 (e.g., LEDs) are arranged around each lens 520 as an example. However, more or fewer light sources 530 may be used, and other arrangements and locations of light sources 530 may be used.

In some embodiments, the display 510 emits light in the visible light range and does not emit light in the IR or NIR range, and thus does not introduce noise in the gaze tracking system. Note that the location and angle of eye tracking camera(s) 540 is given by way of example, and is not intended to be limiting. In some embodiments, a single eye tracking camera 540 is located on each side of the user's face. In some embodiments, two or more NIR cameras 540 may be used on each side of the user's face. In some embodiments, a camera 540 with a wider field of view (FOV) and a camera 540 with a narrower FOV may be used on each side of the user's face. In some embodiments, a camera 540 that operates at one wavelength (e.g., 850 nm) and a camera 540 that operates at a different wavelength (e.g., 940 nm) may be used on each side of the user's face.

Embodiments of the gaze tracking system as illustrated in FIG. 5 may, for example, be used in computer-generated reality, virtual reality, and/or mixed reality applications to provide computer-generated reality, virtual reality, augmented reality, and/or augmented virtuality experiences to the user.

Figure 6:
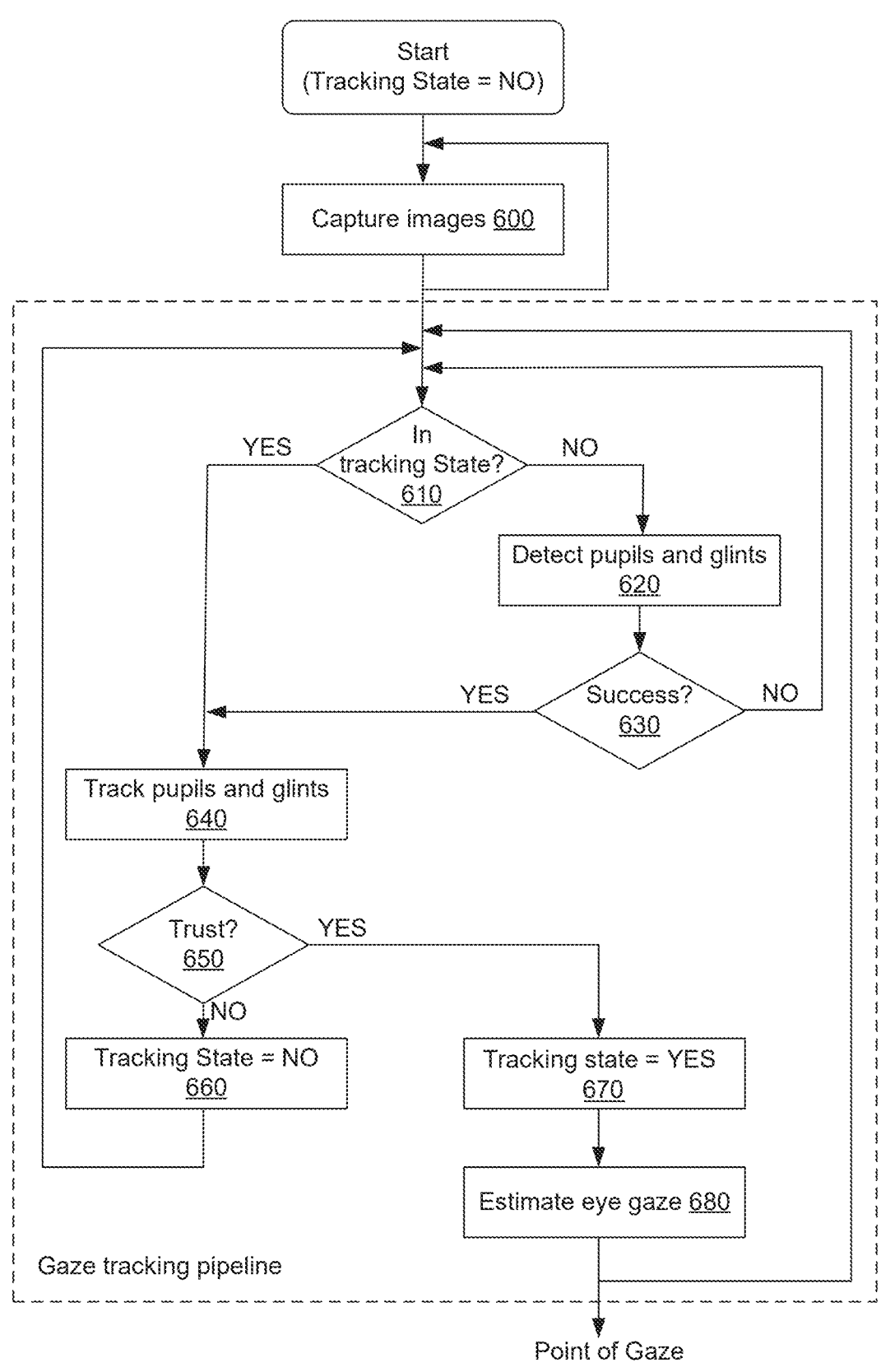
FIG. 6 is a flow diagram illustrating a glint-assisted gaze tracking pipeline in accordance with some embodiments.

FIG. 6 illustrates a glint-assisted gaze tracking pipeline, in some embodiments. In some embodiments, the gaze tracking pipeline is implemented by a glint-assisted gaze tracking system (e.g., eye tracking device 130 as illustrated in FIGS. 1 and 5). The glint-assisted gaze tracking system may maintain a tracking state. Initially, the tracking state is off or "NO". When in the tracking state, the glint-assisted gaze tracking system uses prior information from the previous frame when analyzing the current frame to track the pupil contour and glints in the current frame. When not in the tracking state, the glint-assisted gaze tracking system attempts to detect the pupil and glints in the current frame and, if successful, initializes the tracking state to "YES" and continues with the next frame in the tracking state.

As shown in FIG. 6, the gaze tracking cameras may capture left and right images of the user's left and right eyes. The captured images are then input to a gaze tracking pipeline for processing beginning at 610. As indicated by the arrow returning to element 600, the gaze tracking system may continue to capture images of the user's eyes, for example at a rate of 60 to 120 frames per second. In some embodiments, each set of captured images may be input to the pipeline for processing. However, in some embodiments or under some conditions, not all captured frames are processed by the pipeline.

At 610, for the current captured images, if the tracking state is YES, then the method proceeds to element 640. At 610, if the tracking state is NO, then as indicated at 620 the images are analyzed to detect the user's pupils and glints in the images. At 630, if the pupils and glints are successfully detected, then the method proceeds to element 640. Otherwise, the method returns to element 610 to process next images of the user's eyes.

At 640, if proceeding from element 610, the current frames are analyzed to track the pupils and glints based in part on prior information from the previous frames. At 640, if proceeding from element 630, the tracking state is initialized based on the detected pupils and glints in the current frames. Results of processing at element 640 are checked to verify that the results of tracking or detection can be trusted. For example, results may be checked to determine if the pupil and a sufficient number of glints to perform gaze estimation are successfully tracked or detected in the current frames. At 650, if the results cannot be trusted, then the tracking state is set to NO at element 660, and the method returns to element 610 to process next images of the user's eyes. At 650, if the results are trusted, then the method proceeds to element 670. At 670, the tracking state is set to YES (if not already YES), and the pupil and glint information is passed to element 680 to estimate the user's point of gaze.

FIG. 6 is intended to serve as one example of eye tracking technology that may be used in a particular implementation. As recognized by those of ordinary skill in the art, other eye tracking technologies that currently exist or are developed in the future may be used in place of or in combination with the glint-assisted eye tracking technology describe herein in the computer system 101 for providing XR experiences to users, in some embodiments.

In the present disclosure, various input methods are described with respect to interactions with a computer system. When an example is provided using one input device or input method and another example is provided using another input device or input method, it is to be understood that each example may be compatible with and optionally utilizes the input device or input method described with respect to another example. Similarly, various output methods are described with respect to interactions with a computer system. When an example is provided using one output device or output method and another example is provided using another output device or output method, it is to be understood that each example may be compatible with and optionally utilizes the output device or output method described with respect to another example. Similarly, various methods are described with respect to interactions with a virtual environment or a mixed reality environment through a computer system. When an example is provided using interactions with a virtual environment and another example is provided using mixed reality environment, it is to be understood that each example may be compatible with and optionally utilizes the methods described with respect to another example. As such, the present disclosure discloses embodiments that are combinations of the features of multiple examples, without exhaustively listing all features of an embodiment in the description of each example embodiment.

User Interfaces and Associated Processes

Attention is now directed towards embodiments of user interfaces ("UI") and associated processes that may be implemented on a computer system, such as a portable multifunction device or a head-mounted device, in communication with a display generation component, one or more sensors, and (optionally) one or more audio generation components.

FIGS. 7A-7L illustrate examples of providing computer-generated user experience sessions in an extended reality (XR) environment. FIG. 8 is a flow diagram of an exemplary method 800 for providing a computer-generated user experience session with particles that move based on breathing characteristics of a user. FIG. 9 is a flow diagram of an exemplary method 900 for providing a computer-generated user experience session with options selected based on characteristics of an XR environment. FIGS. 10A-10B are a flow diagram of an exemplary method 1000 for providing a computer-generated user experience session with a soundscape having randomly selected curated sound components. The user interfaces in FIGS. 7A-7L are used to illustrate the processes described below, including the processes in FIGS. 8, 9, 10A, and 10B.

The figures and accompanying description are provided to describe various embodiments of a computer-generated user experience session in an XR environment. The various embodiments are described with respect to an example user experience session that is provided by a meditation application operating at a computer system. This user experience session is referred to as a "meditation session." The meditation session is described herein as having various phases or portions with respective visual and audio characteristics for the meditation session and/or respective portions thereof. For example, the meditation session is described as having an introductory portion, a guided breathing portion, a reflection portion, and an outro portion. Additionally, the meditation session is described as having various visual characteristics such as, for example, virtual objects (e.g., shapes, particles, and/or user interfaces), virtual overlays, virtual wallpapers, and visual effects. The meditation session is also described as having various audio characteristics such as, for example, curated soundscapes, which may include sound effects, music, and guided instruction. The meditation session is described as being provided in an XR environment. In some embodiments, the XR environment is an AR environment. In some embodiments, the XR environment is a VR environment. In some embodiments, various options, settings, parameters, and/or characteristics of the meditation session are determined based on whether the meditation session is being performed in an AR environment or a VR environment. For example, in some embodiments, the audio and/or visual characteristics for a meditation session in a VR environment are selected from a subset of audio and/or visual characteristics that are available for a meditation session in an AR environment. In some embodiments, the visual and/or audio characteristics for a meditation session can be selected randomly (or pseudorandomly), optionally with a bias towards not repeating audio and/or visual characteristics of a previous meditation session, to provide a unique user experience for each session. In some embodiments, the audio and/or visual characteristics are selected pseudorandomly. For example, a random number generator is used to select audio characteristics from a superset of audio characteristics. Similarly, a random number generator is used to select the visual characteristics from a superset of visual characteristics. In some embodiments, when an audio and/or visual characteristic is selected pseudorandomly (or randomly) and the selected audio and/or visual characteristic has previously been used (or has been previously used with other particular audio and/or visual characteristics), the selected audio and/or visual characteristic is disregarded and a different audio and/or visual characteristic is selected pseudorandomly (or randomly). It should be appreciated that aspects of the various embodiments described herein can be combined, rearranged, and/or omitted in accordance with the examples described and illustrated in the respective figures. Selection of an element from a set of elements randomly or pseudorandomly entails selecting an element with apparent randomness either based on a number generated from a true source of randomness such radioactive decay or another nondeterministic source or based on a number generated from a deterministic source that is statistically random and produces a result that appears to be random even if it is not in fact truly random. Selecting an element from a set of elements with apparent randomness produces results that do not have discernable deterministic pattern to a typical user of the device.

Figure 7A:
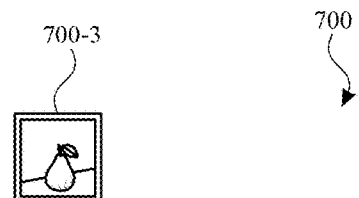
FIGS. 7A-7L illustrate example techniques for providing computer-generated user experience sessions in an extended reality environment, in accordance with some embodiments.
Figure 7A:
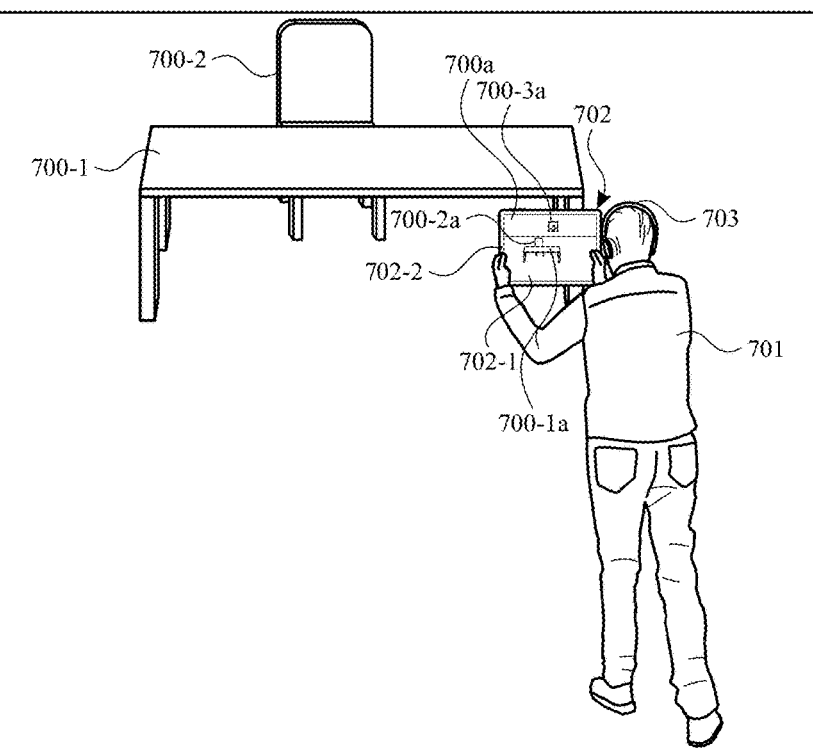

FIG. 7A depicts physical environment 700, which is a physical room that includes physical desk 700-1, physical chair 700-2, and physical painting 700-3. User 701 is in physical environment 700, holding device 702 (e.g., a tablet or smartphone) and wearing audio output device 703 (e.g., headphones or earbuds) that are connected (e.g., wirelessly or through a wired connection) to device 702. Device 702 includes display 702-1 and one or more cameras 702-2. The device cameras are referred to collectively as camera 702-2, and can include a camera located on a display-side of the device (a front-facing camera) and/or a camera located on a different side of the device than the display (a rear-facing camera). In the embodiment depicted in FIG. 7A, the physical desk 700-1, chair 700-2, and painting 700-3 are within a field-of-view of a rear-facing camera of device 702, and a view of the physical environment is displayed on device display 702-1 while the user experience session is not active. The view of the physical environment is a representation 700a of physical environment 700, including representation 700-1a of the physical desk 700-1, representation 700-2a of physical chair 700-2, and representation 700-3a of the physical painting 700-3. In the embodiments described herein, device 702 is used to provide a user experience session (also referred to as a meditation session) in an XR environment displayed on display 702-1 of device 702. Audio of the user experience session is output at audio output device 703. In some embodiments, however, audio can be output using different audio sources such as one or more speakers of device 702. Display 702-1 is a touchscreen display that can be used to display the XR environment and detect user inputs (e.g., touch inputs, tap gestures, swipe gestures, and/or text inputs) for interacting with device 702, the user experience session, and/or the XR environment. In some embodiments, camera 702-2 can be used to detect user inputs (e.g., hand gestures, biometric inputs, and/or breathing actions or gestures) for interacting with device 702, the user experience session, and/or the XR environment. In some embodiments, device 702 includes a microphone that can be used to detect user inputs (e.g., voice commands and/or ambient sounds) for interacting with device 702, the user experience session, and/or the XR environment.

In the embodiment depicted in FIGS. 7A-7L, device 702 is a computer system (similar to computer system 101 in FIG. 1) that is used to provide a user experience session in an XR environment. It should be appreciated, however, that the user experience session can be provided in an XR environment using a different type of computer system. For example, instead of (or in addition to) using device 702, the computer system can be a head-mounted device (HMD) that is worn by user 701. In such embodiments, the HMD includes a display component that is analogous to display 702-1 and one or more sensors analogous to camera 702-2. For example, the display can be an opaque display screen with display components and/or a transparent or translucent display through which user 701 may directly view physical environment 700 and upon which virtual elements of the user experience session can be displayed or projected. The HMD may further include speakers and/or other audio output devices integrated into the HMD for providing audio output, and one or more cameras, microphones, and/or other sensors that are used to capture images (e.g., video and/or pictures) of physical environment 700 (e.g., for display at the HMD and/or for detecting input) and to receive user input in the form of hand gestures, voice gestures, gaze gestures, and/or other input forms discussed herein. While the methods for providing a user experience session in an XR environment are discussed herein with respect to device 702, it should be appreciated that the methods can be performed using other computer systems including, for example, an HMD.

Figure 7B:
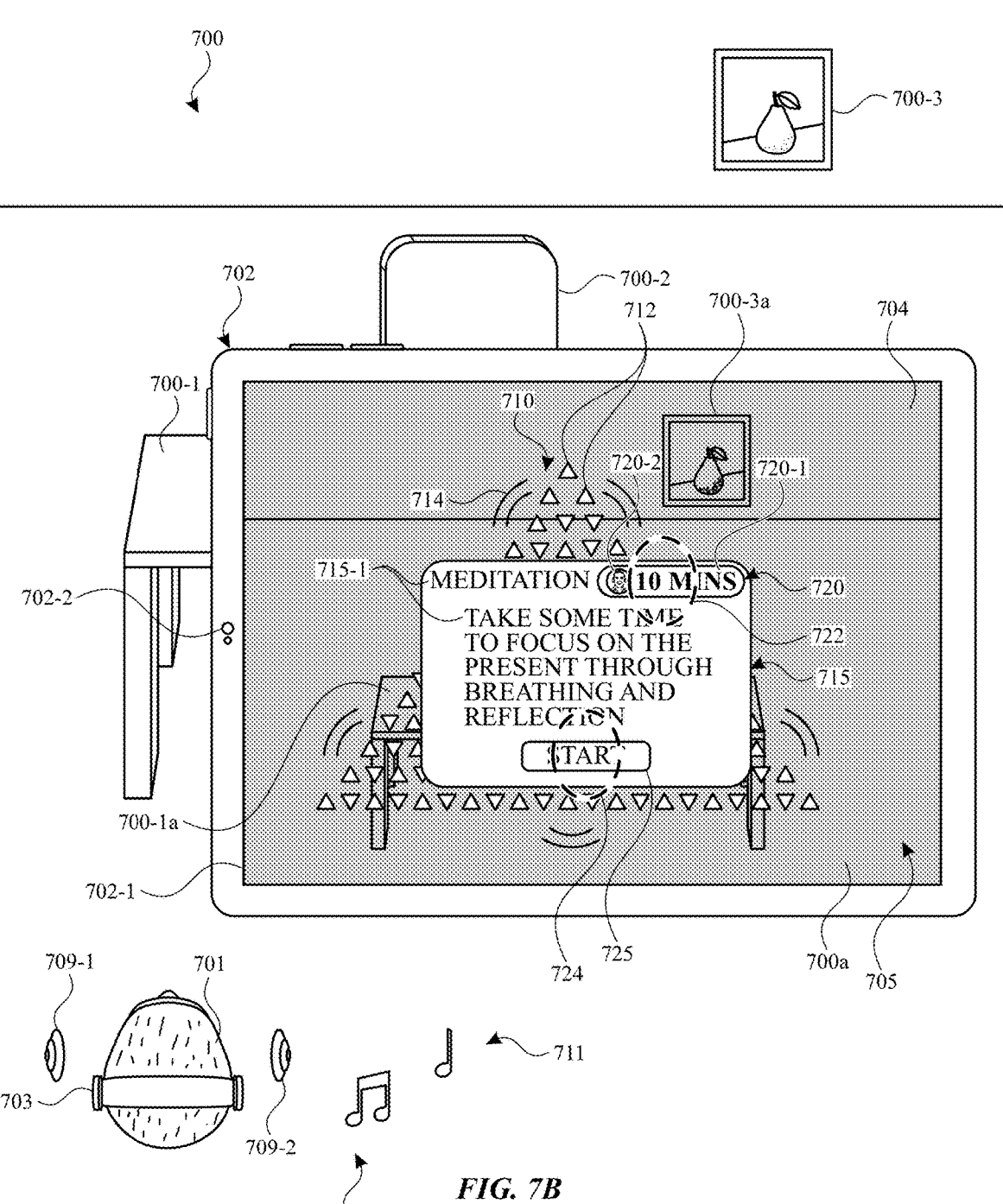
Figure 7C:
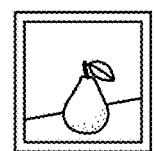
Figure 7D:
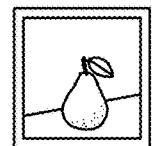
Figure 7E:
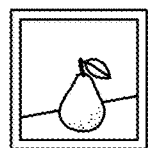
Figure 7F:
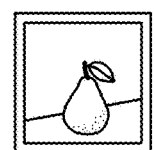
Figure 7G:
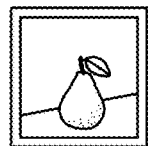
Figure 7H:
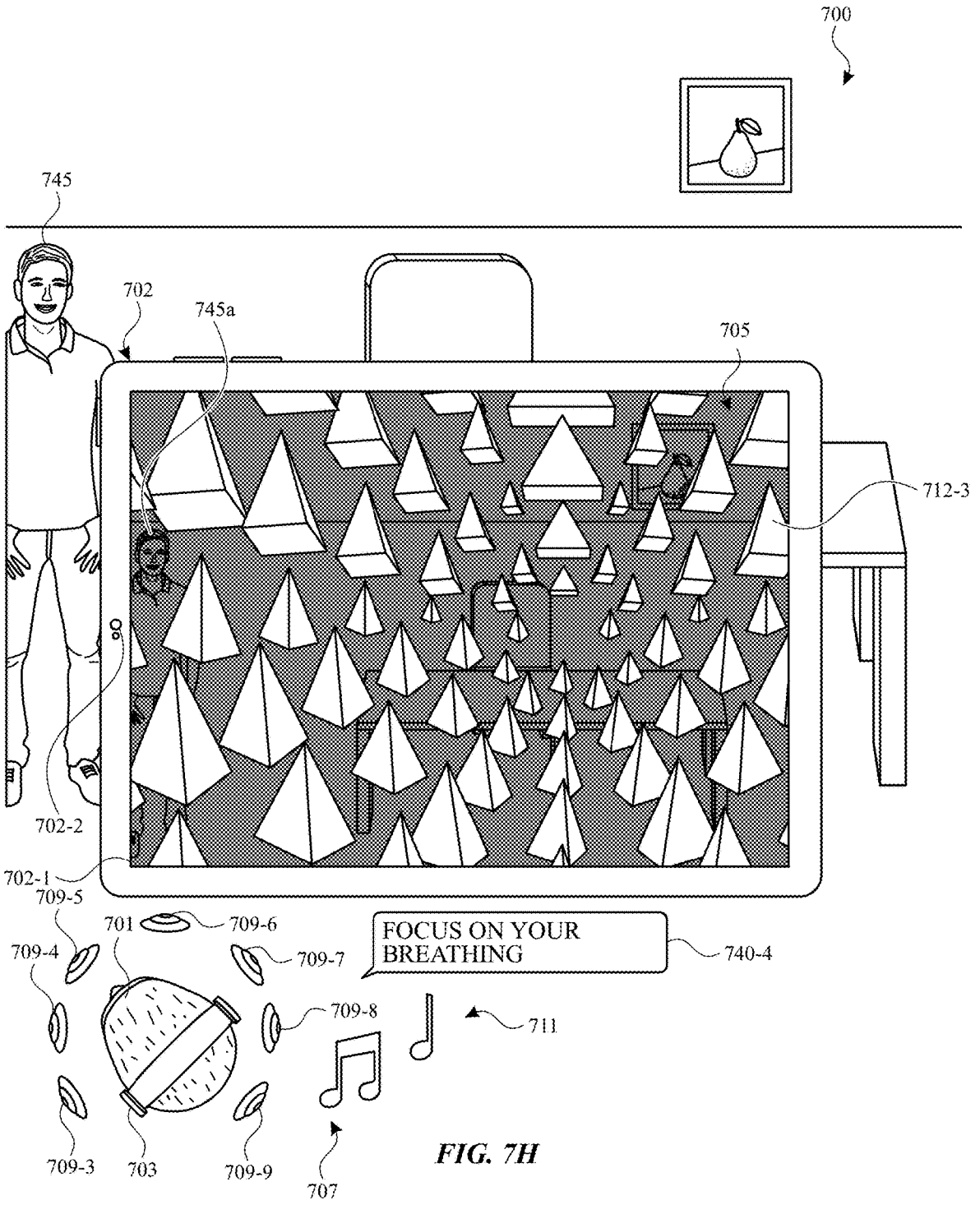
Figure 7I:
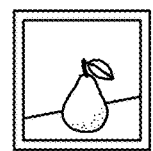
Figure 7J:
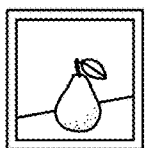
Figure 7K:
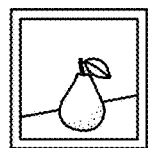
Figure 7L:
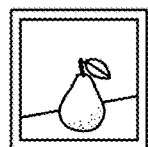

FIGS. 7B-7L depict user interfaces at device 702 for embodiments in which the mediation application is active and, in some instances, when the meditation user session is ongoing. FIGS. 7B-7I depict user interfaces for a meditation session in an AR environment. FIGS. 7J-7L depict user interfaces for a meditation session in a VR environment.

In FIG. 7B, device 702 is providing a first portion (an introductory portion, a starting portion, and/or a portion before the guided breathing portion) of the meditation session and displays, via display 702-1, virtual interface 705 overlaying the displayed representation 700a of physical environment 700. In some embodiments, the virtual interface is displayed as part of an AR environment for the user experience session. In such embodiments, the virtual interface includes a dimming effect 704 that is displayed over the representation 700a of physical environment 700. The dimming effect dims the user's view of the physical environment by allowing, for example, 98% visibility of the physical environment by displaying the dimming effect with 98% transparency (or 2% opacity). The dimming effect can be greater or less, in some embodiments, and can have varying amounts of dimming at different portions of the device display (for example, less opacity of the dimming effect near the center of the display and increasing opacity of the dimming effect towards the perimeter of the device display). The dimming effect can indicate to user 701 that the user is viewing an AR environment and, in some embodiments, helps to focus the user on aspects of the user experience session by reducing distractions that may appear in the physical environment. In some embodiments, the virtual interface is displayed as part of a VR environment for the user experience session. In such embodiments, the virtual interface is opaque and the physical environment 700 may not be visible through the virtual interface. An example of such an interface is illustrated in FIGS. 7J and 7L, discussed in greater detail below. Unless specifically noted otherwise, the values and ranges discussed herein for the various visual effects, such as the dimming effect, are intended as non-limiting examples.

In some embodiments, virtual interface 705 is displayed as part of the user experience session in the XR environment. For example, in FIG. 7B, device 702 displays virtual interface 705 as part of the meditation session provided by a meditation application operating at device 702 and, therefore, includes additional virtual elements that are associated with the meditation session. Specifically, in FIG. 7B, device 702 displays virtual object 710, virtual particles 712, and virtual menu 715 as part of an introductory portion or introductory phase of the meditation session in the XR environment. In some embodiments, virtual interface 705, including dimming effect 704, virtual object 710, particles 712, and menu 715, are displayed by device 702 in response to launching the meditation application in the XR environment (e.g., by detecting selection of a virtual icon for the meditation application in the XR environment and/or by detecting an audio instruction to launch the mediation application in the XR environment). In some embodiments, virtual interface 705 can include a virtual wallpaper.

In some embodiments, the virtual interface is displayed as a part of an XR environment that is separate from or disassociated with the user experience session. For example, the virtual interface can be displayed as part of a virtual staging room or virtual "home" environment that the device displays as part of an XR environment prior to beginning the user experience session (e.g., prior to launching the meditation application and/or after launching the mediation application and before beginning the user experience session). Sometimes, in such embodiments, device 702 does not display virtual object 710, particles 712, or menu 715 and, instead, optionally displays icons or other virtual elements that can be selected to manage the user's experience with the XR environment and/or device 702. For example, device 702 can display icons that are selectable to launch an application operating at the device and/or to access various settings of the XR environment and/or device 702. In some embodiments, user 701 can interact with other users and share the XR environment, including applications launched in the XR environment, with other users.

Virtual object 710 is a graphical element that moves and changes appearance while the meditation application is active (e.g., during the meditation session or not during the meditation session). As shown in FIG. 7B, virtual object 710 has a generally triangular macro shape that is formed by a collection of particles 712. During the introductory portion of the meditation session, device 702 displays particles 712 moving in a rhythmic pattern such that virtual object 710 has a pulsating, swaying, and/or other rhythmic movement (represented in the drawings by lines 714) that conveys a relaxing or soothing environment to user 701. In some embodiments, device 702 displays particles 712 moving closer together and then farther apart, causing virtual object 710 to expand and contract in a rhythmic pattern that mimics a predetermined breathing cadence (or other biometric rhythm such as a heartbeat, brainwaves, or walking rate) while retaining the generally triangular macro shape. In some embodiments, virtual object 710 pulsates (expands and contracts) at a rate that is faster or slower than a predetermined breathing cadence. Additionally, virtual object 710 can have a different macro shape or appearance than that shown in FIG. 7B. For example, in some embodiments, virtual object 710 is a two-dimensional object having a macro shape that is a circle, square, triangle, rectangle, or abstract, two-dimensional shape. In some embodiments, virtual object 710 is a three-dimensional object having a macro shape that is a sphere, orb, cube, rectangular prism, pyramid, or an abstract, three-dimensional shape such as a cloud, or moving arrangement of particles that has an appearance of a floating mist or swirling paintbrush strokes.

In the embodiment illustrated in FIGS. 7B-7I, particles 712 are shown having a triangular shape. However, the particles can have different two- and/or three-dimensional shapes or appearances such as circles, spheres, pyramids, petals, leaves, squares, cubes, clouds, mist droplets, paintbrush strokes, or any combination thereof. In some embodiments, some of the particles have a uniform spacing between adjacent particles. In some embodiments, some of the particles have a non-uniform spacing between adjacent particles. In some embodiments, some of the particles have an overlapping arrangement. In some embodiments, the particles move between the various appearances and spacing arrangements as virtual object 710 moves in the rhythmic pattern. For example, in an expanded state of virtual object 710, particles 712 have a spaced-apart arrangement and, in a contracted state of virtual object 710, particles 712 have an overlapping or less-spaced arrangement. Furthermore, virtual object 710 and/or particles 712 can have different visual characteristics such as an animated effect or appearance, a translucence (e.g., a partial translucence or a total translucence) of the particles, a simulated reflection of light detected in the physical environment (e.g., a simulated reflection off the particles and/or macro shape and/or a simulated bending of light), a simulated reflection of virtual lighting, or a combination thereof. In some embodiments, the visual characteristics of particles 712 and/or virtual object 710 change based on various criteria such as, for example, the physical environment, the XR environment, a state of the meditation session, movement of the user and/or device 702, user input, and/or any combination thereof. In some embodiments, the visual characteristics of the user experience session are randomly (or pseudorandomly) generated by device 702. For example, in some embodiments, device 702 generates the virtual object and/or particles having different, randomly selected visual characteristics each time the meditation application is launched. In some embodiments, the visual characteristics are randomly selected with a bias towards not repeating a previously displayed set of visual characteristics for the user experience session.

In FIG. 7B, device 702 displays menu 715, which is a virtual menu user interface for selecting or modifying various aspects of the meditation session. Menu 715 includes text 715-1 providing context for the meditation session to user 701 (e.g., informing the user that the meditation application is active, indicating that the user experience session is a meditation session, and/or instructing the user to prepare for the meditation session). Menu 715 also includes options element 720, which is selectable to display an options menu for the meditation session. Options element 720 also includes duration indication 720-1 indicating the currently selected duration for the meditation session (e.g., a duration of one or more portions of the meditation session and/or a combined duration for the guided breathing and reflection portions of the mediation session and, optionally, the outro portion), and coach indication 720-2 indicating the currently selected coach for the meditation session. As shown in FIG. 7B, coach indication 720-2 indicates that a male coach is currently selected for the meditation session, and duration indication 720-1 indicates that the duration of the meditation session is selected to be 10 minutes. Menu 715 also includes start element 725, which is selectable (e.g., via input 724 and/or via an audio input) to begin the meditation session by transitioning from the introductory portion to the guided breathing portion of the meditation session. In some embodiments, the meditation application is active, but the meditation session is not considered to be ongoing during the introductory and outro portions. In such embodiments, the meditation session is considered to be started by selecting start element 725. In some embodiments, the meditation session is considered to be ongoing during the introductory and outro portions. In such embodiments, the meditation session is started by launching the meditation application, and selecting start element 725 transitions from one portion of the meditation session to a different portion of the meditation session (e.g., transitioning from the introductory portion to the guided breathing portion or transitioning to another portion of the meditation session).

FIG. 7B also depicts audio schematic 707, which is a schematic representation of some of the characteristics of the audio output by device 702 for the user experience session. Audio schematic 707 is not part of the user interface, but is provided for a better understanding of the described techniques. Audio schematic 707 shows a relative position of user 701 and audio output device 703 in physical environment 700 (showing a top-down view of the user's head). Audio schematic 707 also includes audio indicator 711, representing a particular soundscape being output during the meditation session, and spatial audio indicators 709-1 and 709-2, indicating perceived locations of the audio for the meditation session relative to the location of the user's head (the location of the audio as perceived by user 701 while the audio is played using audio output device 703). In the embodiment depicted in FIG. 7B, the audio is output in stereo. Accordingly, spatial audio indicator 709-1 represents the perceived location of a channel of the audio (e.g., left channel and/or first channel) adjacent the left side of the user's head, and spatial audio indicator 709-2 represents the perceived location of another channel of the audio (e.g., right channel and/or second channel) adjacent the right side of the user's head. Thus, as depicted in FIG. 7B, user 701 is facing forward (e.g., facing physical environment 700 as shown in FIG. 7A or/or facing device 702), and device 702 is causing the soundscape of the meditation session to be played in stereo using audio output device 703. In some embodiments, the audio output in the embodiment depicted in FIG. 7B is a preview of the soundscape that will be played during the meditation session (e.g., after the introductory portion, during the guided breathing portion, during the reflection portion, and/or during the outro portion). In some embodiments, the soundscape is played having different audio characteristics during the preview than during the meditation session. For example, the audio is output at a lower volume as indicated by the smaller size of audio indicator 711 in FIG. 7B (compared to in FIG. 7D). As another example, the soundscape is output in stereo rather than in a full, audio immersion having three-dimensional, perceived spatial locations (referred to herein as "spatial audio"), as illustrated in FIG. 7D and discussed below.

In some embodiments, device 702 creates the soundscape for a particular user experience session using a collection of curated sound components. The device assembles the sound components to provide a harmonious audio experience for the user. In some embodiments, the soundscape for a particular user experience session is created to convey a particular mood or theme. For example, for the meditation session, the soundscape is created to provide relaxing audio that helps the user to focus on their breathing rhythm or a particular theme or topic. In some embodiments, device 702 randomly (or pseudorandomly) selects the sound components to create the soundscape. In some embodiments, the sound components are randomly selected, but with a bias towards not repeating a previously created or previously used soundscape. In some embodiments, the sound components that are available for creating a respective soundscape are selected to be harmonious when played together at randomly selected times. In some embodiments, the sound components selected for the soundscape repeat on loop for the user experience session or for a portion of the user experience session. In some embodiments, device 702 introduces a randomly (or pseudorandomly) generated sound component that is played at various (in some embodiments, random) moments throughout the soundscape in order to introduce variety to the soundscape. In some embodiments, a soundscape has a common start and ending sound. In some embodiments, the audio characteristics for the soundscape change based on animation of virtual object 710. For example, the audio volume modulates with the pulsing animation of virtual object 710, increasing as virtual object 710 expands, and decreasing when virtual object 710 contracts. In some embodiments, a spatial location of the audio changes with the pulsing animation of virtual object 710. For example, the audio sounds like it is moving closer towards the user when the object expands, and sounds like it is moving away from the user when the object contracts.

In FIG. 7B, device 702 detects input 722 on options element 720 and, in response, displays options menu 730, as shown in FIG. 7C. Options menu 730 is a user interface for customizing various settings of the meditation session. Options menu 730 includes duration options 732, cadence options 734, and guide options 736. Duration options 732 are selectable to set a duration for the meditation session. As shown in FIG. 7C, duration option 732-2 is currently selected, and the duration of the meditation session is set for 10 minutes. Other available duration options include a five-minute duration option 732-1 and a fifteen-minute duration option 732-3. Cadence options 732 are selectable to set a defined breathing cadence for the mediation session. In some embodiments, animated effects, such as the pulsating rhythm of virtual object 710, are based on the selected breathing cadence. As shown in FIG. 7C, cadence option 734-2 is currently selected, and the breathing cadence is set to seven breaths per minute (bpm). Other available cadence options include a five bpm cadence option 734-1 and a ten bpm cadence option 734-3. Guide options 736 are selectable to choose a coach for the meditation session. The selected coach is associated with one or more audio recordings that device 702 outputs as part of the soundscape during the meditation session (e.g., audio guidance 740 and/or other audio recording), providing user 701 with instruction, encouragement, and/or guidance for the meditation session. In some embodiments, the audio recordings are comprised of different scripts recorded by the coach for playback during various portions of a meditation session. Each coach has their own distinct voice with a speaking cadence, tone, intonation, accent, and other speech characteristics that are unique to the selected coach. As shown in FIG. 7C, coach option 736-1 is currently selected, indicating that a male coach is selected for the meditation session. The other available coach option is female coach option 736-2.

While device 702 is displaying options menu 730, device 702 continues to display virtual object 710 with the animated, pulsating effect represented by lines 714. In FIG. 7C, virtual object 710 is displayed having the expanded state, as indicated by the increased spacing between particles 712 and the increased size of particles 712 (when compared to FIG. 7B). In some embodiments, the spacing of the particles changes without changing the size of the particles. Device 702 continues to output the preview of the soundscape in stereo at audio output device 703.

In FIG. 7C, device 702 detects input 731 selecting five-minute duration option 732-1, input 733 selecting five bpm cadence option 734-1, and input 735 selecting female coach option 736-2. In response to the respective inputs, device 702 updates the settings for the meditation session based on the selected options. Specifically, the duration of the meditation session is changed from ten minutes to five minutes, the breathing cadence is changed from 7 bpm to 5 bpm, and the coach is changed from the male coach to the female coach. Device 702 then detects input 739 selecting done affordance 738. In response to detecting input 739, device 702 displays menu 715, similar to that shown in FIG. 7B, but updated based on the selected options. For example, options element 720 is updated to show the selected duration of five minutes and to include a representation of the female coach. Device 702 continues to display the animated movement of virtual object 710 pulsating in rhythm with the selected breathing cadence, which is now changed to five bpm.

FIGS. 7D and 7E illustrate an embodiment in which device 702 outputs a second portion (e.g., a guided breathing portion, a portion after the introductory portion, and/or a non-introductory portion) of the meditation session in response to an input (e.g., input 724 and/or an audio input) selecting start element 725, with the changes selected in FIG. 7C. When the user selects start element 725, device 702 transitions from the introductory portion of the meditation session to the guided breathing portion of the meditation session shown in FIGS. 7D and 7E. When transitioning from the introductory portion to the guided breathing portion of the meditation session, device 702 increases the user's visual and audio immersion by displaying virtual object 710 growing to a larger size, increasing dimming effect 704, and transitioning from outputting the audio in stereo to outputting spatial audio. During the transition, device 702 increases dimming effect 704 by gradually increasing opacity of the dimming effect from, for example, 2% to 95% or 5% to 90%, and displays virtual object 710 and, optionally, particles 712 growing to a larger average size than in the introductory portion. In some embodiments, virtual object 710 and particles 712 are output as three-dimensional objects. In some embodiments, the transition from the introductory portion to the guided breathing portion includes displaying the virtual object and particles transitioning from two-dimensional objects to three-dimensional objects. In some embodiments, other visual characteristics of virtual object 710 and particles 712 change during the transition. For example, the objects are displayed having an increased brightness, translucence, and/or with a changed reflection of simulated or detected light. Device 702 increases the user's audio immersion by outputting the soundscape at audio output device 703 having an audio effect whereby the audio gradually increases in volume (as indicated by the larger size of audio indicator 711) and sounds as if it is moving from the right and left stereo locations to different perceived locations around the user, as discussed in greater detail below. In some embodiments, device 702 outputs, via audio output device 703, a starting sound such as, for example, a ding or chime to indicate the transition from the introductory portion to the guided breathing portion. In some embodiments, device 702 outputs, via audio output device 703, the same ding or chime sound when transitioning to an outro portion of the meditation session.

In the guided breathing portion, device 702 provides a combination of visual and audio effects to help user 701 focus their breathing to a controlled breathing rate. Device 702 displays virtual object 710 and, optionally, particles 712 having a larger average size than in the introductory portion. In some embodiments, device 702 displays particles 712 spaced apart a greater amount (e.g., a greater average amount and/or a greater instantaneous amount) than during the introductory portion. During the guided breathing portion of the meditation session, device 702 displays virtual object 710 expanding and contracting at a rate that is set by the selected breathing cadence, and outputs (e.g., using audio output device 703 and/or an audio generation component integrated into an HMD) audio guidance 740 instructing user 701 to control their breathing to match the selected breathing cadence. For example, because the user changed the breathing cadence to 5 bpm with input 733, device 702 displays virtual object 710 expanding and contracting at a rate that matches a breathing cadence of five breaths per minute, and outputs the soundscape with audio characteristics that encourage the user to conform their own breathing rate to match the selected breathing cadence of five breaths per minute. In some embodiments, virtual object 710 changes to a different (e.g., expands to a larger or contracts to a smaller) size in the guided breathing portion than during the introductory portion of the meditation session.

FIGS. 7D and 7E depict various moments of the guided breathing portion of the meditation session. Specifically, FIG. 7D depicts the contracted state of virtual object 710, which coincides with the expectation that user 701 is exhaling, or has just finished exhaling, and is about to inhale. While the virtual object is displayed in the contracted state, device 702 outputs the soundscape with audio guidance 740-1 in the voice of the female coach (selected via input 735), instructing the user to inhale. Device 702 then displays virtual object 710 expanding at a steady rate (presumably, while the user is inhaling) until it reaches the expanded state, as depicted in FIG. 7E, which coincides with the expectation that user 701 has inhaled and is about to exhale. Device 702 then outputs, at audio output device 703, audio guidance 740-2, instructing user 701 to begin exhaling. Device 702 then displays virtual object 710 contracting at a steady rate (presumably, while the user is exhaling) until it reaches the contracted state, as depicted in FIG. 7D. This process repeats during the guided breathing portion of the meditation session. In some embodiments, the process is repeated for a predetermined amount of time (e.g., half or 1/3 of the duration selected in FIG. 7C). In some embodiments, the process is repeated for a predetermined number of breathing cycles (e.g., seven breaths in and seven breaths out or ten breaths in and ten breaths out). In some embodiments, the process is repeated until device 702 determines that user 701 has matched their breathing rhythm to the selected breathing cadence. In some embodiments, device 702 includes sensors and/or cameras that are used to detect the user's breathing rhythm to determine whether the user's breathing rhythm matches the selected breathing cadence.

During the guided breathing portion of the meditation session, device 702 continues to output the soundscape (represented, at least partially, by audio indicator 711) as the device outputs audio guidance 740 and displays virtual object 710 expanding and contracting at the selected breathing cadence. In some embodiments, one or more components of the soundscape audio is output as spatial audio. For example, as shown in FIG. 7D, audio schematic 707 includes spatial audio indicators 709-3 to 709-9, each representing a perceived location of the audio (e.g., the soundscape and/or audio guidance) for the meditation session relative to the location of the user's head. Thus, during the guided breathing portion of the meditation session, user 701 perceives the audio as being located at multiple points around the user's head. In some embodiments, the spatial location of the audio changes during the meditation session. For example, as virtual object 710 is expanding, device 702 adjusts the spatial location of the audio to sound as if particles 712 are moving closer towards user 701, and as virtual object 710 is contracting, device 702 adjusts the spatial location of the audio to sound as if particles 712 are moving away from user 701. This movement of the spatial audio is represented by audio indicators 709-3 to 709-9 having a location closer to the user's head in FIG. 7E and a location farther from the user's head in FIG. 7D. In some embodiments, device 702 outputs sound effects as part of the soundscape. In some embodiments, parts of the soundscape are selected based on an animated effect of the virtual object and/or particles. For example, the soundscape may include an increasing whooshing sound as virtual object 710 expands and particles 712 move closer towards user 701, and a decreasing whooshing sound as the particles move away from user 701 as the virtual object contracts.

FIGS. 7F-7H depict an embodiment in which device 702 has transitioned from the guided breathing portion to a third portion (e.g., a reflection portion and/or a portion after the guided breathing portion) of the meditation session. Device 702 transitions from the guided breathing portion of the meditation session to the reflection portion and displays the virtual object in an exploded state in which particles 712 are displayed in a three-dimensional arrangement, as depicted in FIG. 7F. In some embodiments, device 702 displays the transition with an animated effect depicting particles 712 expanding from a configuration that forms virtual object 710, to the exploded, three-dimensional arrangement depicted in FIG. 7F.

In the reflection portion, device 702 prompts user 701 to focus on or contemplate a particular topic or theme, and provides a combination of visual and audio effects to provide a soothing, relaxing environment to help the user focus on the topic. In some embodiments, the reflection portion builds on the relaxation of user 701 achieved during the guided breathing portion of the meditation session. During the reflection portion, device 702 continues to output the soundscape and displays particles 712 moving based on detecting the user breathing. When device 702 detects user 701 inhaling, the device displays particles 712 moving towards and/or around user 701. When device 702 detects user 701 exhaling, the device displays particles 712 moving away from user 701. FIGS. 7F and 7G depict examples of the displayed state of the meditation session based on detecting the user breathing. In some embodiments, device 702 displays the particles moving based on detecting a different biometric input such as heartrate, brain waves, or walking pace.

For example, FIG. 7F depicts particles 712 in the XR environment before the user inhales (or after exhaling), and FIG. 7G depicts particles 712 in the XR environment after the user inhales (or before exhaling). In response to detecting the user inhaling, device 702 displays particles 712 moving towards user 701, for example, from the arrangement in FIG. 7F to the arrangement in FIG. 7G. Conversely, when device 702 detects the user exhaling, the device displays particles 712 moving away from user 701, for example, from the arrangement in FIG. 7G to the arrangement in FIG. 7F. In general, the process continues, moving the particles based on the user's detected breathing, for the duration of the reflection portion of the meditation session.

The embodiments depicted in FIGS. 7F and 7G are provided as non-limiting examples of the movement of particles 712 in response to detected breathing of user 701. In some embodiments, device 702 displays the particles moving in a different manner based on the user's breath. For example, in some embodiments, the magnitude of movement of particles 712 is based on the magnitude and/or duration of the user's breath (inward and/or outward). Thus, if the device detects the user inhale at a greater magnitude and/or duration than in the example discussed above, device 702 displays particles 712 with greater amounts of movement toward user 701 than shown in FIG. 7G. Similarly, if the device detects the user inhale at a lesser magnitude and/or duration than in the example discussed above, device 702 displays particles 712 with less movement toward user 701 than shown in FIG. 7G. In some embodiments, the displayed movement of the particles away from the user varies analogously based on the magnitude and/or duration of the user exhaling, as detected by device 702.

In some embodiments, device 702 displays particles 712 moving at a greater speed of movement when the user exhales, than when the user inhales (or vice versa). In some embodiments, device 702 displays particles 712 in a three-dimensional arrangement, with some particles displayed to appear closer to user 701 and some particles displayed to appear farther from user 701. For example, in FIG. 7F, particle 712-1 is displayed to appear closer to user 701 than particle 712-2. In some embodiments, when the user breathes, the particles that are displayed closer to user 701 are shown with a greater amount (e.g., distance and/or magnitude) of movement in the XR environment than the particles that are displayed farther from user 701. In some embodiments, device 702 displays particles 712 having a floating or swaying movement when they are not moving based on the user's breathing (e.g., between the user's breaths and/or when the user's breath is below a threshold magnitude). In some embodiments, device 702 displays particles 712 moving in accordance with a simulated physical parameter such as a simulated inertia, spring constant, friction, and the like. In some embodiments, device 702 displays particles 712 moving off-screen or on-screen when the user breathes. For example, when device 702 detects the user inhaling, the device displays particles 712 moving towards the user, with some particles, or portions thereof, moving off-screen as the user is inhaling, simulating the particles moving past the user and/or out of the user's field-of-view. Similarly, when device 702 detects the user exhaling, the device displays particles 712 moving away from the user, with some particles or portions of particles moving on-screen, simulating the particles moving into the user's field-of-view.

During the reflection portion of the meditation session, device 702 continues to output the soundscape (represented, at least partially, by audio indicator 711) as the device outputs audio guidance 740 and displays particles 712 moving based on detected user breathing. In some embodiments, when the reflection portion starts, device 702 outputs audio guidance 740-3 prompting the user (in the voice of the coach) to focus on a particular topic or theme. Device 702 outputs the soundscape in spatial audio, and adjusts audio characteristics of the soundscape during the reflection portion of the meditation session. For example, as particles 712 are moving towards the user, device 702 adjusts the spatial locations of the audio to sound as if particles 712 are moving closer towards user 701, and as particles 712 are moving away from the user, device 702 adjusts the spatial locations of the audio to sound as if particles 712 are moving away from user 701. For example, in FIG. 7F, the audio schematic 707 shows spatial audio indicators 709-3 to 709-9 positioned to the side and front of the representation of the user's head, indicating that the audio is perceived to originate at locations in front of and to the side of the user's head. As the user inhales, and particles 712 are displayed moving towards and around user 701 as shown in FIG. 7G, device 702 adjusts the spatial locations of the audio to sound as if particles 712 are moving around (including behind) the user's head, as indicated by the locations of spatial audio indicators 709-3 to 709-9 in FIG. 7G. As the user exhales, and particles 712 are displayed moving away from user 701 to the arrangement shown in FIG. 7F, device 702 adjusts the spatial locations of the audio to sound as if the particles are moving back to the locations to the side and front of the user, as depicted in FIG. 7F.

In some embodiments, device 702 continues the reflection portion of the meditation session for a predetermined amount of time (e.g., half or 1/3 of the duration selected in FIG. 7C), continuing to modify the displayed state of the particles based on detected user breathing. In some embodiments, the reflection portion continues for a predetermined number of breathing cycles (e.g., seven breaths in and seven breaths out or ten breaths in and ten breaths out). In some embodiments, the process continues until device 702 determines that user 701 is no longer focused on the meditation session or has indicated that the user wishes to end the meditation session.

FIG. 7H depicts an embodiment in which device 702 has detected that the user is not focused on the meditation session. As shown in FIG. 7H, user 701 has shifted their focus from the meditation session, rotating their head and the position of device 702 to look at person 745 located in physical environment 700. In some embodiments, device 702 determines whether or not the user is focused on the mediation session by detecting different attention- or focus-based indicators such as the user's gaze, breathing rhythm, heartrate, brainwaves, body movement, movement of device 702, detected sound (e.g., the sounds of another person nearby, sounds in the background, and/or sounds indicating movement or fidgeting of the user), and/or other input that is detected by device 702 and indicative of the user being distracted. In some embodiments, device 702 detects that the user is distracted when the user's focus has drifted from the meditation session for at least a threshold amount of time (e.g., a non-zero amount of time, 2 seconds, and/or 5 seconds). In some embodiments, device 702 detects that the user has regained focus based on detecting the attention- or focus-based indicators. For example, in some embodiments, device 702 determines that the user has regained focus when they have returned to the position they were in before becoming distracted (e.g., facing forward and/or eyes focused on the particles in the XR environment) and their breathing has resumed the breathing rate from before being distracted.

In some embodiments, when device 702 detects user 701 is distracted, device 702 prompts the user to focus on the meditation session. For example, as shown in FIG. 7H, device prompts the user to focus on their breathing, as indicated by audio guidance 740-4. In some embodiments, device 702 pauses the meditation session (e.g., pausing movement of particles 712 and/or modifying or pausing output of the soundscape) when the user is distracted. In some embodiments, device 702 continues the current portion of the meditation session when the device determines that the user has regained focus. In some embodiments, device 702 returns to the guided breathing portion of the meditation session to help the user regain focus. FIG. 7H shows that the user has become distracted during the reflection portion, however, the device is capable of detecting that the user is distracted in other portions of the meditation session such as, for example, the guided breathing portion. In such embodiments, the device pauses the guided breathing portion and encourages the user to focus on the meditation session in a manner similar to that described above for the distraction occurring during the reflection portion.

In some embodiments, the user's location (as approximated, for example, by the location and/or position of device 702) and the virtual objects in the XR environment (e.g., virtual object 710 and/or particles 712) are world-locked. For example, in FIG. 7H, as the user rotates the position of device 702, device 702 displays particles 712 from the changed perspective of device 702 as it has rotated from the position in FIG. 7G to the position in FIG. 7H. For example, device 702 displays particle 712-3 in both FIG. 7G and FIG. 7H. In FIG. 7H, however, because the user has rotated device 702 from the prior position in FIG. 7G, and because the position of the particles 712 is world-locked, particle 712-3 is displayed in FIG. 7H with an orientation that is rotated with respect to the previously displayed orientation of particle 712-3 in FIG. 7G. Thus, as the user rotates or moves device 702, the displayed view of the XR environment changes based on the world-locked configuration. In some embodiments, this world-locked configuration is demonstrated by device 702 modifying the output of the soundscape so as to preserve the spatial audio locations for the soundscape, relative to the XR environment, while the user moves. For example, as shown in FIG. 7H, the user's head is rotated to the left. Instead of keeping the spatial audio locked to the position of the user's head, device 702 adjusts the spatial audio to remain fixed with respect to the XR environment, as indicated by spatial audio indicators 709-3 to 709-9 maintaining their position from FIG. 7G. Accordingly, as the user moves their head, the user perceives the audio has having the same relative location in the XR environment. In some embodiments such as, for example, when device 702 is an HMD, particles 712 are spatially arranged around the viewpoint of user 701 and move relative to the viewpoint of the user as the particles move (e.g., as described with respect to FIGS. 7D, 7E, 7F, 7G, 7H, and/or 7I) in the XR environment.

In some embodiments, user 701 can interact with virtual objects in the XR environment. For example, particles 712 can be reactive to a detected user's location or touch in the XR environment. In some embodiments, device 702 determines that the user's body (e.g., hand, wrist, and/or arm) is co-located with a particle 712 in the XR environment and, in response, displays the particle 712 changing appearance (e.g., changing color, moving based on the user's touch, glowing, and/or becoming more or less translucent). In some embodiments, user 701 can interact with other users in the XR environment. For example, in some embodiments, representation 745a is a virtual representation of person 745, who is sharing the XR environment with user 701. In some embodiments, representation 745a can interact with user 701 and, optionally, view and/or manipulate virtual objects displayed as part of the meditation session.

FIG. 7I depicts device 702 transitioning from the reflection portion to a fourth portion (e.g., an outro portion and/or a portion after the reflection portion) of the meditation session. In some embodiments, the outro portion transitions the user out of the meditation session and brings the user's focus back to the physical world (or to a different experience in the XR environment). In some embodiments, device 702 displays particles 712 moving together (e.g., in an animated flying effect and/or in coordinated movement) to form virtual object 710. In some embodiments, device 702 reduces dimming effect 704 (e.g., reducing opacity of the dimming effect and/or otherwise reducing the dimming effect), thereby increasing visibility of the representation 700a of the physical environment 700 on device 702. In some embodiments, the transition to the outro portion is a reversal of the audio and visual effects provided in the transition from the introductory portion to the guided breathing portion. In some embodiments, device 702 dims the appearance of particles 712 and reduces the movement of the particles 712 from that in the guided breathing and reflection portions of the meditation session. In some embodiments, device 702 displays virtual object 710 pulsating in a manner similar to that in the introductory portion. In some embodiments, device 702 displays virtual object 710 with less movement than in the introductory portion.

As shown in FIG. 7I, when transitioning to the outro portion, device 702 transitions the soundscape audio from the spatial audio output to stereo, gradually decreases the volume of the soundscape (as indicated by the smaller size of audio indicator 711), and outputs audio guidance 740-5, in the coaches voice, prompting the user to increase their awareness of the environment around them. In some embodiments, device 702 outputs, via audio output device 703, a sound effect such as a ding or chime similar to when transitioning from the introductory portion to the guided breathing portion. In some embodiments, device 702 outputs the same audio when transitioning to the outro portion as when transitioning from the introductory portion to the guided breathing portion. In some embodiments, device 702 outputs a same starting sound for each meditation session (e.g., when transitioning from the introductory portion to the guided breathing portion, when ending the introductory portion, and/or when starting the guided breathing portion). In some embodiments, device 702 outputs a same ending sound for each meditation session (e.g., when transitioning to the reflection portion and/or when transitioning to the outro portion). In some embodiments, the starting sound is different from the ending sound for a respective meditation session. In some embodiments, the starting sound is the same as the ending sound, and the sound is different for a plurality of respective meditation sessions or unique for each respective meditation session.

As depicted in FIG. 7I, device 702 displays menu 750 in the outro portion of the meditation session. Menu 750 includes text providing historical data for meditation sessions the user has experienced. Text 754 indicates that user 701 has spent five minutes in a meditation session today, and text 756 indicates that the user has experienced a meditation session at least once for three days in the past week. Other historical data can be provided such as, for example, a number of meditation sessions, a specific amount of time spent for each meditation session, and/or an average amount of time spent in meditation sessions. Menu 750 also includes coach indicator 752 indicating that the female coach provided the audio guidance 740 for the meditation session. Menu 750 includes continue option 758, which is selectable to continue or extend the meditation session. For example, in some embodiments, in response to detecting selection of continue option 758, device 702 resumes the meditation session for a predetermined about of time or until the user indicates they wish to end the meditation session. In some embodiments, when device 702 resumes the meditation session, device 702 returns to the guided breathing portion of the meditation session. In some embodiments, when device 702 resumes the meditation session, device 702 returns to the reflection portion of the meditation session. In some embodiments, device 702 provides user 701 with an option to select whether to return to the guided breathing portion or the reflection portion. Menu 750 also includes done option 760. In some embodiments, when the user selects done option 760, device 702 returns to the introductory portion of the meditation session (e.g., displaying the UI depicted in FIGS. 7B and/or displaying a UI similar to that depicted in FIG. 7B) or exits the meditation application (e.g., displaying a UI similar to that depicted in FIG. 7A or returning to a staging room or virtual home environment in the XR environment).

In some embodiments, the meditation session can be performed in an AR environment or a VR environment. FIGS. 7B-7I depict various embodiments of a meditation session provided in an AR environment, and FIGS. 7J-7L depict various embodiments of different meditation sessions provided in a VR environment. Device 702 can provide the meditation session in a VR environment in a manner that is analogous to the meditation session in the AR environment, but having various differences such as, for example, using a virtual environment, rather than an AR environment. In some embodiments, the visual effects and the soundscapes provided for a meditation session in a VR environment are a subset of the visual effects and soundscapes available for a meditation session in an AR environment. In some embodiments, device 702 automatically selects the visual and audio characteristics based on characteristics of the XR environment. For example, if the XR environment is an AR environment (e.g., the meditation session is provided in an AR environment and/or a portion of the meditation session is provided in an AR environment), device 702 automatically selects the visual and audio characteristics based on various aspects of the AR environment such as, for example, detected lighting conditions, a history of previously used audio and/or visual characteristics for an AR meditation session, or based simply on the fact that the XR environment is AR. As another example, if the XR environment is a VR environment (e.g., the meditation session is provided with a virtual wallpaper and/or the meditation session is provided in a virtual environment), device 702 automatically selects the visual and audio characteristics based on various aspects of the VR environment such as, for example, the scene in the virtual wallpaper, a history of previously used audio and/or visual characteristics for a VR meditation session, or based simply on the fact that the XR environment is VR.

FIG. 7J depicts device 702 displaying an introductory portion of a different meditation session that is to be performed in a VR environment (e.g., a session that occurs after the meditation session depicted in FIGS. 7B-7I or a session that occurs independent of the mediation session depicted in FIGS. 7B-7I). During the VR meditation session, device 702 displays virtual wallpaper 765, providing an opaque virtual background for the meditation session. Device 702 displays virtual wallpaper 765 over a portion of the representation 700a of the physical environment 700. Virtual wallpaper 765 is a virtual interface that depicts a beach scene in FIG. 7J, however, the virtual wallpaper can have different images or background scenes for different meditation sessions. For example, FIG. 7L depicts a different meditation session with virtual wallpaper 787 having a mountain scene. In some embodiments, the user can select the background scene from a collection of background scenes for the virtual wallpaper. In some embodiments, the device 702 randomly selects a background scene from a collection of background scenes (optionally, with a bias towards not repeating a previously used background scene in combination with other visual characteristics such as the virtual object and/or particles).

In the embodiment depicted in FIG. 7J, device 702 displays virtual object 770 having particles 772. Virtual object 770 and particles 772 have different visual characteristics than virtual object 710 and particles 712. For example, virtual object 770 has a generally circular or rounded macro shape. Furthermore, particles 772 are circles or orbs that form virtual object 770 and move around within the shape of virtual object 770. In some embodiments, particles 772 have different material properties than particles 712. For example, particles 772 can have different simulated optical properties, shape, and/or bend, and can have different light properties (e.g., direction, color, and/or intensity) for simulated lights reflected on particles, for example, due to the rounded shape of the particles 772, whereas particles 712 are triangular.

Although virtual object 770 and particles 772 have different visual characteristics than virtual object 710 and particles 712, the virtual objects and particles can exhibit similar behavior based, in some embodiments, on the various portions of the meditation session being output by device 702. For example, device 702 displays virtual object 770 and particles 772 moving rhythmically (e.g., pulsating and/or swaying) in the introductory portion, and expanding to a larger arrangement that moves rhythmically based on a predetermined breathing cadence for the guided breathing portion, similar to virtual object 710 and particles 712. Additionally, device 702 displays particles 772 moving to an exploded state for the reflection portion, and moving based on the user's detected breathing, similar to particles 712. In the outro portion, device 702 displays particles 772 reassembling to form virtual object 770, similar to particles 712 forming virtual object 710, as discussed above with respect to FIG. 7I.

In some embodiments, device 702 selects the visual and audio characteristics of a meditation session to provide a varied user experience for a plurality of meditation sessions and/or a unique user experience for each meditation session. For example, in the embodiments depicted in FIGS. 7J and 7K, device 702 outputs a different soundscape than in the embodiment discussed above with respect to FIGS. 7B-7I, as indicated by audio indicator 774 depicted in FIG. 7J. Audio indicator 774 is similar to audio indicator 711, but has a different appearance (e.g., a different set of music notes and/or different placement) to indicate output of a different soundscape than the soundscape that is output in the meditation session depicted in FIGS. 7B-7I. In some embodiments, device 702 outputs a different soundscape for various meditation sessions. In some embodiments, device 702 selects or creates a soundscape to be harmonious with the visual characteristics. For example, device 702 can select or create a relaxing soundscape to harmonize with a relaxing beach scene and gentle swaying of particles 772.

While device 702 generates or selects different combinations of visual and audio characteristics for respective meditation sessions, some visual and/or audio characteristics can be repeated in some embodiments. For example, the virtual object or particles can have a same appearance in two different meditation sessions, but exhibit different movement characteristics (e.g., swaying in one session and pulsating in the other and/or moving faster/farther in one session as compared to another session). As another example, a same virtual wallpaper can be used in two different meditation sessions, but the virtual object, particles, and/or soundscape are different for the sessions.

In FIG. 7J, device 702 displays menu 767, which is similar to menu 715. Menu 767 includes options element 773, which is similar to options element 720 and can be selected to display an options menu similar to that depicted in FIG. 7C. In the embodiment depicted in FIG. 7J, the meditation session is set for a ten-minute duration with the female coach that was selected for the prior meditation session, as indicated by duration indicator 773-1 and coach indicator 773-2, respectively. Menu 767 also includes start element 776, which is similar to start element 725. In response to detecting a selection of start element 776 via input 778, device 702 transitions from the introductory portion to the guided breathing portion of the meditation session, as depicted in FIG. 7K.

In FIG. 7K, device 702 has transitioned to the guided breathing portion and is displaying virtual wallpaper 765 having an expanded size and displaying virtual object 770 and particles 772 moving based on a predefined breathing cadence, similar to the embodiments discussed above with respect to FIGS. 7D and 7E. Additionally, device 702 has transitioned the soundscape from stereo audio to spatial audio, including gradually increasing the volume, as indicated by the larger displayed size of audio indicator 774.

In some embodiments, different audio guidance is used for each meditation session. For example, although the embodiment of the VR meditation session depicted in FIGS. 7J and 7K uses the same female coach's voice as in the AR meditation session, the audio guidance output by device 702 is different for the various portions of the meditation session. In some embodiments, the audio guidance is selected from a subset of audio recordings of the selected coach that are available for respective portions of the meditation session. Thus, in FIG. 7K, device 702 outputs guidance 780-1, which provides similar instruction as guidance 740-1, but uses different words (and, in some instances, different speaking characteristics such as intonation) because it is a different audio recording than guidance 740-1.

FIG. 7L illustrates an example of different audio and visual characteristics for a different meditation session, illustrating a guided breathing portion of the different meditation session. For example, in FIG. 7L, device 702 displays virtual wallpaper 787, which is similar to virtual wallpaper 765, but having a mountain scene instead of a beach scene. Device 702 also displays virtual object 790 and particles 792 (similar to virtual objects 710 and 770 and particles 712 and 772), which illustrate additional examples of different visual characteristics for a different meditation session. Device 702 also outputs a different soundscape as indicated by audio indicator 794 and audio guidance 785-1, which is similar to audio guidance 740-1 and 780-1, but is a different audio recording, as indicated by the different words included in audio guidance 785-1. In some embodiments, the audio guidance is a different audio recording that uses the same words, but has different audio characteristics such as tone, accent, or cadence.

Additional descriptions regarding FIGS. 7A-7L are provided below in reference to methods 800, 900, and 1000 described with respect to FIGS. 7A-7L.

FIG. 8 is a flow diagram of an exemplary method 800 for providing a computer-generated user experience session with particles that move based on breathing characteristics of a user, in accordance with some embodiments. In some embodiments, method 800 is performed at a computer system (e.g., computer system 101 in FIG. 1 and/or device 702) (e.g., a smartphone, device, and/or head-mounted display generation component) that is in communication with a display generation component (e.g., display generation component 120 in FIGS. 1, 3, and 4 and/or display 702-1) (e.g., a display, a touchscreen, a visual output device, a 3D display, a display having at least a portion that is transparent or translucent on which images can be projected (e.g., a see-through display and/or a transparent display), a projector, a heads-up display, and/or a display controller) and one or more sensors (e.g., camera 702-2) (e.g., a gyroscope, an accelerometer, a motion sensor, a movement sensor, a microphone, an infrared sensor, a camera sensor, a depth camera, a visible light camera, an eye-tracking sensor, a gaze-tracking sensor, a physiological sensor, an image sensor, a camera (e.g., color sensors, infrared sensors, and other depth-sensing cameras) that points downward at a user's hand, and/or a camera that points forward from the user's head). In some embodiments, the method 800 is governed by instructions that are stored in a non-transitory (or transitory) computer-readable storage medium and that are executed by one or more processors of a computer system, such as the one or more processors 202 of computer system 101 (e.g., control 110 in FIG. 1A). Some operations in method 800 are, optionally, combined and/or the order of some operations is, optionally, changed.

In method 800, the computer system (e.g., 702) displays (802) (e.g., in an XR environment, in a non-XR environment), via the display generation component (e.g., 702-1), a user interface for a user experience session (e.g., 705, 765, and/or 787) (e.g., a UI of an application for the XR environment that optionally includes guided instruction for breathing to relax and/or focus the user). While the user experience session is active (e.g., after initiating the user experience session and before the user experience session has ended), the computer system detects (804), via the one or more sensors (e.g., 702-2), one or more breathing characteristics (e.g., whether a user is currently exhaling, whether a user is currently inhaling, a rate of inhaling, a rate of exhaling, a duration of inhaling, a duration of exhaling, a duration of a pause (e.g., after inhaling, after exhaling, during an inhale, during an exhale), a change in a rate of inhaling and/or exhaling, and/or a pattern of inhaling and/or exhaling) of a user (e.g., 701) of the computer system, and displays (806) a user interface object (e.g., 710, 770, and/or 790) (e.g., cube, sphere, orb, cloud, pyramid, and/or abstract object) having a plurality of particles (e.g., 712, 772, and/or 792) that move based on the one or more breathing characteristics of the user of the computer system.

As part of displaying the user interface for the user experience session, and in accordance with a determination that a first breathing event (e.g., as a user inhales, exhales, and/or pauses while breathing) of the user of the computer system satisfies a first set of criteria (e.g., the characteristics of the breathing event indicate the user is inhaling), the computer system (e.g., 702) displays (808) the particles (e.g., 712, 772, and/or 792) of the user interface object (e.g., 710, 770, and/or 790) moving in a first manner (e.g., as depicted in FIG. 7G) (e.g., having a first direction of movement (e.g., expanding away from a fixed point (e.g., in the user's field-of-view)), a first velocity or speed of movement, and/or a first pattern of movement) during the first breathing event of the user of the computer system (e.g., expanding from a fixed point as the user inhales, wherein the particles move at a rate determined based on the rate of the user inhaling).

As part of displaying the user interface for the user experience session, and in accordance with a determination that the first breathing event of the user of the computer system satisfies a second set of criteria (e.g., the characteristics of the breathing event indicate the user is exhaling), the computer system (e.g., 702) displays (810) the particles (e.g., 712, 772, and/or 792) of the user interface object (e.g., 710, 770, and/or 790) moving in a second manner different from the first manner (e.g., as depicted in FIG. 7F) (e.g., having a second direction of movement (e.g., contracting towards a fixed point (e.g., in the user's field-of-view)), a second velocity or speed of movement, and/or a second pattern of movement) during the first breathing event of the user of the computer system (e.g., contracting towards a fixed point as the user exhales, wherein the particles move at a rate determined based on the rate of the user exhaling). Displaying the particles of the user interface object moving in the first manner in accordance with a determination that the first breathing event of the user satisfies a first set of criteria and displaying the particles of the user interface object moving in the second manner in accordance with a determination that the first breathing event of the user satisfies a second set of criteria provides feedback about a state of the computer system (e.g., a state of providing the user experience session).

In some embodiments, the computer system (e.g., 702) is in communication with an audio generation component (e.g., 703) (e.g., a speaker, a bone conduction audio output device, and/or an audio generation component integrated into an HMD). In some embodiments, as part of displaying the user interface for the user experience session, prior to the user experience session being active (e.g., after launching an application that is available for providing the user experience session and before the user experience session is initiated (e.g., started) (e.g., by a user of the computer system)), the computer system concurrently displays, via the display generation component (e.g., 702-1), a representation of the plurality of particles for the user interface object (e.g., particles 712 as depicted in FIGS. 7B and/or 7C, particles 772 as depicted in FIG. 7J, and/or particles 792 as depicted in FIG. 7L) (e.g., a static and/or animated view of the particles before the user experience session starts) and outputs, via the audio generation component, an audio soundscape (e.g., audio 711 as depicted in FIGS. 7B and/or 7C, audio 774 as depicted in FIG. 7J, and/or audio 794 as depicted in FIG. 7L) (e.g., a set of curated sound components automatically and/or manually selected to create an audio environment for the user experience session) for the user experience session. Displaying the representation of the plurality of particles for the user interface object and outputting the audio soundscape for the user experience session prior to the user experience session being active provides feedback about a state of the computer system. For example, the audio and visual feedback indicate to the user what the user experience session will include when active.

In some embodiments, the computer system outputs a portion of the audio soundscape (e.g., a preview of the audio soundscape) prior to the user experience being active and outputs the complete audio soundscape when the user experience is active (e.g., in FIGS. 7D, 7E, 7F, 7G, 7H, 7K, and/or 7L). In some embodiments, outputting the audio soundscape includes outputting the audio soundscape (or a portion of the audio soundscape) with a set of two or more audio components selected randomly or pseudorandomly from a set of available audio components.

In some embodiments, as a part of displaying the user interface for the user experience session, the computer system (e.g., 702) displays a dimmed appearance (e.g., 704) of an environment (e.g., 700*a*) (e.g., a virtual environment and/or the physical environment (e.g., visible via pass-through video and/or due to a transparent nature of the display)) of the user experience (e.g., a fading effect and/or a dimming effect) (e.g., dimming at least a portion of the environment by 0.5%, 1%, 2%, 3%, 5%, 7%, 10%, 15%, 20%, and/or another amount greater than 0%) prior to the user experience session being active (e.g., as depicted in FIGS. 7B and 7C). Displaying the dimmed appearance of the environment prior to the user experience session being active encourages the user of the computer system to focus on the user experience session.

In some embodiments, displaying the dimmed appearance of the environment includes visually obscuring a view of the physical environment (e.g., 700*a*) that is visible (e.g., via pass-through video and/or due to a transparent nature of the display) to a user (e.g., 701) of the computer system (e.g., 702). In some embodiments, displaying the dimmed appearance of the environment includes displaying a virtual overlay (e.g., 704) that is partially transparent to show the physical environment through the virtual overlay. In some embodiments, the dimmed appearance is uniform. In some embodiments, the dimmed appearance is variable.

In some embodiments, displaying the user interface for the user experience session includes, prior to the user experience session being active, the computer system (e.g., 702) displaying a start option (e.g., 725 and/or 776) (e.g., affordance, graphical user interface object, and/or graphical element) that is selectable (e.g., via input 724 and/or input 778) (e.g., via a pinch gesture, a tap input, a gaze gesture, a gaze-and-dwell gesture, and/or other input gestures) to initiate (e.g., start, begin, and/or activate) the user experience session, and displaying an indication (e.g., 720-1, 732-1, 732-2, 732-3, and/or 773-1) of a duration (e.g., 3 minutes, 5 minutes, 10 minutes, 12 minutes, 15 minutes, 20 minutes) of the user experience session (e.g., when the user experience session is active). Displaying the start affordance and the indication of the duration of the user experience session prior to the user experience session being active provides feedback about a state of the computer system. For example, the indication of the duration provides the user with feedback about the selected length of the user experience session. In some embodiments, in response to detecting an input (e.g., 724 and/or 778) (e.g., a pinch gesture, a tap input, a gaze gesture, a gaze-and-dwell gesture, and/or other input gestures) directed to the start option, the computer system initiates the user experience session.

In some embodiments, displaying the user interface for the user experience session includes: prior to the user experience session being active, the computer system (e.g., 720) displaying a set of one or more duration options (e.g., 732, 732-1, 732-2, and/or 732-3) that are selectable (e.g., via a pinch gesture, a tap input, a gaze gesture, a gaze-and-dwell gesture, and/or other input gestures) to modify the duration of the user experience session (e.g., a duration of at least a portion of the user experience session such as a guided breathing portion and/or a reflection portion). The computer system detects an input (e.g., 731) (e.g., a pinch gesture, a tap input, a gaze gesture, a gaze-and-dwell gesture, and/or other input gestures) directed to a first duration option (e.g., 732-1), of the set of one or more duration options, that is selectable to modify the duration of the user experience session, and in response to detecting the input directed to the first duration option of the set of one or more duration options, the computer system selects (e.g., modifying and/or setting based on the detected input) a duration of the user experience session of a first duration (e.g., 5 minutes or 10 minutes) (e.g., modifying from a default duration of 1 minute or modifying from a previously selected duration of 20 minutes). In some embodiments, detecting an input directed to a second duration option causes the computer system to set a duration of a second duration, different from the first duration. Modifying the duration of the user experience session to the first duration in response to detecting the input directed to the first duration option causes the computer system to automatically optimize the user experience session to meet a requested duration provided by a user of the computer system.

In some embodiments, displaying the user interface for the user experience session includes: prior to the user experience session being active, the computer system (e.g., 702) displays a set of one or more audio options (e.g., 736, 736-1, and/or 736-2) that are selectable (e.g., via a pinch gesture, a tap input, a gaze gesture, a gaze-and-dwell gesture, and/or other input gestures) to choose an audio guide (e.g., an audio source, a narrator, speaker, coach, and/or person) from a plurality of audio guides for the user experience session. The computer system detects an input (e.g., 735) directed to a first audio option (e.g., 736-2), of the set of one or more audio options, that is selectable to choose an audio guide from the plurality of audio guides for the user experience session. In response to detecting the input directed to the first audio option, the computer system selects a first audio guide from the plurality of audio guides for the user experience session (e.g., and optionally unselects a second audio guide for the user experience session). Selecting the first audio guide for the user experience session in response to detecting the input directed to the first audio option that is selectable to choose an audio guide causes the computer system to automatically optimize the user experience session to provide a requested audio guide for the user experience session. In some embodiments, in response to detecting input directed to a second audio option (e.g., 736-1), the computer system selects a second audio guide, different from the first audio guide, for the user experience session. In some embodiments, the selected audio guide provides the user with verbal instruction, encouragement, coaching, cues, and/or guidance for experiencing the user experience session.

In some embodiments, displaying the user interface for the user experience session includes: while the user experience session is active (e.g., after (in response to) starting the user experience session; and/or in a first phase or portion of the user experience session (e.g., a phase or portion of the user experience session that is before a subsequent phase or portion of the user experience session)), the computer system (e.g., 702) displays the user interface object (e.g., 710, 770, and/or 790) with an animated effect (e.g., an animated movement of the user interface object and/or the particles of the user interface object) (e.g., a pulsating animation (e.g., a repeating, alternating pattern of increasing the size of (e.g., expanding) the user interface object and decreasing the size of (e.g., contracting) the user interface object)) that is based on a predetermined biometric rhythm (e.g., a breathing cadence (e.g., a pattern of inhaling and exhaling)) (e.g., 3 breaths per minute, 5 breaths per minute, 7 breaths per minute, 10 breaths per minute) (e.g., as depicted in FIGS. 7D, 7E, and/or 7K). In some embodiments, the predetermined biometric rhythm is a default setting that is set by an application for providing the user experience session and/or by an operating system of the computer system. In some embodiments, the predetermined biometric rhythm is a user-selected setting. In some embodiments, the predetermined biometric rhythm includes heart rate. In some embodiments, the predetermined biometric rhythm includes a walking pace. Displaying the user interface object with the animated effect that is based on a predetermined biometric rhythm includes: in accordance with a determination (e.g., based on one or more settings of the user experience session) that the predetermined biometric rhythm is a first biometric rhythm (e.g., 5 breaths per minute (e.g., inhaling then exhaling (optionally pausing in between) five times in one minute) or 6 breaths per minute), the computer system animates the user interface object based on a first pattern that corresponds to the first biometric rhythm (e.g., expanding the user interface object with the inhaling portion of the breathing cadence and contracting the user interface object with the exhaling portion of the breathing cadence and/or rotating the user interface object in a first direction with the inhaling portion of the breathing cadence and rotating the user interface object in a second direction with the exhaling portion of the breathing cadence), and in accordance with a determination that the predetermined biometric rhythm is a second biometric rhythm different from the first biometric rhythm (e.g., 7 breaths per minute (e.g., inhaling then exhaling (optionally pausing in between) seven times in one minute) or 8 breaths per minute), the computer system animates the user interface object based on a second pattern that corresponds to the second biometric rhythm (e.g., expanding the user interface object with the inhaling portion of the breathing cadence and contracting the user interface object with the exhaling portion of the breathing cadence and/or rotating the user interface object in a first direction with the inhaling portion of the breathing cadence and rotating the user interface object in a second direction with the exhaling portion of the breathing cadence). Animating the user interface object based on the first pattern that corresponds to the first biometric rhythm in accordance with a determination that the predetermined biometric rhythm is the first biometric rhythm, and animating the user interface object based on the second pattern that corresponds to the second biometric rhythm in accordance with a determination that the predetermined biometric rhythm is the second biometric rhythm, provides feedback about a state of the computer system.

In some embodiments, the predetermined biometric rhythm is a biometric rhythm that is selected (e.g., via input 733) by a user (e.g., 701) of the computer system (e.g., 702) (e.g., a user-selectable or customizable setting). In some embodiments, the first biometric rhythm is a default biometric rhythm (e.g., the biometric rhythm is set by an application for providing the user experience session and/or by an operating system of the computer system), and the second biometric rhythm is a biometric rhythm that is selected by a user of the computer system (e.g., a user-selectable or customizable setting). In some embodiments, both the first biometric rhythm and the second biometric rhythm are user-selectable settings.

In some embodiments, the computer system (e.g., 702) is in communication with an audio generation component (e.g., 703) (e.g., a speaker, a bone conduction audio output device, and/or an audio generation component integrated into an HMD). In some embodiments, while the user experience session is active, the computer system outputs an audio component (e.g., 711, 774, and/or 794) (e.g., one or more audio components of a soundscape that is selected (e.g., automatically) for the user experience session) that has a perceived spatial location (e.g., 709-3 to 709-9) that moves (e.g., automatically) (e.g., relative to the location of the user) based on the one or more breathing characteristics of the user of the computer system (e.g., as depicted in FIGS. 7D, 7E, 7F, 7G, 7H, and/or 7K). In accordance with a determination that a second breathing event (in some embodiments, the second breathing event is the first breathing event) of the user (e.g., 701) of the computer system satisfies a third set of criteria (in some embodiments, the third set of criteria is the first set of criteria), the computer system outputs the audio component with a first perceived spatial location relative to the user of the computer system (e.g., 709-3 to 709-9 as depicted in FIG. 7G). In accordance with a determination that the second breathing event of the user of the computer system satisfies a fourth set of criteria (in some embodiments, the fourth set of criteria is the second set of criteria), the computer system outputs the audio component with a second perceived spatial location relative to the user of the computer system that is different from the first perceived spatial location (e.g., 709-3 to 709-9 as depicted in FIG. 7F). Outputting the audio component with first perceived spatial location relative to the user of the computer system in accordance with a determination that the second breathing event satisfies the third set of criteria, and outputting the audio component with the second perceived spatial location relative to the user in accordance with a determination that the second breathing event satisfies the fourth set of criteria, causes the computer system to automatically adjust the spatial location of the audio component based on a detected breathing event of the user of the computer system.

In some embodiments, the spatial location of the audio component changes in conjunction with changes in breathing events. In some embodiments, the perceived spatial audio location of the audio component changes with the movement of the particles of the user interface object. For example, as the particles move in the first manner (e.g., expanding away from the fixed point), the perceived spatial audio location moves towards the user of the computer system and, as the particles move in the second manner (e.g., contracting towards the fixed point), the perceived spatial audio location moves away from the user of the computer system.

In some embodiments, a portion of a physical environment (e.g., 700) of the user (e.g., 701) of the computer system (e.g., 702) is visible (e.g., 700a) (e.g., displayed via pass-through video and/or visible due to a transparent nature of the display) prior to the user experience session being active. In some embodiments, the computer system initiates (e.g., starts, begins, and/or activates) the user experience session. In some embodiments, as part of initiating the user experience session, the computer system displays, via the display generation component (e.g., 702-1), a dimming effect (e.g., 704) (e.g., a fading effect) (e.g., dimming by 99.9%, 99%, 98%, 97%, 95%, 90%, 85%, 80%, and/or another amount less than 100%) that gradually decreases visibility of the physical environment (e.g., as depicted in FIGS. 7B, 7C, and/or 7D) (e.g., the visibility of the physical environment is decreased (e.g., 50% visible) at a first time, is further decreased (e.g., 25% visible) at a second time after the first time, is further decreased (e.g., 10% visible) at a third time after the second time, and is further decreased (e.g., 2% visible) at a fourth time after the third time). Displaying the dimming effect that gradually decreases visibility of the physical environment reduces distractions and encourages the user of the computer system to focus on the user experience session.

In some embodiments, displaying the dimming effect (e.g., 704) includes visually obscuring a view of the physical environment (e.g., 700a) that is visible (e.g., via passthrough video and/or due to a transparent nature of the display) to a user of the computer system (e.g., 702). In some embodiments, displaying the dimming effect includes displaying a virtual overlay that is partially opaque and increases in opacity to reduce the visibility of the physical environment through the virtual overlay, thereby causing an effect whereby the physical environment appears to fade out of view (or to being faintly visible). In some embodiments, the dimming effect is uniform. In some embodiments, the dimming effect is variable.

In some embodiments, while the user experience session is active, the computer system (e.g., 702) detects, via the one or more sensors (e.g., 702-2), one or more focus-based characteristics of the user (e.g., 701) of the computer system (e.g., one or more biometric characteristics (e.g., head movement, body movement, breathing rate, heart rate, and/or eye gaze) and/or user inputs that are indicative of whether the user is focusing their attention on the user experience session (e.g., breathing and/or listening to audio guidance) and/or indicating a particular level of focus on the user experience session), and outputs feedback (e.g., 740-4) (e.g., audio feedback and/or visual feedback) based on the one or more focus-based characteristics of the user of the computer system (e.g., as depicted in FIG. 7H). Outputting feedback based on the one or more focus-based characteristics of the user of the computer system enables the computer system to automatically encourage the user of the computer system to participate in the user experience session and provides the user with feedback about the detected focus-based characteristics.

In some embodiments, outputting feedback based on the one or more focus-based characteristics of the user (e.g., 701) of the computer system (e.g., 702) includes displaying, via the display generation component, visual feedback (e.g., movement of the particles (e.g., 712, 772, and/or 792) of the user interface object and/or text indicating the level of user focus) based on the one or more focus-based characteristics of the user of the computer system. Displaying visual feedback based on the one or more focus-based characteristics of the user of the computer system enables the computer system to automatically encourage the user of the computer system to participate in the user experience session and provides the user with visual feedback about the detected focus-based characteristics. In some embodiments, the visual feedback includes movement of the particles of the user interface object when the one or more focus-based characteristics of the user indicate that the user is focusing on the user experience session. In some embodiments, the visual feedback includes suspension (e.g., temporarily pausing) of the movement of the particles when the one or more focus-based characteristics of the user indicate that the user is not focusing on the user experience session (e.g., as depicted in FIG. 7H).

In some embodiments, displaying visual feedback based on the one or more focus-based characteristics of the user (e.g., 701) of the computer system (e.g., 702) includes: in accordance with a determination that the one or more focus-based characteristics of the user of the computer system satisfy a first set of focus criteria (e.g., one or more biometric characteristics of the user (e.g., head movement, body movement, breathing rate, heart rate, and/or eye gaze) indicate the user is focusing their attention on the user experience session (e.g., breathing and/or listening to audio guidance)) (in some embodiments, and in accordance with a determination that the first breathing event of the user satisfies the first set of criteria), displaying the particles (e.g., 712, 772, and/or 792) of the user interface object moving away from a reference location (e.g., the user's viewpoint or a predefined location) during an outward breath (e.g., exhale) of the user of the computer system (e.g., as depicted in FIG. 7F). Displaying the particles of the user interface object moving away from the reference location during the outward breath of the user of the computer system provides feedback about a state of the computer system (e.g., a state in which the displayed particles are reactive to a detected outward breath of the user). In some embodiments, displaying the particles of the user interface object moving in the first manner during the first breathing event of the user includes displaying the particles moving away from reference location during an outward breath.

In some embodiments, displaying visual feedback based on the one or more focus-based characteristics of the user of the computer system includes: in accordance with a determination that the one or more focus-based characteristics of the user of the computer system satisfy the first set of focus criteria (e.g., one or more biometric characteristics of the user (e.g., head movement, body movement, breathing rate, heart rate, and/or eye gaze) indicate the user is focusing their attention on the user experience session (e.g., breathing and/or listening to audio guidance)) (in some embodiments, and in accordance with a determination that the first breathing event of the user satisfies the second set of criteria), displaying the particles (e.g., 712, 772, and/or 792) of the user interface object moving toward the reference location (e.g., the user's viewpoint or a predefined location) during an inward breath (e.g., inhale) of the user of the computer system (e.g., as depicted in FIG. 7G). Displaying the particles of the user interface object moving toward the reference location during the inward breath of the user of the computer system provides feedback about a state of the computer system (e.g., a state in which the displayed particles are reactive to a detected inward breath of the user). In some embodiments, displaying the particles of the user interface object moving in the second manner during the first breathing event of the user includes displaying the particles moving toward the reference location during an inward breath.

In some embodiments, the computer system (e.g., 702) displays particles (e.g., 712, 772, and/or 792) of the user interface object moving at a first rate toward the reference location during the inward breath. In some embodiments, the computer system displays the particles of the user interface object moving at a second rate away from the reference location during the outward breath. In some embodiments, the second rate is different from (e.g., slower than; faster than) the first rate. In some embodiments, the second rate is different from the first rate regardless of the characteristics (e.g., speed, volume, and/or duration) of the inward breath and the outward breath.

In some embodiments, the reference location is a world-locked (e.g., environment-locked) location corresponding to a viewpoint of the user (e.g., 701) of the computer system (e.g., 702) in a physical environment (e.g., 700) (e.g., the viewpoint of the user is based on (e.g., selected in reference to and/or anchored to) a location and/or object in the three-dimensional environment (e.g., a physical environment or a virtual environment)) (e.g., as depicted in FIG. 7H).

In some embodiments, the computer system (e.g., 702) is in communication with an audio generation component (e.g., 703). In some embodiments, outputting feedback based on the one or more focus-based characteristics of the user of the computer system includes outputting, via the audio generation component, audio feedback (e.g., 740-4)

(e.g., audio guidance instructing the user of the computer system to focus on one or more elements of the user experience session (e.g., breathing and/or listening to the audio) and/or an audio tone) based on the one or more focus-based characteristics of the user of the computer system. Outputting audio feedback based on the one or more focus-based characteristics of the user of the computer system enables the computer system to automatically encourage the user of the computer system to participate in the user experience session.

In some embodiments, the one or more focus-based characteristics of the user (e.g., 701) of the computer system (e.g., 702) includes a plurality of biometric indicators (e.g., gaze (e.g., increased movement/saccades), head pose (significant change in head direction (e.g., rotation and/or tilt)), and/or breath (e.g., increased or irregular frequency)).

In some embodiments, the one or more focus-based characteristics of the user (e.g., 701) of the computer system (e.g., 702) includes an indication of whether a focus of the user has failed to meet focus criteria (e.g., the user's focus has stopped focusing on the user experience session) for a threshold amount of time (e.g., 7 seconds, 8 seconds, 9 seconds, or 10 seconds).

In some embodiments, displaying the particles (e.g., 712, 772, and/or 792) of the user interface object moving in the first manner or in the second manner includes: the computer system (e.g., 702) displaying a first set of one or more particles (e.g., 712-2) having a first distance from a location corresponding to the viewpoint of the user of the computer system and having a first amount of movement during the first breathing event (e.g., as depicted in FIG. 7F or FIG. 7G) (e.g., moving a first distance towards or away from a reference point from the perspective of the user of the computer system), and displaying a second set of one or more particles (e.g., 712-1) different from the first set of one or more particles and having a second distance from the location corresponding to the viewpoint of the user of the computer system, different from (e.g., less than; greater than) the first distance, and having a second amount of movement during the first breathing event different from (e.g., less than; greater than) the first amount of movement (e.g., as depicted in FIG. 7F or FIG. 7G) (e.g., moving a second distance towards or away from a reference point from the perspective of the user of the computer system). Displaying the second set of one or more particles having a second distance from the user different from the first distance and having the second amount of movement during the first breathing event different from the first amount of movement provides feedback about a state of the computer system.

In some embodiments, the first set of one or more particles (e.g., 712-2) are displayed having a perceived distance that is farther from the user than the second set of one or more particles (e.g., 712-1), and the first set of one or more particles move by a lesser amount than the second set of one or more particles during a respective breathing event. In some embodiments, the shorter the distance of a respective particle from the perspective of the user, the greater the amount of movement of the respective particle during a respective breathing event. For example, as the user inhales or exhales, particles that are displayed closer to the user appear (to the user) to move by a greater amount than particles that are displayed farther from the user, and particles that are displayed farther away from the user appear to move by a lessor amount than particles that are displayed closer to the user.

In some embodiments, movement of the plurality of particles (e.g., 712, 772, and/or 792) is based on a set of one or more simulated physical parameters (e.g., inertia, spring constant, and/or friction).

In some embodiments, displaying the user interface for the user experience session includes: while the user experience session is active, the computer system (e.g., 702) detects, via the one or more sensors (e.g., 702-2), gaze data indicative of a gaze of the user (e.g., 701) of the computer system. In some embodiments, while displaying the user interface object having the plurality of particles (e.g., 712, 772, and/or 792) that move based on the one or more breathing characteristics of the user of the computer system, the computer system detects updated gaze data. In some embodiments, in response to detecting the updated gaze data, and in accordance with a determination that the updated gaze data indicates that the gaze of the user exceeds a gaze departure threshold (e.g., the gaze of the user is not focused on or looking at one or more elements (e.g., the particles) of the user experience session for at least a threshold amount of time (e.g., 7 seconds, 8 seconds, 9 seconds, 10 seconds, or 12 seconds)), the computer system pauses the user experience session (e.g., temporarily stopping the user experience session) (e.g., as depicted in FIG. 7H). In some embodiments, in response to detecting the updated gaze data, and in accordance with a determination that the updated gaze data does not indicate that the gaze of the user exceeds the gaze departure threshold, the computer system forgoes pausing the user experience session (e.g., continuing or resuming the user experience session). Selectively pausing the user experience session based on a determination of whether or not the updated gaze data indicates that the gaze of the user exceeds the gaze departure threshold enables the computer system to automatically suspend the user experience session when the user of the computer system is distracted. In some embodiments, pausing the user experience session includes ceasing displaying the user interface object. In some embodiments, pausing the user experience session includes displaying the user interface object in a motionless state. In some embodiments, pausing the user experience session includes outputting an audio instruction to resume focus on the user experience session.

In some embodiments, displaying the user interface for the user experience session includes the computer system (e.g., 702) displaying the user interface (e.g., 705, 710, 712, 770, 772, 790, and/or 794) with a set of visual characteristics (e.g., shape (e.g., cube, sphere, orb, cloud, pyramid, and/or abstract object), components (e.g., particles), and/or visual appearance (e.g., animated effect(s), translucence, movement characteristics, and/or displayed background)) selected randomly or pseudorandomly from a set of available visual characteristics (e.g., a superset of visual characteristics). In some embodiments, the computer system is in communication with an audio generation component (e.g., 703). In some embodiments, the computer system outputs, via the audio generation component, an audio soundscape (e.g., 711, 774, and/or 794) (e.g., a set of curated sound components selected to create an audio environment for the user experience session) for the user experience session, wherein the audio soundscape is output concurrently with displaying the user interface for the user experience session and outputting the audio soundscape includes outputting the audio soundscape with a first set of two or more audio components (e.g., a set of sound components) selected randomly or pseudorandomly from a set of available audio components. Displaying the user interface with a set of visual characteristics selected randomly or pseudorandomly from a set of available visual characteristics and outputting an audio soundscape with the first set of two or more audio components selected randomly or pseudorandomly from a set of available audio components enables the computer system to provide a more realistic user experience while saving storage space by not requiring multiple different complete audio tracks and/or visual components to be stored and selected for playback/display. In some embodiments, the two or more audio components in the first set of audio components is a subset of curated sound components that are selected from a superset of curated sound components for the audio soundscape. Additional aspects of the soundscape are discussed in greater detail below with respect to method 1000.

In some embodiments, displaying the user interface for the user experience session includes, while displaying the user interface object (e.g., 710, 770, and/or 790) having a first displayed state in which the plurality of particles (e.g., 712, 772, and/or 792) are displayed having a first amount of spacing (e.g., a dense, compact, and/or tight grouping of the particles; forming a shape (e.g., orb, cloud, triangle, and/or cube)) for a first portion (e.g., an introductory portion) of the user experience session (e.g., as depicted in FIGS. 7B, 7C, and/or 7J), the computer system (e.g., 702) detects a transition from the first portion of the user experience session to a second portion of the user experience session (e.g., a guided breathing portion of the user experience session). In response to detecting the transition from the first portion of the user experience session to the second portion of the user experience session, the computer system displays the user interface object having (e.g., transitioning to) a second displayed state different from the first displayed state, wherein the plurality of particles are displayed for the second portion of the user experience session having a second amount of spacing (e.g., a loose grouping of particles; a positioning of the particles that is more spaced apart, but still forming a respective shape (e.g., orb, cloud, triangle, and/or cube)) different from (e.g., greater than) the first amount of spacing (e.g., as depicted in FIGS. 7D, 7E, 7K, and/or 7L). Displaying the user interface object having the second displayed state different from the first displayed state in response to detecting the transition from the first portion of the user experience session to the second portion of the user experience session, wherein the plurality of particles are displayed for the second portion of the user experience session having the second amount of spacing different from the first amount of spacing, provides feedback about a state of the computer system (e.g., a state in which the computer system is providing a particular portion of the user experience session).

In some embodiments, displaying the user interface for the user experience session includes: while the computer system (e.g., 702) displays the user interface object (e.g., 710, 770, and/or 790) having the second displayed state (e.g., as depicted in FIGS. 7D, 7E, 7K, and/or 7L), the computer detects a transition from the second portion of the user experience session to a third portion of the user experience session (e.g., a reflection portion of the user experience session). In response to detecting the transition from the second portion of the user experience session to the third portion of the user experience session, the computer system displays the user interface object having (e.g., transitioning to) a third displayed state different from the first and second displayed states, wherein the plurality of particles (e.g., 712, 772, and/or 792) are displayed for the third portion of the user experience session having a third amount of spacing (e.g., a spaced apart positioning of the particles and/or a spacing of the particles that no longer forms a distinct shape) different from (e.g., greater than) the second amount of spacing (e.g., as depicted in FIGS. 7F, 7G, and/or 7H). Displaying the user interface object having the third displayed state different from the first and second displayed states in response to detecting the transition from the second portion of the user experience session to the third portion of the user experience session, wherein the plurality of particles are displayed for the third portion of the user experience session having the third amount of spacing different from the second amount of spacing, provides feedback about a state of the computer system (e.g., a state in which the computer system is providing a particular portion of the user experience session).

In some embodiments, displaying the user interface for the user experience session includes: while the computer system (e.g., 702) displays the user interface object (e.g., 710, 770, and/or 790) with the plurality of particles (e.g., 712, 772, and/or 792) having an arrangement with a first average spacing between particles (e.g., as depicted in FIGS. 7F, 7G, and/or 7H) (e.g., a spaced apart positioning of the particles, a spacing of the particles that does not form a distinct shape, a uniform spacing of the particles, an irregularly spaced positioning of the particles, and/or a non-uniform manner of particle spacing), the computer system detects termination of the user experience session (e.g., a transition to an ending portion (e.g., outro) of the user experience session or an immediate termination). In response to detecting termination of the user experience session, the computer system displays an animation of the plurality of particles moving to an arrangement with a second average spacing between particles, where the second average spacing is smaller than the first average spacing (e.g., as depicted in FIG. 7I) (e.g., a dense, compact, and/or tight grouping of the particles, forming a shape (e.g., orb, cloud, triangle, pyramid, and/or cube), a uniform spacing of the particles, an irregularly spaced positioning of the particles, and/or a non-uniform manner of particle spacing) (e.g., and terminating (e.g., initiating termination of) the user experience session). Displaying the animation of the plurality of particles moving to the grouped arrangement in response to detecting termination of the user experience session provides feedback about a state of the computer system (e.g., a state in which the computer system is terminating the user experience session). In some embodiments, in response to detecting termination of the user experience session, the computer system terminates (or initiates termination of) the user experience session while (or after) the plurality of particles are animated moving to the arrangement with the second average spacing between particles. In some embodiments, terminating the user experience session includes transitioning to an outro portion of the user experience session.

In some embodiments, displaying the user interface for the user experience session includes: while the user experience session is active and an environment (e.g., 700a) (e.g., representations of elements in the physical environment or virtual elements in an XR environment) of the user (e.g., 701) of the computer system (e.g., 702) is visually obscured (e.g., via dimming effect 704) (e.g., dimmed (e.g., 1% visible or 2% visible) or not displayed), the computer system detects termination of the user experience session (e.g., a transition to an ending portion (e.g., outro) of the user experience session). In response to detecting termination of the user experience session, the computer system initiates termination of the user experience session (e.g., a transitioning to an ending portion (e.g., outro) of the user experience session and/or ending the user experience session) and gradually increases visibility of the environment of the user (e.g., fading the environment into view) (e.g., as depicted in FIG. 7I). Initiating termination of the user experience session and gradually increasing visibility of the environment of the user in response to detecting termination of the user experience session provides feedback about a state of the computer system (e.g., a state in which the computer system is terminating the user experience session). In some embodiments, increasing visibility of the environment includes reducing a dimming effect that was displayed (e.g., overlaid) onto the environment (e.g., a physical environment). In some embodiments, increasing visibility of the environment includes displaying a greater portion of the environment (e.g., a virtual or XR environment). In some embodiments, the visibility of the environment is increased (e.g., 10% visible) at a first time, is further increased (e.g., 25% visible) at a second time after the first time, is further increased (e.g., 50% visible) at a third time after the second time, and is further increased (e.g., 98% visible) at a fourth time after the third time.

In some embodiments, displaying the user interface for the user experience session includes: while the user experience session is active, the computer system (e.g., 702) detects termination of the user experience session (e.g., a transition to an ending portion (e.g., outro) of the user experience session). In response to detecting termination of the user experience session, the computer system initiates termination of the user experience session (e.g., a transitioning to an ending portion (e.g., outro) of the user experience session and/or ending the user experience session) and displays an option (e.g., 758) that is selectable to continue the user experience session (e.g., resume the user experience session after termination of the session; resume the user experience session before termination of the session). Initiating termination of the user experience session and displaying the option that is selectable to continue the user experience session reduces the number of inputs needed to continue the user experience session by automatically displaying an option to continue the user experience session without additional user input. In some embodiments, in response to detecting selection of the option that is selectable to continue the user experience session, the computer system resumes the user experience session and ceases display of the option that is selectable to continue the user experience session.

In some embodiments, displaying the user interface for the user experience session includes: while the user experience session is active, the computer system (e.g., 702) detects termination of the user experience session (e.g., a transition to an ending portion (e.g., outro) of the user experience session). In response to detecting termination of the user experience session, the computer system initiates termination of the user experience session (e.g., a transitioning to an ending portion (e.g., outro) of the user experience session and/or ending the user experience session) and displays a history of data related to (e.g., based on or corresponding to) one or more previous user experience sessions (e.g., 754 and/or 756) (in some embodiments, the one or more previous user experience sessions includes the current user experience session). Initiating termination of the user experience session and displaying the history of data related to one or more previous user experience sessions reduces the number of inputs needed to view history data by automatically displaying the history data without additional user input.

In some embodiments, displaying the user interface for the user experience session includes causing at least a portion of an environment (e.g., 700a) (e.g., representations of elements in the physical environment and/or virtual elements in the XR environment) of the user (e.g., 701) of the computer system (e.g., 702) to be visible (e.g., displayed via pass-through video and/or visible due to a transparent nature of the display) while the user experience session is active (e.g., as depicted in FIGS. 7D, 7E, 7F, 7G, and/or 7H). Causing at least a portion of the environment of the user of the computer system to be visible while the user experience session is active provides feedback about a state of the computer system. In some embodiments, the user interface for the user experience session is displayed with an amount of opacity or transparency such that the environment of the user is visible through (or behind) the user interface. In some embodiments, the user interface is displayed with an opacity of 99.9%, 99%, 98%, 97%, 95%, 90%, 85%, 80%, and/or another amount less than 100%.

In some embodiments, while the user experience session is active and while the computer system (e.g., 702) displays the user interface object (e.g., 710, 770, and/or 790) having a first displayed orientation relative to the user (e.g., 701) of the computer system (e.g., the user interface object is displayed at a first angle with respect to the user), the computer system receives data indicating a change in position of the user of the computer system from a first position in an environment (e.g., 700) (e.g., as depicted in FIG. 7G) to a second position in the environment different from the first position (e.g., a change in position of the user relative to the user's physical environment and/or the XR environment) (e.g., as depicted in FIG. 7H). In response to receiving the data indicating a change in position of the user of the computer system, the computer system displays the user interface object having a second displayed orientation relative to the user of the computer system different from the first displayed orientation (e.g., the user interface object is displayed at a second angle with respect to the user) (e.g., as depicted in FIG. 7H). Displaying the user interface object having the second displayed orientation relative to the user of the computer system different from the first displayed orientation in response to receiving the data indicating the change in position of the user of the computer system causes the computer system to automatically adjust the displayed view of the user experience session based on a detected change in position of the user of the computer system.

In some embodiments, displaying the user interface object having the second displayed orientation includes displaying at least a portion of the user interface object that was not visible (e.g., displayed) when the user interface object was displayed having the first orientation. In some embodiments, displaying the user interface object having the second displayed orientation includes hiding (e.g., ceasing to display) at least a portion of the user interface object that was visible (e.g., displayed) when the user interface object was displayed having the first orientation.

In some embodiments, the user interface for the user experience session is capable of being displayed at one or more external computer systems (e.g., devices or computer systems associated with other users (e.g., users in an XR environment)).

In some embodiments, while the user experience session is active and while the computer system (e.g., 702) is displaying the user interface object having the plurality of particles (e.g., 712, 772, and/or 792) that move based on the one or more breathing characteristics of the user of the computer system, the computer system receives data indicating a change in pose of a portion of the user (e.g., 701) of the computer system (e.g., the user's hand and/or arm is moving in the XR environment). In response to receiving the data indicating the change in pose of the portion of the user of the computer system, the computer system updates display of the plurality of particles, including: in accordance with a determination that the data indicating the change in pose of the portion of the user includes an indication that the portion of the user intersects (or intersected during movement) a displayed location of a respective particle, modifying a displayed characteristic of the respective particle (e.g., changing a color, position, and/or orientation of the respective particle, and/or displaying an animated effect based on the intersection of the user's hand with the respective particle); and in accordance with a determination that the data indicating the change in pose of the portion of the user does not include an indication that the portion of the user intersects (or intersected during movement) the displayed location of the respective particle, forgoing modifying the displayed characteristic of the respective particle (e.g., maintaining the displayed color, position, and/or orientation of the respective particle and/or forgoing displaying an animated effect based on an intersection of the user's hand with the respective particle). Modifying the displayed characteristic of the respective particle in accordance with the determination that the data indicating the change in pose of the portion of the user includes an indication that the portion of the user intersects the displayed location of the respective particle causes the computer system to automatically adjust the displayed respective particle based on a detected position of the portion of the user intersecting the respective particle. In some embodiments, some of the particles move and/or change color based on movement of the portion of the user (e.g., the user can interact with the particles).

In some embodiments, aspects/operations of methods 900 and/or 1000 may be interchanged, substituted, and/or added between these methods. For brevity, these details are not repeated here.

FIG. 9 is a flow diagram of an exemplary method 900 for providing a computer-generated user experience session with options selected based on characteristics of an XR environment, in accordance with some embodiments. In some embodiments, method 900 is performed at a computer system (e.g., computer system 101 in FIG. 1 and/or device 702) (e.g., a smartphone, tablet, and/or head-mounted display generation component) that is in communication with a display generation component (e.g., display generation component 120 in FIGS. 1, 3, and 4 and/or display 702-1) (e.g., a display, a touchscreen, a visual output device, a 3D display, a display having at least a portion that is transparent or translucent on which images can be projected (e.g., a see-through display), a projector, a heads-up display, and/or a display controller) and one or more sensors (e.g., camera 702-2) (e.g., a gyroscope, an accelerometer, a motion sensor, a movement sensor, a microphone, an infrared sensor, a camera sensor, a depth camera, a visible light camera, an eye-tracking sensor, a gaze-tracking sensor, a physiological sensor, an image sensor, a camera (e.g., color sensors, infrared sensors, and other depth-sensing cameras) that points downward at a user's hand, and/or a camera that points forward from the user's head). In some embodiments, the method 900 is governed by instructions that are stored in a non-transitory (or transitory) computer-readable storage medium and that are executed by one or more processors of a computer system, such as the one or more processors 202 of computer system 101 (e.g., control 110 in FIG. 1A). Some operations in method 900 are, optionally, combined and/or the order of some operations is, optionally, changed.

In method 900, while displaying an XR environment (e.g., 705, 765, and/or 787) having one or more characteristics (e.g., lighting characteristics, display of virtual objects, passthrough display of physical objects, and/or a user history of activity in the XR environment), the computer system (e.g., 702) detects (902), via the one or more sensors (e.g., 702-1 and/or 702-2), a request (e.g., via input 724 and/or input 778) to initiate a user experience session in the XR environment (e.g., a request to start a user experience in the XR environment that optionally includes guided instruction for breathing exercises to relax and/or focus the user and/or reflection exercises to help the user reflect on a scenario, topic, idea, concept, etc.).

In response to detecting the request to initiate the user experience session in the XR environment, the computer system (e.g., 702) initiates (904) the user experience session in the XR environment (e.g., starting the user experience in the XR environment that optionally includes guided instruction for breathing exercises to relax and/or focus the user and/or reflection exercises to help the user reflect on a scenario, topic, idea, concept, etc.). In some embodiments, starting the user experience in the XR environment includes launching an application for providing the user experience.

As a part of initiating the user experience session in the XR environment, the computer system (e.g., 702) displays (906) (e.g., in the XR environment), via the display generation component (e.g., 702-1), a user interface (e.g., 705, 765, and/or 787) for the user experience session (e.g., a UI of an application for the breathing exercises and/or reflection exercises). Displaying the user interface for the user experience session includes: in accordance with a determination that the one or more characteristics of the XR environment satisfy a first set of criteria (e.g., the XR environment is an AR environment; the XR environment includes a first environment; the XR environment has a first set of lighting conditions; one or more user experience sessions have previously been initiated in the XR environment), the computer system displays (908) the user interface for the user experience session with a first set of one or more options enabled for the user experience session (e.g., a first set of visual and/or audio characteristics for the session, displaying a first virtual environment, and/or displaying one or more virtual objects having a first appearance).

In accordance with a determination that the one or more characteristics of the XR environment satisfy a second set of criteria different from the first set of criteria (e.g., the XR environment is a VR environment; the XR environment includes a second environment; the XR environment has a second set of lighting conditions; no user experience sessions have previously been initiated in the XR environment), the computer system (e.g., 702) displays (910) the user interface for the user experience session with a second set of one or more options enabled for the user experience session (e.g., a second set of visual and/or audio characteristics for the session, displaying a second virtual environment, and/or displaying one or more virtual objects having a second appearance), wherein the second set of one or more options are different from the first set of one or more options. Displaying the user interface for the user experience session with the first set of one or more options enabled for the user experience session in accordance with a determination that the one or more characteristics of the XR environment satisfy the first set of criteria, and displaying the user interface for the user experience session with the second set of one or more options enabled for the user experience session in accordance with a determination that the one or more characteristics of the XR environment satisfy the second set of criteria, reduces the number of inputs needed to display the user interface for the user experience session with particular options enabled for the user experience session.

In some embodiments, displaying the user interface for the user experience session with the first set of one or more options enabled for the user experience session (e.g., a first set of visual and/or audio characteristics for the session) includes the computer system (e.g., 702) displaying an augmented reality (AR) environment (e.g., 705) for the user experience session (e.g., as depicted in FIGS. 7B, 7C, 7D, 7E, 7F, 7G, 7H, and/or 7I). In some embodiments, displaying the user interface for the user experience session with the second set of one or more options enabled for the user experience session (e.g., a second set of visual and/or audio characteristics for the session) includes the computer system displaying a virtual reality (VR) environment (e.g., 765 and/or 787) for the user experience session (e.g., as depicted in FIGS. 7J, 7K, and/or 7L). Displaying an AR environment or VR environment for the user experience session when the one or more characteristics of the XR environment satisfy the first or second sets of criteria causes the device to automatically enable an AR environment or VR environment based on the characteristics of the XR environment without displaying additional controls.

In some embodiments, the first set of one or more options includes a first subset of options (e.g., visual and/or audio characteristics for the user experience session) for the AR environment (e.g., as depicted in FIGS. 7B, 7C, 7D, 7E, 7F, 7G, 7H, and/or 7I) that are selected (e.g., randomly or pseudorandomly) from a first set of available options (e.g., a superset of options for the AR environment). In some embodiments, the second set of one or more options includes a second subset of options (e.g., visual and/or audio characteristics for the user experience session) for the VR environment (e.g., as depicted in FIGS. 7J, 7K, and/or 7L) that are selected (e.g., randomly or pseudorandomly) from a second set of available options (e.g., a superset of options for the VR environment). In some embodiments, the first set of available options includes a different quantity of (e.g., fewer or more) options than the second set of available options. Selecting the first subset of options for the AR environment from the first set of available options and selecting the second subset of options for the VR environment from the second set of available options, wherein the first set of available options includes a different quantity of options that the second set of available options, enables the computer system to provide a more realistic user experience while saving storage space by not requiring multiple different complete audio tracks and/or visual components to be stored and selected for playback/display. In some embodiments, the options available for a VR environment are more limited than the options available for an AR environment. In some embodiments, the options available for the VR environment can be used to create a smaller set of recipes for creating the VR environment or include a smaller range of variables than is otherwise available for creating the AR environment.

In some embodiments, displaying the user interface for the user experience session with the first set of one or more options enabled for the user experience session (e.g., a first set of visual and/or audio characteristics for the session) includes the computer system (e.g., 702) displaying a first environment (e.g., 765) (e.g., a first virtual environment) for the user experience session. In some embodiments, displaying the user interface for the user experience session with the second set of one or more options enabled for the user experience session (e.g., a second set of visual and/or audio characteristics for the session) includes displaying a second environment different from the first environment (e.g., 787) (e.g., a second virtual environment) for the user experience session. Displaying the first environment or second environment for the user experience session when the one or more characteristics of the XR environment satisfy the first or second sets of criteria causes the device to automatically display the first environment or second environment based on the characteristics of the XR environment without displaying additional controls.

In some embodiments, the virtual environments are backdrops or wallpapers for a three-dimensional environment. In some embodiments, the virtual environments can be displayed outside of (e.g., before and/or after) the user experience session. In some embodiments, the virtual environments provide a virtual, three-dimensional space in which a user performs activities using the computer system such as using applications, playing games, communicating with other users, experiencing copresence with other users, and/or interacting with elements of an operating system of the computer system. In some embodiments, the computer system provides respective spatial audio soundscapes for the various virtual environments. In some embodiments, the spatial audio soundscapes are unique to each respective virtual environment. In some embodiments, the spatial audio soundscapes are curated for respective virtual environments, for example, in order to convey a particular mood and/or theme for the respective virtual environment.

In some embodiments, the first set of one or more options includes a first set of variables (e.g., 770, 772, 774, and/or 780-1) (e.g., visual and/or audio characteristics for the user experience session) for the first environment that are based on one or more characteristics of the first environment (e.g., 765) (e.g., the variables for the first environment are tailored or optimized for the first environment). In some embodiments, the second set of one or more options includes a second set of variables (e.g., 790, 792, 794, and/or 785-1) (e.g., visual and/or audio characteristics for the user experience session) (e.g., different from the first set of variables) for the second environment (e.g., 787) that are based on one or more characteristics of the second environment (e.g., the variables for the second environment are tailored or optimized for the second environment).

In some embodiments, the first set of criteria includes a first criterion that is met when a prior user interface (e.g., 765) for a prior user experience session (e.g., a prior instance of the user experience session) has been displayed having a prior set of visual characteristics (e.g., 770 and/or 772) (e.g., visual properties, colors, shapes, sizes, graphics, and/or animated effects for displayed components of the prior user experience session) for the prior user experience session. In some embodiments, displaying the user interface for the user experience session with the first set of one or more options enabled for the user experience session (e.g., the current instance of the user experience session) includes the computer system (e.g., 702) displaying the user interface (e.g., 787) having a first set of visual characteristics (e.g., 790 and/or 792) (e.g., visual properties, colors, shapes, sizes, graphics, and/or animated effects for displayed components of the user experience session) for the user experience session different from the prior set of visual characteristics for the prior user experience session. Displaying the user interface having the first set of visual characteristics for the user experience session different from the prior set of visual characteristics for the prior user experience session enables the computer system to generate unique or fresh user interfaces for the user experience session based on a history of user experience sessions without displaying additional controls. In some embodiments, subsequent instances of the user experience session (e.g., repeated user experience sessions) have different visual characteristics that are selected to be unique or different from prior instances of the user experience session. In some embodiments, the second set of criteria includes the first criterion. In some embodiments, the second set of criteria includes a second criterion that is met when a second prior user interface for a second prior user experience session has been displayed having a second prior set of visual characteristics for the second prior user experience session. In some embodiments, displaying the user interface for the user experience session with the second set of one or more options enabled for the user experience session includes displaying the user interface having a second set of visual characteristics for the user experience session different from the second prior set of visual characteristics for the second prior user experience session (and, optionally, different from the prior set of visual characteristics for the prior user experience session).

In some embodiments, the first set of visual characteristics for the user experience session are selected randomly or pseudorandomly by the computer system (e.g., 702) from a set of available visual characteristics (e.g., a superset of visual characteristics). Selecting the first set of visual characteristics for the user experience session randomly or pseudorandomly from the set of available visual characteristics enables the computer system to provide a more realistic user experience while saving storage space by not requiring multiple different complete visual components to be stored and selected for display. In some embodiments, the set of visual characteristics for the user experience session are selected with a bias towards not repeating one or more of the visual characteristics that have been used in prior user experience sessions. For example, the set of available visual characteristics includes the prior set of visual characteristics and the first set of visual characteristics are selected from a subset of the available visual characteristics that does not include the prior set of visual characteristics.

In some embodiments, the prior set of visual characteristics include first light properties (e.g., direction, color, and/or intensity of light) for a simulated lighting effect (e.g., a simulated reflection of light) for a user interface object (e.g., 710, 712, 770, 772, 790, and/or 792) (e.g., one or more particles forming a cube, sphere, orb, cloud, pyramid, and/or abstract object) displayed in the prior user experience session. In some embodiments, the first set of visual characteristics include second light properties, different from the first light properties, for a simulated lighting effect for a user interface object displayed in the user experience session (e.g., the user interface for the user experience session includes a user interface object that includes a plurality of particles that have a set of light properties for simulated lights reflecting off the particles). Displaying the user interface with the first set of visual characteristics including the second light properties, different form the first light properties, for the simulated lighting effect for the user interface object displayed in the user experience session enables the computer system to provide a more realistic user experience while saving storage space by not requiring multiple different complete visual components to be stored and selected for display.

In some embodiments, the prior set of visual characteristics include first material properties (e.g., simulated optical properties, shape, and/or bend) for a user interface object (e.g., 710, 712, 770, 772, 790, and/or 792) (e.g., one or more particles forming a cube, sphere, orb, cloud, pyramid, and/or abstract object) displayed in the prior user experience session. In some embodiments, the first set of visual characteristics include second material properties, different from the first material properties, for a user interface object displayed in the user experience session (e.g., the user interface for the user experience session includes a user interface object that includes a plurality of particles that have a set of material properties). Displaying the user interface with the first set of visual characteristics including the second material properties, different form the first material properties, for the user interface object displayed in the user experience session enables the computer system to provide a more realistic user experience while saving storage space by not requiring multiple different complete visual components to be stored and selected for display.

In some embodiments, displaying the user interface for the user experience session with the first set of one or more options enabled for the user experience session (e.g., a first set of visual and/or audio characteristics for the session) includes the computer system (e.g., 702) displaying a VR environment (e.g., 765 and/or 787) for the user experience session having a first amount of emphasis (e.g., a low amount of dimming, no dimming; no dimming effect; no fading of the VR environment). In some embodiments, displaying the user interface for the user experience session with the second set of one or more options enabled for the user experience session (e.g., a second set of visual and/or audio characteristics for the session) includes displaying an AR environment (e.g., 705) for the user experience session having a second amount of emphasis (e.g., 704) less than the first amount of emphasis (e.g., the AR environment is displayed having a greater fading effect or dimming effect) (e.g., the AR environment is dimmed by 99.9%, 99%, 98%, 97%, 95%, 90%, 85%, 80%, 50%, 20%, 15%, 10%, 7%, 5%, 3%, 2%, 1%, 0.5%, and/or another amount greater than 0%). Displaying the AR environment for the user experience session having a second amount of emphasis less than the first amount of emphasis for the VR environment reduces distractions for the user experience session.

In some embodiments, an AR environment is displayed having a greater amount of dimming than a VR environment. In some embodiments, displaying the dimming effect includes visually obscuring a view of the physical environment that is visible (e.g., 700a) (e.g., via pass-through video or due to a transparent nature of the display) to a user (e.g., 701) of the computer system (e.g., 702). In some embodiments, displaying the dimming effect (e.g., 704) includes displaying a virtual overlay that is partially transparent to show the physical environment through the virtual overlay. In some embodiments, the AR environment is dimmed in order to reduce distractions in a manner different from that in a VR environment. For example, the computer system can harmonize the user experience session in a VR environment by displaying a particular virtual environment, thereby reducing potential distractions to the user, whereas the distractions in an AR environment are reduced by the computer system dimming the visibility of objects in the physical environment.

In some embodiments, displaying the user interface for the user experience session includes displaying a plurality of user interface objects (e.g., 710, 712, 770, 772, 790, and/or 792) (e.g., one or more particles forming a cube, sphere, orb, cloud, pyramid, and/or abstract object) having a translucent appearance based on an environment (e.g., 700a, 705, 765, and/or 787) (e.g., physical objects, virtual objects, detected lighting, and/or virtual lighting in the XR environment) for the user experience session (e.g., the translucent appearance of the particles is impacted by elements of the environment for the user experience session). Displaying the plurality of user interface objects having the translucent appearance based on the environment for the user experience session enables the computer system to provide a more realistic user experience based on the environment for the user experience session while saving storage space by not requiring multiple different complete visual components to be stored and selected for display.

In some embodiments, displaying the plurality of user interface objects (e.g., 710, 712, 770, 772, 790, and/or 792) having the translucent appearance based on the environment of the user experience session includes: in accordance with a determination that the environment for the user experience session includes a first virtual lighting effect (e.g., a simulated position, direction, color, and/or intensity of light in the XR environment), the computer system (e.g., 702) displays the plurality of user interface objects having a first translucent appearance (e.g., the translucence of the particles has a first position on the respective particles and/or a first amount of translucence) (e.g., in FIGS. 7J and/or 7K). In some embodiments, in accordance with a determination that the environment for the user experience session includes a second virtual lighting effect (e.g., a simulated position, direction, color, and/or intensity of light in the XR environment) different from the first virtual lighting effect, displaying the plurality of user interface objects having a second translucent appearance different from the first translucent appearance (e.g., the translucence of the particles has a second position on the respective particles and/or a second amount of translucence) (e.g., in FIG. 7L). Displaying the plurality of user interface objects having the second translucent appearance in accordance with a determination that the environment includes the second virtual lighting effect enables the computer system to provide a more realistic user experience based on a virtual lighting effect in the environment for the user experience session while saving storage space by not requiring multiple different complete visual components to be stored and selected for display. In some embodiments, the visual appearance of user interface objects having a translucent appearance are impacted by virtual lighting of the AR/VR environment.

In some embodiments, initiating the user experience session in the XR environment includes the computer system (e.g., 702) increasing one or more immersive aspects of the user experience session (e.g., increasing a proportion of the user's field-of-view that is occupied by the environment, and/or increasing spatial immersion of audio for the environment) (e.g., as depicted in FIGS. 7D and/or 7K). Increasing one or more immersive aspects of the user experience session provides feedback about a state of the computer system and eliminates distractions for the user experience session.

In some embodiments, increasing one or more immersive aspects of the user experience session includes the computer system (e.g., 702) increasing a proportion of a user field-of-view (e.g., the field-of-view of the display generation component (e.g., 702-1)) occupied by the user interface for the user experience session (e.g., increasing the displayed size of virtual wallpaper 765, virtual object 770, and/or particles 772 in FIG. 7K) (e.g., increasing the displayed size of virtual interface 705, virtual object 710, and/or particles 712 in FIG. 7D). Increasing the proportion of the user field-of-view occupied by the user interface for the user experience session provides feedback about a state of the computer system and eliminates distractions for the user experience session.

In some embodiments, increasing one or more immersive aspects of the user experience session includes the computer system (e.g., 702) increasing a spatial immersion of audio generated for the user experience session (e.g., causing a perceived spatial location of audio to move from a first location perceived to be a distance away from a user of the computer system to a second location perceived (by the user) to be near and/or surrounding the user) (e.g., transitioning from stereo audio to spatial audio in FIGS. 7D and/or 7K). Increasing the spatial immersion of audio generated for the user experience session provides feedback about a state of the computer system and eliminates distractions for the user experience session.

In some embodiments, aspects/operations of methods 800 and/or 1000 may be interchanged, substituted, and/or added between these methods. For brevity, these details are not repeated here.

FIGS. 10A-10B are a flow diagram of an exemplary method 900 for providing a computer-generated user experience session with a soundscape having randomly selected curated sound components, in accordance with some embodiments. In some embodiments, method 1000 is performed at a computer system (e.g., computer system 101 in FIG. 1 and/or device 702) (e.g., a smartphone, tablet, and/or head-mounted display generation component) that is in communication with a display generation component (e.g., display generation component 120 in FIGS. 1, 3, and 4 and/or display 702-1) (e.g., a display, a touchscreen, a visual output device, a 3D display, a display having at least a portion that is transparent or translucent on which images can be projected (e.g., a see-through display), a projector, a heads-up display, and/or a display controller), an audio generation component (e.g., audio output device 703 and/or a speaker at device 702, or an audio generation component integrated into an HMD) (e.g., a speaker and/or a bone conduction audio output device), and one or more sensors (e.g., camera 702-2) (e.g., a gyroscope, an accelerometer, a motion sensor, a movement sensor, a microphone, an infrared sensor, a camera sensor, a depth camera, a visible light camera, an eye-tracking sensor, a gaze-tracking sensor, a physiological sensor, an image sensor, a camera (e.g., color sensors, infrared sensors, and other depth-sensing cameras) that points downward at a user's hand, and/or a camera that points forward from the user's head). In some embodiments, the method 1000 is governed by instructions that are stored in a non-transitory (or transitory) computer-readable storage medium and that are executed by one or more processors of a computer system, such as the one or more processors 202 of computer system 101 (e.g., control 110 in FIG. 1A). Some operations in method 1000 are, optionally, combined and/or the order of some operations is, optionally, changed.

In method 1000, computer system (702) detects (1002), at a first time (e.g., depicted in FIG. 7B or depicted in FIG. 7J), via the one or more sensors (e.g., 702-1 and/or 702-2), a request (e.g., input 724, input 778, or a similar input) to initiate a user experience session of a respective type in an XR environment (e.g., a request to start a user experience in the XR environment that optionally includes guided instruction for breathing exercises to relax and/or focus the user and/or reflection exercises to help the user reflect on a scenario, topic, idea, concept, etc.).

In response to detecting the request to initiate the user experience session in the XR environment, the computer system (e.g., 702) initiates (1004) a first user experience session of the respective type in the XR environment (e.g., depicted in FIG. 7D or depicted in FIG. 7K) (e.g., starting the user experience in the XR environment that optionally includes guided instruction for breathing exercises to relax and/or focus the user and/or reflection exercises to help the user reflect on a scenario, topic, idea, concept, etc.). In some embodiments, starting the user experience in the XR environment includes launching an application for providing the user experience.

As a part of initiating the first user experience session of the respective type in the XR environment, the computer system (e.g., 702) displays (1006) (e.g., in the XR environment), via the display generation component (e.g., 702-1), a user interface (e.g., 705, 710, 712, 765, 770, and/or 772) for the first user experience session (e.g., a UI of an application for the breathing exercises and/or reflection exercises). The computer system also outputs (1008), via the audio generation component (e.g., 703), a first audio soundscape (e.g., 711 or 774) (e.g., a set of curated sound components selected to create an audio environment for the user experience session) for the first user experience session (e.g., while displaying the user interface for the first user experience session). The computer system outputs the first audio soundscape concurrently with displaying the user interface for the first user experience session. Outputting the first audio soundscape includes outputting the first audio soundscape with a first set of two or more audio components selected randomly or pseudorandomly from a set of available audio components. In some embodiments, the two or more audio components in the first set of audio components is a subset of curated sound components that are selected from a superset of curated sound components for the audio soundscape.

In method 1000, the computer system (e.g., 702) detects (1010), at a second time that is different from the first time (e.g., depicted in FIG. 7B or depicted in FIG. 7J), via the one or more sensors (e.g., 702-1 and/or 702-2), a request (e.g., input 724, input 778, or a similar input) to initiate a user experience session of the respective type in an XR environment (e.g., a request to start a user experience in the XR environment that optionally includes guided instruction for breathing exercises to relax and/or focus the user and/or reflection exercises to help the user reflect on a scenario, topic, idea, concept, etc.).

In response to detecting the request to initiate the user experience session in the XR environment, the computer system (e.g., 702) initiates (1012) a second user experience session of the respective type in the XR environment (e.g., depicted in FIG. 7L) (e.g., starting the user experience in the XR environment that optionally includes guided instruction for breathing exercises to relax and/or focus the user and/or reflection exercises to help the user reflect on a scenario, topic, idea, concept, etc.). In some embodiments, starting the user experience in the XR environment includes launching an application for providing the user experience.

As a part of initiating the second user experience session of the respective type in the XR environment, the computer system (e.g., 702) displays (1014) (e.g., in the XR environment), via the display generation component (e.g., 702-1), a user interface (e.g., 787, 790, and/or 792) for the second user experience session (e.g., a UI of an application for the breathing exercises and/or reflection exercises). The computer system also outputs (1016), via the audio generation component (e.g., 703), a second audio soundscape (e.g., 794) (e.g., a set of curated sound components selected to create an audio environment for the user experience session) for the second user experience session (e.g., while displaying the user interface for the second user experience session). The computer system outputs the second audio soundscape concurrently with displaying the user interface for the second user experience session. Outputting the second audio soundscape includes outputting the second audio soundscape with a second set of two or more audio components (e.g., different from the first set of two or more audio components) selected randomly or pseudorandomly from the set of available audio components. Outputting a second audio soundscape for the second user experience session, wherein the second audio soundscape is output concurrently with displaying the user interface for the second user experience session and outputting the second audio soundscape includes outputting the second audio soundscape with a second set of two or more audio components selected randomly or pseudorandomly from the set of available audio components enables the computer system to provide a more realistic user experience while saving storage space by not requiring multiple different complete audio tracks to be stored and selected for playback. In some embodiments, the two or more audio components in the second set of audio components is a subset of curated sound components that is selected from a superset of curated sound components for the audio soundscape. In some embodiments, at least one of the two or more audio components in the second set of audio components is selected to be different from the audio components in the first set of audio components.

In some embodiments, outputting the first audio soundscape (e.g., 711 or 774) for the first user experience session includes the computer system (e.g., 702) repeating (e.g., continuously repeating on a loop) the first set of two or more audio components during the first user experience session. In some embodiments, outputting the second audio soundscape for the second user experience session includes repeating (e.g., continuously repeating on a loop) the second set of two or more audio components during the second user experience session. Repeating the first set of two or more audio components during the first user experience session provides feedback about a state of the computer system (e.g., a state of outputting the first user experience session).

In some embodiments, the first set of two or more audio components for the first audio soundscape (e.g., 711 or 774) is different from the second set of two or more audio components for the second audio soundscape (e.g., 794). Outputting the first and/or second soundscape, wherein the first set of two or more audio components is different from the second set of two or more audio components, enables the computer system to provide a more realistic user experience while saving storage space by not requiring multiple different complete audio tracks to be stored and selected for playback.

In some embodiments, outputting the first audio soundscape (e.g., 711 or 774) for the first user experience session concurrently with displaying the user interface (e.g., 705, 710, 712, 765, 770, and/or 772) for the first user experience session includes the following. When the user interface for the first user experience session includes a first predetermined animated effect (e.g., an animated effect of a visual component displayed for a particular phase or portion of the first user experience session) (e.g., a pulsating animation (e.g., a repeating, alternating pattern of increasing the size of the visual component and decreasing the size of the visual component) of a visual component (e.g., orb, ball, cube, swirl, and/or cloud) for a guided breathing portion of the first user experience) the computer system (e.g., 702) outputs the first set of two or more audio components with a first set of audio characteristics (e.g., the first set of two or more audio components have a set of audio characteristics that is determined based on the predetermined animated effect) (e.g., increasing the volume of the two or more audio components in the first set when the size of the visual component increases, and decreasing the volume of the two or more audio components in the first set when the size of the visual component decreases). When the user interface for the first user experience session includes a second predetermined animated effect different from the first predetermined animated effect (e.g., a floating/swaying animated appearance of a visual component (e.g., particles, triangles, circles, squares, and/or small cubes) for a reflection portion of the first user experience), the computer system outputs the first set of two or more audio components with a second set of audio characteristics different from the first set of audio characteristics (e.g., the audio is output with changes in spatial location based on the floating/swaying movement of the visual component). Outputting the first set of two or more audio components with a first set of audio characteristics when the user interface for the first user experience session includes a first predetermined animated effect, and outputting the first set of two or more audio components with a second set of audio characteristics different from the first set of audio characteristics when the first user experience session includes a second predetermined animated effect different from the first predetermined animated effect causes the computer system to automatically modify the first audio soundscape based on an animated effect being output in the user interface for the first user experience session.

In some embodiments, outputting the second audio soundscape (e.g., 794) for the second user experience session concurrently with displaying the user interface for the second user experience session (e.g., 787, 790, and/or 792) includes the following. When the user interface for the second user experience session includes a third predetermined animated effect (in some embodiments, the third predetermined animated effect is the same as the first predetermined animated effect), the computer system (e.g., 702) outputs the second set of two or more audio components with a third set of audio characteristics (in some embodiments, the third set of audio characteristics is the same as the first set of audio characteristics). When the user interface for the second user experience session includes a fourth predetermined animated effect different from the third predetermined animated effect (in some embodiments, the fourth predetermined animated effect is the same as the second predetermined animated effect), the computer system outputs the second set of two or more audio components with a fourth set of audio characteristics different from the third set of audio characteristics (in some embodiments, the fourth set of audio characteristics is the same as the second set of audio characteristics).

In some embodiments, both the visual effect (e.g., the predetermined animated effect) and the audio components (e.g., 711, 774, and/or 794) (e.g., the corresponding audio soundscape) are selected based on some criteria (e.g., the same criteria). For example, when a particular soundscape is selected (e.g., by the user and/or by the computer system), a corresponding visual effect is automatically selected (e.g., by the computer system) to accompany the selected soundscape, or when a particular visual effect is selected, a corresponding soundscape is automatically selected (e.g., by the computer system) to accompany the selected visual effect. As another example, a particular virtual environment, theme, and/or mood is selected and a particular soundscape and/or visual effect is automatically selected (e.g., by the computer system) for the selected environment, theme, and/or mood.

In some embodiments, while outputting the first audio soundscape (e.g., 711 or 774) for the first user experience session, the computer system (e.g., 702) detects (e.g., determines) (e.g., using a sensor) a biometric input (e.g., an inward breath, an outward breath, a heartbeat, and/or a body movement). In some embodiments, in response to detecting the biometric input, the computer system modifies the first audio soundscape, including: in accordance with a determination that the biometric input includes a first biometric input (e.g., an inward breath), the computer system modifies the first set of two or more audio components in a first manner (e.g., outputting the first soundscape to have a perceived spatial location of the audio components that is moving towards the user) (e.g., as depicted by the locations of spatial audio indicators 709-3 to 709-9 in FIG. 7G). In accordance with a determination that the biometric input includes a second biometric input different from the first biometric input (e.g., an outward breath), the computer system modifies the first set of two or more audio components in a second manner different from the first manner (e.g., outputting the first soundscape to have a perceived spatial location of the audio components that is moving away from the user) (e.g., as depicted by the locations of spatial audio indicators 709-3 to 709-9 in FIG. 7F). Modifying the first set of two or more audio components in a first manner when the biometric input includes a first biometric input, and modifying the first set of two or more audio components in a second manner different from the first manner when the biometric input includes a second biometric input different from the first biometric input, causes the computer system to automatically modify the first audio soundscape based on an a biometric input detected during the first user experience session.

In some embodiments, while outputting the second audio soundscape (e.g., 774 or 794) for the second user experience session, the computer system (e.g., 702) detects a biometric input. In response to detecting the biometric input, the computer system modifies the second audio soundscape, including: in accordance with a determination that the biometric input includes a third biometric input (e.g., the first biometric input) (e.g., an inward breath), modifying the second set of two or more audio components in a third manner (e.g., in the first manner) (e.g., outputting the second soundscape to have a perceived spatial location of the audio components that is moving towards the user); and in accordance with a determination that the biometric input includes a fourth biometric input different from the third biometric input (e.g., the second biometric input) (e.g., an outward breath), modifying the second set of two or more audio components in a fourth manner different from the third manner (e.g., in the second manner) (e.g., outputting the second soundscape to have a perceived spatial location of the audio components that is moving away from the user). In some embodiments, characteristics of the audio (e.g., spatial location of audio and/or spatial movement of the audio) is based on user biometric measurements (e.g., breaths, movement, and/or heartrate)

In some embodiments, outputting the first audio soundscape (e.g., 711 or 774) for the first user experience session includes: in accordance with a determination that a first set of criteria is met (e.g., a predetermined amount of time has elapsed and/or the first user experience is transitioning (or has transitioned) from a first portion of the user experience to a second portion of the user experience), the computer system (e.g., 702) causes a gradual increase in an output volume of the first audio soundscape (e.g., as depicted in FIGS. 7D and/or 7K); and in accordance with a determination that a second set of criteria is met (e.g., a predetermined amount of time has elapsed and/or the first user experience is transitioning (or has transitioned) from the second portion of the user experience to a third portion of the user experience), causing a gradual decrease in the output volume of the first audio soundscape (e.g., as depicted in FIG. 7I). Causing a gradual increase in an output volume of the first audio soundscape when a first set of criteria is met, and causing a gradual decrease in the output volume of the first audio soundscape when a second set of criteria is met causes the computer system to automatically modify the first audio soundscape based on criteria met during the first user experience session.

In some embodiments, outputting the second audio soundscape (e.g., 774 or 794) for the second user experience session includes: in accordance with a determination that a third set of criteria is met (e.g., the first set of criteria is met), the computer system (e.g., 702) causes a gradual increase in an output volume of the second audio soundscape (e.g., as depicted in FIGS. 7D and/or 7K); and in accordance with a determination that a fourth set of criteria is met (e.g., the second set of criteria is met), the computer system causes a gradual decrease in the output volume of the second audio soundscape (e.g., as depicted in FIG. 7I).

In some embodiments, initiating (e.g., beginning) the first user experience session of the respective type in the XR environment includes the computer system (e.g., 702) outputting the first audio soundscape (e.g., 711 and/or 774) with a respective audio component (e.g., a starting sound and/or a sound that coincides with the start and/or end of the first user experience session). In some embodiments, while outputting the first audio soundscape for the first user experience session (e.g., and while the first audio soundscape does not include the respective audio component), the computer system initiates (e.g., in response to a user input, after a particular amount of time has elapsed, and/or after completion of at least a portion of the first user experience session) termination of the first user experience session (e.g., as depicted in FIG. 7I), wherein terminating the first user experience session includes outputting the first audio soundscape with the respective audio component. Outputting the first audio soundscape with the respective audio component when initiating the first user experience session of the respective type and when initiating termination of the first user experience session provides feedback to a user of the computer system about a state of the computer system (e.g., a state of starting or ending the first user experience session).

In some embodiments, initiating the second user experience session of the respective type in the XR environment includes the computer system (e.g., 702) outputting the second audio soundscape (e.g., 774 and/or 794) with a second respective audio component (e.g., a starting sound and/or a sound that coincides with the start and/or end of the second user experience session). While outputting the second audio soundscape for the second user experience session (e.g., and while the second audio soundscape does not include the second respective audio component), the computer system initiates (e.g., in response to a user input, after a particular amount of time has elapsed, and/or after completion of at least a portion of the second user experience session) termination of the second user experience session (e.g., as depicted in FIG. 7I), wherein terminating the second user experience session includes outputting the second audio soundscape with the second respective audio component.

In some embodiments, after termination of the first or second user experience session, the first audio soundscape is not output by the computer system (e.g., 702). In some embodiments, the soundscape has a same sound that is output at the start of the particular user experience session and at the end of the particular user experience session. In some embodiments, the soundscape has a same start sound at the start of different user experience sessions (and optionally has a different ending sound that is optionally the same ending sound for each user experience session). In some embodiments, the soundscape has a same ending sound at the end of different user experience sessions (and optionally has a different starting sound that is optionally the same starting sound for each user experience session). In some embodiments, the soundscape has a different start sound at the start of different user experience sessions. In some embodiments, the soundscape has a different ending sound at the end of different user experience sessions.

In some embodiments, outputting the first audio soundscape (e.g., 711 and/or 774) includes: while outputting the first audio soundscape with the first set of two or more audio components, the computer system (e.g., 702) outputs a third set of one or more audio components (e.g., audio components different from the first set), wherein the third set of one or more audio components is output at one or more randomly selected or pseudorandomly selected instances (e.g., moments) during the first user experience session. Outputting a third set of one or more audio components at one or more randomly selected or pseudorandomly selected instances during the first user experience session enables the computer system to provide a more realistic user experience while saving storage space by not requiring multiple different complete audio tracks to be stored and selected for playback. In some embodiments, outputting the second audio soundscape includes: while outputting the second audio soundscape with the second set of two or more audio components, outputting a fourth set of one or more audio components, wherein the fourth set of one or more audio components is output at one or more randomly selected or pseudorandomly selected instances during the second user experience session. In some embodiments, the first and/or second audio soundscapes include one or more sounds that are randomly (or pseudorandomly) generated throughout the soundscape to introduce variety to the soundscape.

In some embodiments, the set of available audio components includes a plurality of audio components that are selected to meet harmony criteria (e.g., the audio components are indicated to be harmonious) when output concurrently at one or more randomly selected or pseudorandomly selected instances (e.g., moments) during a user experience session of the respective type (e.g., during the first user experience session and/or during the second user experience session).

In some embodiments, while outputting the first audio soundscape (e.g., 711 and/or 774) with the first set of two or more audio components having a first perceived spatial location (e.g., 709-1 to 709-9) relative to a user (e.g., 701) of the computer system (e.g., 702), the computer system receives update data (e.g., data indicating a change in the state of the first user experience session). In response to receiving the update data, the computer system updates a state of the first user experience session, including: in accordance with a determination that the update data includes an indication that a first set of audio update criteria is met (e.g., a first predetermined amount of time has elapsed and/or the first user experience is transitioning (or has transitioned) from a first portion of the user experience to a second portion of the user experience), outputting the first audio soundscape with the first set of two or more audio components having a second perceived spatial location relative to the user of the computer system (e.g., as depicted in FIG. 7F), wherein the second perceived spatial location is different from the first perceived spatial location (e.g., outputting the first soundscape to have a perceived spatial location of the audio components that is moving toward the user); and in accordance with a determination that the update data includes an indication that a second set of audio update criteria is met (e.g., a second predetermined amount of time has elapsed and/or the first user experience is transitioning (or has transitioned) from the second portion of the user experience to a third portion of the user experience), outputting the first audio soundscape with the first set of two or more audio components having a third perceived spatial location relative to the user of the computer system (e.g., as depicted in FIG. 7G), wherein the third perceived spatial location is different from the second perceived spatial location (e.g., outputting the first soundscape to have a perceived spatial location of the audio components that is moving away from the user). In some embodiments, the perceived spatial audio location of the soundscape changes over time. Outputting the first audio soundscape with the first set of two or more audio components having a second or third perceived spatial location relative to the user of the computer system, based on whether the update data includes an indication that a first or second set of audio update criteria is met causes the computer system to automatically modify a perceived spatial location of the first audio soundscape based on audio update criteria met during the first user experience session.

In some embodiments, the first set of two or more audio components includes a first audio recording (e.g., 740-1, 740-2, 740-3, and/or 740-4) from a first audio source (e.g., a narrator, speaker, guide, coach, and/or person), and the second set of two or more audio components includes a second audio recording (e.g., 780-1 and/or 785-1) from the first audio source. Outputting the first soundscape with the first set of two or more audio components including a first audio recording from a first audio source, and outputting the second soundscape with the second set of two or more audio components including a second audio recording from the first audio source enables the computer system to provide a more realistic user experience while saving storage space by not requiring multiple different complete audio tracks to be stored and selected for playback. In some embodiments, the second audio recording is different from the first audio recording. In some embodiments, the second audio recording has one or more elements (e.g., dialogue, instructions, and/or phrases) in common with the first audio recording. In some embodiments, the second audio recording has one or more elements (e.g., intonation, tone, cadence, inflection, pitch, and/or accent) that are different from the first audio recording.

In some embodiments, the first audio recording from the first audio source (e.g., 740-1, 740-2, 740-3, and/or 740-4) includes a first dialogue (e.g., spoken words, instructions, and/or guidance) with a first set of speaking characteristics (e.g., intonation, cadence, tone, inflection, pitch, and/or accent), and the second audio recording from the first audio source (e.g., 780-1 and/or 785-1) includes the first dialogue with a second set of speaking characteristics different from the first set of speaking characteristics. Outputting the first soundscape with the first audio recording from the first audio source including a first dialogue with a first set of speaking characteristics, and outputting the second soundscape with the second audio recording including the first dialogue with a second set of speaking characteristics different from the first set of speaking characteristics enables the computer system to provide a more realistic user experience while saving storage space by not requiring multiple different complete audio tracks to be stored and selected for playback.

In some embodiments, the first audio recording from the first audio source (e.g., 740-1, 740-2, 740-3, and/or 740-4) includes a second dialogue (e.g., spoken words, instructions, and/or guidance), and the second audio recording from the first audio source (e.g., 780-1 and/or 785-1) includes a third dialogue different from the second dialogue. Outputting the first soundscape with the first audio recording from the first audio source including a second dialogue, and outputting the second soundscape with the second audio recording including a third dialogue different from the second dialogue enables the computer system to provide a more realistic user experience while saving storage space by not requiring multiple different complete audio tracks to be stored and selected for playback.

In some embodiments, aspects/operations of methods 800 and/or 900 may be interchanged, substituted, and/or added between these methods. For brevity, these details are not repeated here.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best use the invention and various described embodiments with various modifications as are suited to the particular use contemplated.

As described above, one aspect of the present technology is the gathering and use of data available from various sources to improve XR experiences of users. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to improve an XR experience of a user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of XR experiences, the present technology can be configured to allow users to select to "opt in" or "opt out" of participation in the collection of personal information data during registration for services or anytime thereafter. In another example, users can select not to provide data for customization of services. In yet another example, users can select to limit the length of time data is maintained or entirely prohibit the development of a customized service. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, an XR experience can generated by inferring preferences based on non-personal information data or a bare minimum amount of personal information, such as the content being requested by the device associated with a user, other non-personal information available to the service, or publicly available information.

What is claimed is:

1. A computer system configured to communicate with a display generation component and one or more sensors, the computer system comprising:

one or more processors; and memory storing one or more programs configured to be executed by the one or more processors, the one or more programs including instructions for:

displaying, via the display generation component, a user interface for a user experience session in an extended reality environment, including:

while the user experience session is active:

detecting, via the one or more sensors, one or more breathing characteristics of a user of the computer system;

displaying a user interface object having a plurality of particles that move based on the one or more breathing characteristics of the user of the computer system, including:

in accordance with a determination that a first breathing event of the user of the computer system satisfies a first set of criteria, wherein the first set of criteria is satisfied when the one or more breathing characteristics of the user indicate that the user is inhaling, displaying the particles of the user interface object moving in a first manner during the first breathing event of the user of the computer system, including:

displaying a first set of one or more particles having a first distance from a location corresponding to a viewpoint of the user of the computer system and having a first amount of movement towards the location corresponding to the viewpoint of the user while the user inhales; and displaying a second set of one or more particles different from the first set of one or more particles and having a second distance from the location corresponding to the viewpoint of the user of the computer system, different from the first distance, and having a second amount of movement towards the location corresponding to the viewpoint of the user while the user inhales, wherein the second amount of movement towards the location corresponding to the viewpoint of the user is greater than the first amount of movement towards the location corresponding to the viewpoint of the user; and in accordance with a determination that the first breathing event of the user of the computer system satisfies a second set of criteria, wherein the second set of criteria is satisfied when the one or more breathing characteristics of the user indicate that the user is exhaling, displaying the particles of the user interface object moving in a second manner different from the first manner during the first breathing event of the user of the computer system, including:

displaying the first set of one or more particles having a third distance from the location corresponding to the viewpoint of the user of the computer system and having a first amount of movement away from the location corresponding to the viewpoint of the user while the user exhales; and displaying the second set of one or more particles different from the first set of one or more particles and having a fourth distance from the location corresponding to the viewpoint of the user of the computer system, different from the third distance, and having a second amount of movement away from the location corresponding to the viewpoint of the user while the user exhales, wherein the second amount of movement away from the location corresponding to the viewpoint of the user is greater than the first amount of movement away from the location corresponding to the viewpoint of the user; and displaying the user interface object with an animated effect that is based on a predetermined biometric rhythm that is selected by the user of the computer system, including:

in accordance with a determination that the predetermined biometric rhythm is a first biometric rhythm, animating the user interface object based on a first pattern that corresponds to the first biometric rhythm; and in accordance with a determination that the predetermined biometric rhythm is a second biometric rhythm different from the first biometric rhythm, animating the user interface object based on a second pattern that corresponds to the second biometric rhythm.

2. The computer system of claim 1, wherein the computer system is in communication with an audio generation component, and wherein displaying the user interface for the user experience session includes:

prior to the user experience session being active, concurrently:

displaying, via the display generation component, a representation of the plurality of particles for the user interface object; and outputting, via the audio generation component, an audio soundscape for the user experience session.

3. The computer system of claim 1, wherein displaying the user interface for the user experience session includes:

prior to the user experience session being active:

displaying a start option that is selectable to initiate the user experience session; and displaying an indication of a duration of the user experience session.

4. The computer system of claim 1, wherein displaying the user interface for the user experience session includes:

prior to the user experience session being active:

displaying a set of one or more audio options that are selectable to choose an audio guide from a plurality of audio guides for the user experience session;

detecting an input directed to a first audio option, of the set of one or more audio options, that is selectable to choose an audio guide from the plurality of audio guides for the user experience session; and in response to detecting the input directed to the first audio option, selecting a first audio guide from the plurality of audio guides for the user experience session.

5. The computer system of claim 1, wherein the computer system is in communication with an audio generation component, the one or more programs further including instructions for:

while the user experience session is active:

outputting an audio component that has a perceived spatial location that moves based on the one or more breathing characteristics of the user of the computer system, including:

in accordance with a determination that a second breathing event of the user of the computer system satisfies a third set of criteria, outputting the audio component with a first perceived spatial location relative to the user of the computer system; and in accordance with a determination that the second breathing event of the user of the computer system satisfies a fourth set of criteria, outputting the audio component with a second perceived spatial location relative to the user of the computer system that is different from the first perceived spatial location.

6. The computer system of claim 1, wherein a portion of a physical environment of the user of the computer system is visible prior to the user experience session being active, the one or more programs further including instructions for:

initiating the user experience session, including:

displaying, via the display generation component, a dimming effect that gradually decreases visibility of the physical environment.

7. The computer system of claim 1, the one or more programs further including instructions for:

while the user experience session is active:

detecting, via the one or more sensors, one or more focus-based characteristics of the user of the computer system; and outputting feedback based on the one or more focus-based characteristics of the user of the computer system.

8. The computer system of claim 1, wherein movement of the plurality of particles is based on a set of one or more simulated physical parameters.

9. The computer system of claim 1, wherein displaying the user interface for the user experience session includes:

while the user experience session is active, detecting, via the one or more sensors, gaze data indicative of a gaze of the user of the computer system;

while displaying the user interface object having the plurality of particles that move based on the one or more breathing characteristics of the user of the computer system, detecting updated gaze data; and in response to detecting the updated gaze data:

in accordance with a determination that the updated gaze data indicates that the gaze of the user exceeds a gaze departure threshold, pausing the user experience session;

in accordance with a determination that the updated gaze data does not indicate that the gaze of the user exceeds the gaze departure threshold, forgoing pausing the user experience session; and in accordance with a determination that the updated gaze data indicates that the user has regained focus while the user experience session is paused, continuing the user experience session.

10. The computer system of claim 1, wherein:

displaying the user interface for the user experience session includes displaying the user interface with a set of visual characteristics selected randomly or pseudo-randomly from a set of available visual characteristics; and the computer system is in communication with an audio generation component, the one or more programs further including instructions for:

outputting, via the audio generation component, an audio soundscape for the user experience session, wherein the audio soundscape is output concurrently with displaying the user interface for the user experience session and outputting the audio soundscape includes outputting the audio soundscape with a first set of two or more audio components selected randomly or pseudorandomly from a set of available audio components.

11. The computer system of claim 1, wherein displaying the user interface for the user experience session includes:

while displaying the user interface object having a first displayed state in which the plurality of particles are displayed having a first amount of spacing for a first portion of the user experience session, detecting a transition from the first portion of the user experience session to a second portion of the user experience session; and in response to detecting the transition from the first portion of the user experience session to the second portion of the user experience session, displaying the user interface object having a second displayed state different from the first displayed state, wherein the plurality of particles are displayed for the second portion of the user experience session having a second amount of spacing different from the first amount of spacing.

12. The computer system of claim 1, wherein displaying the user interface for the user experience session includes:

while displaying the user interface object with the plurality of particles having an arrangement with a first average spacing between particles, detecting termination of the user experience session; and in response to detecting termination of the user experience session, displaying an animation of the plurality of particles moving to an arrangement with a second average spacing between particles, where the second average spacing is smaller than the first average spacing.

13. The computer system of claim 1, wherein displaying the user interface for the user experience session includes:

while the user experience session is active and an environment of the user of the computer system is visually obscured, detecting termination of the user experience session; and in response to detecting termination of the user experience session, initiating termination of the user experience session and gradually increasing visibility of the environment of the user.

14. The computer system of claim 1, wherein displaying the user interface for the user experience session includes:

while the user experience session is active, detecting termination of the user experience session; and in response to detecting termination of the user experience session, initiating termination of the user experience session and displaying an option that is selectable to continue the user experience session.

15. The computer system of claim 1, wherein displaying the user interface for the user experience session includes:

while the user experience session is active, detecting termination of the user experience session; and in response to detecting termination of the user experience session, initiating termination of the user experience session and displaying a history of data related to one or more previous user experience sessions.

16. The computer system of claim 1, wherein displaying the user interface for the user experience session includes causing at least a portion of an environment of the user of the computer system to be visible while the user experience session is active.

17. The computer system of claim 1, the one or more programs further including instructions for:

while the user experience session is active and while displaying the user interface object having a first displayed orientation relative to the user of the computer system, receiving data indicating a change in position of the user of the computer system from a first position in an environment to a second position in the environment different from the first position; and in response to receiving the data indicating a change in position of the user of the computer system, displaying the user interface object having a second displayed orientation relative to the user of the computer system different from the first displayed orientation.

18. The computer system of claim 1, wherein the user interface for the user experience session is capable of being displayed at one or more external computer systems associated with other users in an environment of the user experience session.

19. The computer system of claim 1, the one or more programs further including instructions for:

while the user experience session is active and while displaying the user interface object having the plurality of particles that move based on the one or more breathing characteristics of the user of the computer system, receiving data indicating a change in pose of a portion of the user of the computer system; and in response to receiving the data indicating the change in pose of the portion of the user of the computer system, updating display of the plurality of particles, including:

in accordance with a determination that the data indicating the change in pose of the portion of the user includes an indication that the portion of the user intersects a displayed location of a respective particle, modifying a displayed characteristic of the respective particle; and in accordance with a determination that the data indicating the change in pose of the portion of the user does not include an indication that the portion of the user intersects the displayed location of the respective particle, forgoing modifying the displayed characteristic of the respective particle.

20. A non-transitory computer-readable storage medium storing one or more programs configured to be executed by one or more processors of a computer system that is in communication with a display generation component and one or more sensors, the one or more programs including instructions for:

displaying, via the display generation component, a user interface for a user experience session in an extended reality environment, including:

while the user experience session is active:

detecting, via the one or more sensors, one or more breathing characteristics of a user of the computer system;

displaying a user interface object having a plurality of particles that move based on the one or more breathing characteristics of the user of the computer system, including:

in accordance with a determination that a first breathing event of the user of the computer system satisfies a first set of criteria, wherein the first set of criteria is satisfied when the one or more breathing characteristics of the user indicate that the user is inhaling, displaying the particles of the user interface object moving in a first manner during the first breathing event of the user of the computer system, including:

displaying a first set of one or more particles having a first distance from a location corresponding to a viewpoint of the user of the computer system and having a first amount of movement towards the location corresponding to the viewpoint of the user while the user inhales; and displaying a second set of one or more particles different from the first set of one or more particles and having a second distance from the location corresponding to the viewpoint of the user of the computer system, different from the first distance, and having a second amount of movement towards the location corresponding to the viewpoint of the user while the user inhales, wherein the second amount of movement towards the location corresponding to the viewpoint of the user is greater than the first amount of movement towards the location corresponding to the viewpoint of the user; and in accordance with a determination that the first breathing event of the user of the computer system satisfies a second set of criteria, wherein the second set of criteria is satisfied when the one or more breathing characteristics of the user indicate that the user is exhaling, displaying the particles of the user interface object moving in a second manner different from the first manner during the first breathing event of the user of the computer system, including:

displaying the first set of one or more particles having a third distance from the location corresponding to the viewpoint of the user of the computer system and having a first amount of movement away from the location corresponding to the viewpoint of the user while the user exhales; and displaying the second set of one or more particles different from the first set of one or more particles and having a fourth distance from the location corresponding to the viewpoint of the user of the computer system, different from the third distance, and having a second amount of movement away from the location corresponding to the viewpoint of the user while the user exhales, wherein the second amount of movement away from the location corresponding to the viewpoint of the user is greater than the first amount of movement away from the location corresponding to the viewpoint of the user; and displaying the user interface object with an animated effect that is based on a predetermined biometric rhythm that is selected by the user of the computer system, including:

in accordance with a determination that the predetermined biometric rhythm is a first biometric rhythm, animating the user interface object based on a first pattern that corresponds to the first biometric rhythm; and in accordance with a determination that the predetermined biometric rhythm is a second biometric rhythm different from the first biometric rhythm, animating the user interface object based on a second pattern that corresponds to the second biometric rhythm.

21. The non-transitory computer-readable storage medium of claim 20, wherein the computer system is in communication with an audio generation component, and wherein displaying the user interface for the user experience session includes:

prior to the user experience session being active, concurrently:

displaying, via the display generation component, a representation of the plurality of particles for the user interface object; and outputting, via the audio generation component, an audio soundscape for the user experience session.

22. The non-transitory computer-readable storage medium of claim 20, wherein displaying the user interface for the user experience session includes:

prior to the user experience session being active:

displaying a start option that is selectable to initiate the user experience session; and displaying an indication of a duration of the user experience session.

23. The non-transitory computer-readable storage medium of claim 20, wherein displaying the user interface for the user experience session includes:

prior to the user experience session being active:

displaying a set of one or more audio options that are selectable to choose an audio guide from a plurality of audio guides for the user experience session;

detecting an input directed to a first audio option, of the set of one or more audio options, that is selectable to choose an audio guide from the plurality of audio guides for the user experience session; and in response to detecting the input directed to the first audio option, selecting a first audio guide from the plurality of audio guides for the user experience session.

24. The non-transitory computer-readable storage medium of claim 20, wherein the computer system is in communication with an audio generation component, the one or more programs further including instructions for:

while the user experience session is active:

outputting an audio component that has a perceived spatial location that moves based on the one or more breathing characteristics of the user of the computer system, including:

in accordance with a determination that a second breathing event of the user of the computer system satisfies a third set of criteria, outputting the audio component with a first perceived spatial location relative to the user of the computer system; and in accordance with a determination that the second breathing event of the user of the computer system satisfies a fourth set of criteria, outputting the audio component with a second perceived spatial location relative to the user of the computer system that is different from the first perceived spatial location.

25. The non-transitory computer-readable storage medium of claim 20, wherein a portion of a physical environment of the user of the computer system is visible prior to the user experience session being active, the one or more programs further including instructions for:

initiating the user experience session, including:

displaying, via the display generation component, a dimming effect that gradually decreases visibility of the physical environment.

26. The non-transitory computer-readable storage medium of claim 20, the one or more programs further including instructions for:

while the user experience session is active:

detecting, via the one or more sensors, one or more focus-based characteristics of the user of the computer system; and outputting feedback based on the one or more focus-based characteristics of the user of the computer system.

27. The non-transitory computer-readable storage medium of claim 20, wherein movement of the plurality of particles is based on a set of one or more simulated physical parameters.

28. The non-transitory computer-readable storage medium of claim 20, wherein displaying the user interface for the user experience session includes:

while the user experience session is active, detecting, via the one or more sensors, gaze data indicative of a gaze of the user of the computer system;

while displaying the user interface object having the plurality of particles that move based on the one or more breathing characteristics of the user of the computer system, detecting updated gaze data; and in response to detecting the updated gaze data:

in accordance with a determination that the updated gaze data indicates that the gaze of the user exceeds a gaze departure threshold, pausing the user experience session;

in accordance with a determination that the updated gaze data does not indicate that the gaze of the user exceeds the gaze departure threshold, forgoing pausing the user experience session; and in accordance with a determination that the updated gaze data indicates that the user has regained focus while the user experience session is paused, continuing the user experience session.

29. The non-transitory computer-readable storage medium of claim 20, wherein:

displaying the user interface for the user experience session includes displaying the user interface with a set of visual characteristics selected randomly or pseudo-randomly from a set of available visual characteristics; and the computer system is in communication with an audio generation component, the one or more programs further including instructions for:

outputting, via the audio generation component, an audio soundscape for the user experience session, wherein the audio soundscape is output concurrently with displaying the user interface for the user experience session and outputting the audio soundscape includes outputting the audio soundscape with a first set of two or more audio components selected randomly or pseudorandomly from a set of available audio components.

30. The non-transitory computer-readable storage medium of claim 20, wherein displaying the user interface for the user experience session includes:

while displaying the user interface object having a first displayed state in which the plurality of particles are displayed having a first amount of spacing for a first portion of the user experience session, detecting a transition from the first portion of the user experience session to a second portion of the user experience session; and in response to detecting the transition from the first portion of the user experience session to the second portion of the user experience session, displaying the user interface object having a second displayed state different from the first displayed state, wherein the plurality of particles are displayed for the second portion of the user experience session having a second amount of spacing different from the first amount of spacing.

31. The non-transitory computer-readable storage medium of claim 20, wherein displaying the user interface for the user experience session includes:

while displaying the user interface object with the plurality of particles having an arrangement with a first average spacing between particles, detecting termination of the user experience session; and in response to detecting termination of the user experience session, displaying an animation of the plurality of particles moving to an arrangement with a second average spacing between particles, where the second average spacing is smaller than the first average spacing.

32. The non-transitory computer-readable storage medium of claim 20, wherein displaying the user interface for the user experience session includes:

while the user experience session is active and an environment of the user of the computer system is visually obscured, detecting termination of the user experience session; and in response to detecting termination of the user experience session, initiating termination of the user experience session and gradually increasing visibility of the environment of the user.

33. The non-transitory computer-readable storage medium of claim 20, wherein displaying the user interface for the user experience session includes:

while the user experience session is active, detecting termination of the user experience session; and in response to detecting termination of the user experience session, initiating termination of the user experience session and displaying an option that is selectable to continue the user experience session.

34. The non-transitory computer-readable storage medium of claim 20, wherein displaying the user interface for the user experience session includes:

while the user experience session is active, detecting termination of the user experience session; and in response to detecting termination of the user experience session, initiating termination of the user experience session and displaying a history of data related to one or more previous user experience sessions.

35. The non-transitory computer-readable storage medium of claim 20, wherein displaying the user interface for the user experience session includes causing at least a portion of an environment of the user of the computer system to be visible while the user experience session is active.

36. The non-transitory computer-readable storage medium of claim 20, the one or more programs further including instructions for:

while the user experience session is active and while displaying the user interface object having a first displayed orientation relative to the user of the computer system, receiving data indicating a change in position of the user of the computer system from a first position in an environment to a second position in the environment different from the first position; and in response to receiving the data indicating a change in position of the user of the computer system, displaying the user interface object having a second displayed orientation relative to the user of the computer system different from the first displayed orientation.

37. The non-transitory computer-readable storage medium of claim 20, wherein the user interface for the user experience session is capable of being displayed at one or more external computer systems associated with other users in an environment of the user experience session.

38. The non-transitory computer-readable storage medium of claim 20, the one or more programs further including instructions for:

while the user experience session is active and while displaying the user interface object having the plurality of particles that move based on the one or more breathing characteristics of the user of the computer system, receiving data indicating a change in pose of a portion of the user of the computer system; and in response to receiving the data indicating the change in pose of the portion of the user of the computer system, updating display of the plurality of particles, including:

in accordance with a determination that the data indicating the change in pose of the portion of the user includes an indication that the portion of the user intersects a displayed location of a respective particle, modifying a displayed characteristic of the respective particle; and in accordance with a determination that the data indicating the change in pose of the portion of the user does not include an indication that the portion of the user intersects the displayed location of the respective particle, forgoing modifying the displayed characteristic of the respective particle.

39. A method, comprising:

at a computer system that is in communication with a display generation component and one or more sensors:

displaying, via the display generation component, a user interface for a user experience session in an extended reality environment, including:

while the user experience session is active:

detecting, via the one or more sensors, one or more breathing characteristics of a user of the computer system;

displaying a user interface object having a plurality of particles that move based on the one or more breathing characteristics of the user of the computer system, including:

in accordance with a determination that a first breathing event of the user of the computer system satisfies a first set of criteria, wherein the first set of criteria is satisfied when the one or more breathing characteristics of the user indicate that the user is inhaling, displaying the particles of the user interface object moving in a first manner during the first breathing event of the user of the computer system, including:

displaying a first set of one or more particles having a first distance from a location corresponding to a viewpoint of the user of the computer system and having a first amount of movement towards the location corresponding to the viewpoint of the user while the user inhales; and displaying a second set of one or more particles different from the first set of one or more particles and having a second distance from the location corresponding to the viewpoint of the user of the computer system, different from the first distance, and having a second amount of movement towards the location corresponding to the viewpoint of the user while the user inhales, wherein the second amount of movement towards the location corresponding to the viewpoint of the user is greater than the first amount of movement towards the location corresponding to the viewpoint of the user; and in accordance with a determination that the first breathing event of the user of the computer system satisfies a second set of criteria, wherein the second set of criteria is satisfied when the one or more breathing characteristics of the user indicate that the user is exhaling, displaying the particles of the user interface object moving in a second manner different from the first manner during the first breathing event of the user of the computer system, including:

displaying the first set of one or more particles having a third distance from the location corresponding to the viewpoint of the user of the computer system and having a first amount of movement away from the location corresponding to the viewpoint of the user while the user exhales; and displaying the second set of one or more particles different from the first set of one or more particles and having a fourth distance from the location corresponding to the viewpoint of the user of the computer system, different from the third distance, and having a second amount of movement away from the location corresponding to the viewpoint of the user while the user exhales, wherein the second amount of movement away from the location corresponding to the viewpoint of the user is greater than the first amount of movement away from the location corresponding to the viewpoint of the user; and displaying the user interface object with an animated effect that is based on a predetermined biometric rhythm that is selected by the user of the computer system, including:

in accordance with a determination that the predetermined biometric rhythm is a first biometric rhythm, animating the user interface object based on a first pattern that corresponds to the first biometric rhythm; and in accordance with a determination that the predetermined biometric rhythm is a second biometric rhythm different from the first biometric rhythm, animating the user interface object based on a second pattern that corresponds to the second biometric rhythm.

40. The method of claim 39, wherein the computer system is in communication with an audio generation component, and wherein displaying the user interface for the user experience session includes:

prior to the user experience session being active, concurrently:

displaying, via the display generation component, a representation of the plurality of particles for the user interface object; and outputting, via the audio generation component, an audio soundscape for the user experience session.

41. The method of claim 39, wherein displaying the user interface for the user experience session includes:

prior to the user experience session being active:

displaying a start option that is selectable to initiate the user experience session; and displaying an indication of a duration of the user experience session.

42. The method of claim 39, wherein displaying the user interface for the user experience session includes:

prior to the user experience session being active:

displaying a set of one or more audio options that are selectable to choose an audio guide from a plurality of audio guides for the user experience session;

detecting an input directed to a first audio option, of the set of one or more audio options, that is selectable to choose an audio guide from the plurality of audio guides for the user experience session; and in response to detecting the input directed to the first audio option, selecting a first audio guide from the plurality of audio guides for the user experience session.

43. The method of claim 39, wherein the computer system is in communication with an audio generation component, the method further comprising:

while the user experience session is active:

outputting an audio component that has a perceived spatial location that moves based on the one or more breathing characteristics of the user of the computer system, including:

in accordance with a determination that a second breathing event of the user of the computer system satisfies a third set of criteria, outputting the audio component with a first perceived spatial location relative to the user of the computer system; and in accordance with a determination that the second breathing event of the user of the computer system satisfies a fourth set of criteria, outputting the audio component with a second perceived spatial location relative to the user of the computer system that is different from the first perceived spatial location.

44. The method of claim 39, wherein a portion of a physical environment of the user of the computer system is visible prior to the user experience session being active, the method further comprising:

initiating the user experience session, including:

displaying, via the display generation component, a dimming effect that gradually decreases visibility of the physical environment.

45. The method of claim 39, further comprising:

while the user experience session is active:

detecting, via the one or more sensors, one or more focus-based characteristics of the user of the computer system; and outputting feedback based on the one or more focus-based characteristics of the user of the computer system.

46. The method of claim 39, wherein movement of the plurality of particles is based on a set of one or more simulated physical parameters.

47. The method of claim 39, wherein displaying the user interface for the user experience session includes:

while the user experience session is active, detecting, via the one or more sensors, gaze data indicative of a gaze of the user of the computer system;

while displaying the user interface object having the plurality of particles that move based on the one or more breathing characteristics of the user of the computer system, detecting updated gaze data; and in response to detecting the updated gaze data:

in accordance with a determination that the updated gaze data indicates that the gaze of the user exceeds a gaze departure threshold, pausing the user experience session;

in accordance with a determination that the updated gaze data does not indicate that the gaze of the user exceeds the gaze departure threshold, forgoing pausing the user experience session; and in accordance with a determination that the updated gaze data indicates that the user has regained focus while the user experience session is paused, continuing the user experience session.

48. The method of claim 39, wherein:

displaying the user interface for the user experience session includes displaying the user interface with a set of visual characteristics selected randomly or pseudo-randomly from a set of available visual characteristics; and the computer system is in communication with an audio generation component, the method further comprising:

outputting, via the audio generation component, an audio soundscape for the user experience session, wherein the audio soundscape is output concurrently with displaying the user interface for the user experience session and outputting the audio soundscape includes outputting the audio soundscape with a first set of two or more audio components selected randomly or pseudorandomly from a set of available audio components.

49. The method of claim 39, wherein displaying the user interface for the user experience session includes:

while displaying the user interface object having a first displayed state in which the plurality of particles are displayed having a first amount of spacing for a first portion of the user experience session, detecting a transition from the first portion of the user experience session to a second portion of the user experience session; and in response to detecting the transition from the first portion of the user experience session to the second portion of the user experience session, displaying the user interface object having a second displayed state different from the first displayed state, wherein the plurality of particles are displayed for the second portion of the user experience session having a second amount of spacing different from the first amount of spacing.

50. The method of claim 39, wherein displaying the user interface for the user experience session includes:

while displaying the user interface object with the plurality of particles having an arrangement with a first average spacing between particles, detecting termination of the user experience session; and in response to detecting termination of the user experience session, displaying an animation of the plurality of particles moving to an arrangement with a second average spacing between particles, where the second average spacing is smaller than the first average spacing.

51. The method of claim 39, wherein displaying the user interface for the user experience session includes:

while the user experience session is active and an environment of the user of the computer system is visually obscured, detecting termination of the user experience session; and in response to detecting termination of the user experience session, initiating termination of the user experience session and gradually increasing visibility of the environment of the user.

52. The method of claim 39, wherein displaying the user interface for the user experience session includes:

while the user experience session is active, detecting termination of the user experience session; and in response to detecting termination of the user experience session, initiating termination of the user experience session and displaying an option that is selectable to continue the user experience session.

53. The method of claim 39, wherein displaying the user interface for the user experience session includes:

while the user experience session is active, detecting termination of the user experience session; and in response to detecting termination of the user experience session, initiating termination of the user experience session and displaying a history of data related to one or more previous user experience sessions.

54. The method of claim 39, wherein displaying the user interface for the user experience session includes causing at least a portion of an environment of the user of the computer system to be visible while the user experience session is active.

55. The method of claim 39, further comprising:

while the user experience session is active and while displaying the user interface object having a first displayed orientation relative to the user of the computer system, receiving data indicating a change in position of the user of the computer system from a first position in an environment to a second position in the environment different from the first position; and in response to receiving the data indicating a change in position of the user of the computer system, displaying the user interface object having a second displayed orientation relative to the user of the computer system different from the first displayed orientation.

56. The method of claim 39, wherein the user interface for the user experience session is capable of being displayed at one or more external computer systems associated with other users in an environment of the user experience session.

57. The method of claim 39, further comprising:

while the user experience session is active and while displaying the user interface object having the plurality of particles that move based on the one or more breathing characteristics of the user of the computer system, receiving data indicating a change in pose of a portion of the user of the computer system; and in response to receiving the data indicating the change in pose of the portion of the user of the computer system, updating display of the plurality of particles, including:

in accordance with a determination that the data indicating the change in pose of the portion of the user includes an indication that the portion of the user intersects a displayed location of a respective particle, modifying a displayed characteristic of the respective particle; and in accordance with a determination that the data indicating the change in pose of the portion of the user does not include an indication that the portion of the user intersects the displayed location of the respective particle, forgoing modifying the displayed characteristic of the respective particle.

* * * * *